US009206090B2

(12) United States Patent
Loh et al.

(10) Patent No.: US 9,206,090 B2
(45) Date of Patent: Dec. 8, 2015

(54) TRICYCLIC CHIRAL COMPOUNDS AND THEIR USE IN ASYMMETRIC CATALYSIS

(75) Inventors: Teck Peng Loh, Singapore (SG); Jian Xiao, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 13/062,193

(22) PCT Filed: Sep. 3, 2009

(86) PCT No.: PCT/SG2009/000312
§ 371 (c)(1),
(2), (4) Date: Jul. 22, 2011

(87) PCT Pub. No.: WO2010/027334
PCT Pub. Date: Mar. 11, 2010

(65) Prior Publication Data
US 2011/0269972 A1 Nov. 3, 2011

Related U.S. Application Data

(60) Provisional application No. 61/093,843, filed on Sep. 3, 2008.

(51) Int. Cl.
*C07D 487/04* (2006.01)
*C07B 53/00* (2006.01)

(52) U.S. Cl.
CPC .............. *C07B 53/00* (2013.01); *C07D 487/04* (2013.01)

(58) Field of Classification Search
CPC ............................... C07D 487/04; C07B 53/00
See application file for complete search history.

(56) References Cited

FOREIGN PATENT DOCUMENTS

EP 0 457 318 A1 11/1991

OTHER PUBLICATIONS

Burgaud et al. (Tetrahedron: Asymmetry (1995), 6(5), 1081-4).*
Xiao, Xu, Lu, and Loh (Org. Lett., (2010), v. 12, n. 6, p. 1220-1223—published online Feb. 16, 2010).*
Xiao, Wong, Lu, and Loh (Adv. Synth. Catal., (2010), 352, p. 1107-1112—published online Apr. 26, 2010).*
Allenmark, "Chiroptical methods in the stereochemical analysis of natural products," *Nat. Prod. Rep.* 17:145-155, 2000.
Basavaiah et al., "(2S,5S)-1,3-Diaza-2-phospha-2-oxo-2-chloro-3-phenylbicyclo[3.3.0]octane: a novel chiral source for borane-mediated catalytic chiral reductions," *Tetrahedron: Asymmetry* 13:1125-1128, 2002.
Becke, "A new mixing of Hartree-Fock and local density-functional theories," *J. Chem. Phys.* 98(2):1372-1377, 1993.
Becke, "Density-functional thermochemistry. III. The role of exact exchange," *J. Chem. Phys.* 98(7):5648-5652, 1993.

Borman, "Combinatorial Catalysts: Methods devised to create arrays of catalysts to screen for enantioselective activity," *C&EN Washington*, pp. 37-39, 1996.
Bourne et al., "Enantiospecific Synthesis with Amino Acids. Part 1. Tryptophan as a Chiron for the Synthesis of α-Substituted Tryptophan Derivatives," *J. Chem. Soc. Perkin Trans. 1*:1693-1699, 1991.
Bouzemi et al., "Combined lipase-catalyzed resolution/Mitsunobu esterification for the production of enantiomerically enriched arylalkyl carbinols," *Tetrahedron: Asymmetry* 17:797-800, 2006.
Burk et al., "A Catalyst for Efficient and Highly Enantioselective Hydrogenation of Aromatic, Heteroaromatic, and α-β-Unsaturated Ketones," *Organic Letters* 2(26):4173-4176, 2000.
Chen et al., "Organocatalyzed Highly Enantioselective Direct Aldol Reactions of Aldehydes with Hydroxyacetone and Fluoroacetone in Aqueous Media: The Use of Water to Control Regioselectivity," *Chem. Eur. J.* 13:689-701, 2007.
Clarke et al., "Self-Assembly of Organocatalyst: Fine-Tuning Organocatalytic Reactions," *Angew. Chem. Int. Ed.* 46:930-933, 2007.
Cole et al., "Discovery of Chiral Catalysts through Ligand Diversity: Ti-Catalyzed Enantioselective Addition of TMSCN to *meso* Epoxides," *Angew. Chem. Int. Ed. Engl.* 35(15):1668-1671, 1996.
Corey et al., "A New Process for the Generation of 1,3,2-Oxazaborolidines, Catalysts for Enantioselective Synthesis," *Tetrahedron Letters* 33(29):4141-4144, 1992.
Corey et al., "A Stable and Easily Prepared Catalyst for the Enantioselective Reduction of Ketones. Applications to Multistep Syntheses," *J. Am. Chem. Soc.* 109:7925-7926, 1987.
Corey et al., "Highly Enantioselective Borane Reduction of Ketones Catalyzed by Chiral Oxazaborolidines. Mechanism and Synthetic Implications," *J. Am. Chem. Soc.* 109:5551-5553, 1987.
Corey et al., "Reduction of Carbonyl Compounds with Chiral Oxazaborolidine Catalysts: A New Paradigm for Enantioselective Catalysis and a Powerful New Synthetic Method," *Angew. Chem. Int. Ed.* 37:1986-2012, 1998.
Corey et al., "X-Ray Crystal Structure of a Chiral Oxazaborolidine Catalyst for Enantioselective Carbonyl Reduction," *Tetrahedron Letters* 33(24):3429-3430, 1992.

(Continued)

*Primary Examiner* — Robert Havlin
(74) *Attorney, Agent, or Firm* — Seed IP Law Group PLLC

(57) ABSTRACT

The present invention relates to a compound of general Formula (XX), its formation and its use in asymmetric catalysis. In Formula (XX) R and $R^{31}$ are independently —$COOR^3$, —$R^4COOR^3$, —$R^4CHO$, —$R^4COR^3$, —$R^4CONR^5R^6$, —$R^4COX$, —$R^4OP(=O)(OH)_2$, —$R^4P(=O)(OH)_2$, —$R^4C(O)C(R^3)CR^5R^6$ and —$R^4CO_2COR^3$. In addition, $R^{31}$ may also be hydrogen. $R^3$, $R^5$ and $R^6$ are independently hydrogen, an aliphatic group with a main chain having 1 to about 20 carbon atoms, an alicyclic group, an aromatic group, an arylaliphatic group or an arylalicyclic group, comprising 0 to about 3 heteroatoms independently selected from the group consisting of N, O, S, Se and Si. $R^4$ an aliphatic bridge with a main chain having 1 to about 20 carbon atoms, an alicyclic bridge, an aromatic bridge, an arylaliphatic bridge or an arylalicyclic bridge, comprising 0 to about 3 heteroatoms independently selected from the group consisting of N, O, S, Se and Si, and X is halogen. In Formula (XX) $R^{30}$ is —C(OH)$R^1R^2$ or —$COOR^{14}$, wherein $R^1$, $R^2$ and $R^{14}$ are independently hydrogen, an aliphatic group with a main chain having 1 to about 20 carbon atoms, an alicyclic group, an aromatic group, an arylaliphatic group or an arylalicyclic group, comprising 0 to about 3 heteroatoms independently selected from the group consisting of N, O, S, Se and Si.

10 Claims, 31 Drawing Sheets

(56) References Cited

OTHER PUBLICATIONS

Crich et al., "Chemistry of the Hexahydropyrrolo[2,3-*b*]indoles: Configuration, Conformation, Reactivity, and Applications in Synthesis," *Acc. Chem. Res.* 40:151-161, 2007.
Crich et al., "On the Reaction of Tryptophan Derivatives with *N*-Phenylselenyl Phthalimide: The Nature of the Kinetic and Thermodynamic Hexahydropyrrolo[2,3-*b*]indole Products. Alkylation of Tryptophan with Inversion of Configuration," *J. Org. Chem.* 64:7218-7223, 1999.
Dale et al., "α-Methoxy-α-trifluoromethylphenylacetic Acid, a Versatile Reagent for the Determination of Enantiomeric Compositon of Alcohols and Amines," *J. Org. Chem.* 34(9):2543-2549, 1969.
Depew et al., "Total Synthesis of 5-*N*-Acetylardeemin and Amauromine: Practical Routes to Potential MDR Reversal Agents," *J. Am. Chem. Soc.* 121:11953-11963, 1999.
Ditchfield et al., "Self-Consistent Molecular-Orbital Methods. IX. An Extended Gaussian-Type Basis for Molecular-Orbital Studies of Organic Molecules," *The Journal of Chemical Physics* 54(2):724-728, 1971.
Du et al., "Structurally Well-Defined, Recoverable $C_3$-Symmetric Tris(β-hydroxy phosphoramide)-Catalyzed Enantioselective Borane Reduction of Ketones," *Organic Letters* 8(7):1327-1330, 2006.
Gennari et al., "Combinatorial Libraries: Studies in Molecular Recognition and the Quest for New Catalysts," *Liebigs Ann./Recueil*, pp. 637-647, 1997.
Harper et al., "Stereochemical Analysis by Solid-State NMR: Structural Predictions in Ambuic Acid," *J. Org. Chem.* 68:4609-4614, 2003.
Hayashi et al., "Diphenylprolinol Siyl Ethers as Efficient Organocatalysts for the Asymmetric Michael Reaction of Aldehydes and Nitroalkenes," *Angew. Chem. Int. Ed.* 44:4212-4215, 2005.
Hino et al., *The Alkaloids*: Chemistry and Pharmacology vol. 34, Academic Press, Inc., 1988, Chap. 1, "Chemistry and Reactions of Cyclic Tautomers of Tryptamines and Tryptophans," pp. 1-75.
Kanth et al., "A new catalytic enantioselective reducing reagent system from (-)-α,α-diphenylpyrrolidinemethanol and 9-borabicyclo[3.3.1]nonane, especially effective for hindered and substituted aralkylketones," *Tetrahedron* 58:1069-1074, 2002.
Krueger et al., "Ti-Catalyzed Enantioselective Addition of Cyanide to Imines. A Practical Synthesis of Optically Pure α-Amino Acids," *J. Am. Chem. Soc.* 121:4284-4285, 1999.
Le Gac et al., "Self-assembly via ionic interactions of calix[6]arene-based receptors displaying remarkable host-guest properties toward neutral guests," *Tetrahedron* 63:10721-10730, 2007.
Lee et al., "Development of the Colle-Salvetti correlation-energy formula into a functional of the electron density," *Physical Review B* 37(2):785-789, 1988.
Liu et al., "Highly efficient and recyclable heterogeneous asymmetric transfer hydrogenation of ketones in water," *Chem. Commun.*, pp. 2070-2071, 2004.
Ma et al., "Asymmetric Transfer Hydrogenation of Prochiral Ketones in Aqueous Media with New Water-Soluble Chiral Vicinal Diamine as Ligand," *Organic Letters* 5(12):2103-2106, 2003.
Mandal et al., "Modularly Designed Organocatalytic Assemblies for Direct Nitro-Michael Addition Reactions," *Angew. Chem. Int. Ed.* 47:7714-7717, 2008.
Mase et al., "Organocatalytic Direct Michael Reaction of Ketones and Aldehydes with β-Nitrostyrene in Brine," *J. Am. Chem. Soc.* 128:4966-4967, 2006.
Mathre et al., "A Practical Process for the Preparation of Tetrahydro-1-methyl-3,3-diphenyl-1*H*,3*H*-pyrrolo[1,2-*c*]-[1,3,2]oxazaborole-Borane. A Highly Enantioselective Stoichiometric and Catalytic Reducing Agent," *J. Org. Chem.* 58:2880-2888, 1993.
Naud et al., "Enantioselective Ketone Hydrogenation: From R&D to Pilot Scale with Industrially Viable Ru/Phosphine-Oxazoline Complexes," *Organic Process Research & Development* 11(3):519-523, 2007.
Palomo et al., "Highly Efficient Asymmetric Michael Addition of Aldehydes to Nitroalkenes Catalyzed by a Simple *trans*-4-Hydroxyprolylamide," *Angew. Chem. Int. Ed.* 45:5984-5987, 2006.
Pfaltz et al., "Design of chiral ligands for asymmetric catalysis: From $C_2$-symmetric P,P- and N,N-ligands to sterically and electronically nonsymmetrical P,N-ligands," *PNAS* 101(16):5723-5726, 2004.
Pollard et al., "Effective synthesis of (*S*)-3,5-bistrifluoromethylphenyl ethanol by asymmetric enzymatic reduction," *Tetrahedron: Asymmetry* 17:554-559, 2006.
Riccio et al., "Stereochemical analysis of natural products. Approaches relying on the combination of NMR spectroscopy and computational methods," *Pure Appl. Chem.* 75(2-3):295-308, 2003.
Schmuck et al., "Highly Stable Self-Assembly in Water: Ion Pair Driven Dimerization of a Guanidiniocarbonyl Pyrrole Carboxylate Zwitterion," *J. Am. Chem. Soc.* 125:452-459, 2003.
Seebach et al., "Synthesis of Open-Chain 2,3-Disubstituted 4-nitroketones by Diastereoselective *Michael*-addition of (*E*)-Enamines to (*E*)-Nitroolefins. A Topological Rule for C,C-Bond Forming Processes between Prochiral Centres," *Helvetica Chimica Acta* 64(5):1413-1423, 1981.
Seebach et al., "On the Steric Course of the Reaction of Enamines Derived from Open-Chain Aldehydes and Ketones with Nitro-olefins Yielding 2,3-Disubstituted 4-Nitroketones," *Helvetica Chimia Acta* 68, pp. 162-172, 1985 (w/ English abstract).
Sigman et al., "Schiff Base Catalysts for the Asymmetric Strecker Reaction Identified and Optimized from Parallel Synthetic Libraries," *J. Am. Chem. Soc.* 120:4901-4902, 1998.
Sulzer-Mossé et al., "Chiral amines as organocatalysts for asymmetric conjugate addition to nitroolefins and vinyl sulfones via enamine activation," *Chem. Commun.*, pp. 3123-3135, 2007.
Tagat et al., "Piperazine-Based CCR5 Antagonists as HIV-1 Inhibitors. II. Discovery of 1-[(2,4-Dimethyl-3-pyridinyl)carbonyl]-4-methyl-4-[3(*S*)-methyl-4-[1-(*S*)-[4-(trifluoro-methyl)phenyl]ethyl]-1-piperazinyl]-piperidine *N*1-Oxide (Sch-350634), an Orally Bioavailable, Potent CCR5 Antagonist," *J. Med. Chem.* 44:3343-3346, 2001.
Taniguchi et al., "Cyclic Tautomers of Tryptophans and Tryptamines-4[1]. Synthesis of Cyclic Tautomers of Tryptophans and Tryptamines," *Tetrahedron* 37:1487-1494, 1981.
Tsogoeva, "Recent Advances in Asymmetric Organocatalytic 1,4-Conjugate Additions," *Eur. J. Org. Chem.*, pp. 1701-1716, 2007.
Vicario et al., "Organocatalytic Enantioselective Michael and Hetero-Michael Reactions," *Synthesis* 14:2065-2092, 2007.
Wang et al., "Direct, Highly Enantioselective Pyrrolidine Sulfonamide Catalyzed Michael Addition of Aldehydes to Nitrostyrenes," *Angew. Chem. Int. Ed.* 44:1369-1371, 2005.
Wang et al., "Enantio- and Diastereoselective Michael Addition Reactions of Unmodified Aldehydes and Ketones with Nitroolefins Catalyzed by a Pyrrolidine Sulfonamide," *Chem. Eur. J.* 12:4321-4332, 2006.
Xu et al., "Ruthenium(II) Complexes of Monodonor Ligands: Efficient Reagents for Asymmetric Ketone Hydrogenation," *J. Org. Chem.* 70:8079-8087, 2005.
Yoon et al., "Privileged Chiral Catalysts," *Science* 299:1691-1693, 2003.
Coste et al., "Copper-Catalyzed Cyclization of Iodo-tryptophans: A Straightforward Synthesis of Pyrroloindoles," *Organic Letters* 10(17):3841-3844, 2008.
Ekhato et al., "Tetrahydro-pyrrolo-[2,3-b]indole-1,2,8-tricarboxylic Acid Ester in the Enantiospecific Preparation of α-Methyltryptophan: Application in the Preparation of Carbon-14 Labeled PD 145942 and PD 154075," *Journal of Labelled Compounds and Radiopharmaceuticals* 39(12):1019-1038, 1997.

* cited by examiner

The X-ray structure of 6a.

The X-ray structure of 7a.

(VIII)
bowl-shaped conformation (IX)
S-shaped conformation

Chem 3D model for "bowl"

Chem 3D model for "S"

89%, 79% ee

23%, 63% ee

32%, 49% ee

40%, 57% ee (XXXA)

(XXXB)

(XXXC)

| Entry | Product | Yield (%)[a] | e. e.[b] |
|---|---|---|---|
| 1 | 1-phenylethanol | 98 | 81 |
| 2 | 2-bromo-1-phenylethanol | 98 | 92 |
| 3 | 1-(naphthalen-2-yl)ethanol | 99 | 89 |
| 4 | 1-(3-(trifluoromethyl)phenyl)ethanol | 98 | 86 |
| 5 | 1-(3-nitrophenyl)ethanol | 98 | 92 |
| 6 | 1-(4-nitrophenyl)ethanol | 96 | 92 |
| 7 | 1-(3,4-difluorophenyl)ethanol | 99 | 97 |
| 8 | 1-(3,5-difluorophenyl)ethanol | 99 | 93 |
| 9 | 1-(4-(trifluoromethyl)phenyl)ethanol | 99 | 97 |
| 10 | 1-(3,5-bis(trifluoromethyl)phenyl)ethanol | 99 | 93 |
| 11 | 1-(3-fluorophenyl)ethanol | 99 | 90 |
| 12 | 4-phenylbutan-2-ol | 99 | 50 |

| Entry | ligand | Solvent | Yield (%)[a] | e.e.(%)[b] |
|---|---|---|---|---|
| 1[c] | 7a | THF | 96 | 37 |
| 2[d] | 7a | THF | 99 | 85 |
| 3 | 7a | THF | 99 | 89 |
| 4 | 7b | THF | 96 | 85 |
| 5 | 7c | THF | 96 | 40 |
| 6 | 7d | THF | 98 | 85 |
| 7 | 7e | THF | 97 | 81 |
| 8 | 7f | THF | 96 | 60 |
| 9 | 7g | THF | 96 | 72 |
| 10 | 7h | THF | 96 | 75 |
| 11 | 7a | Dioxane | 95 | 36 |
| 12 | 7a | CH$_2$Cl$_2$ | 92 | 59 |
| 13 | 7a[e] | THF | 98 | 89 |
| 14 | 7a[f] | THF | 98 | 89 |
| 15 | 7a[g] | THF | 98 | 86 |

Fig. 13A
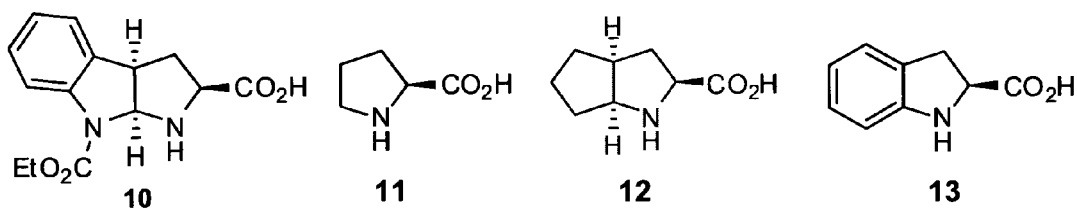
Fig. 13B
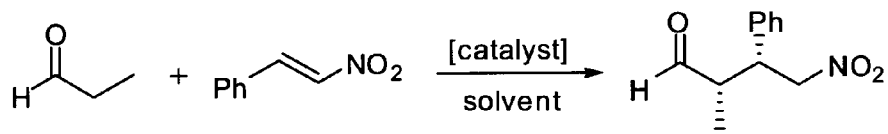
Fig. 13C
| Entry | Catalyst | Solvent | Loading (mol %) | Yield (%)[a] | Dr[b] | ee (%)[c] |
|---|---|---|---|---|---|---|
| 1 | 10 | MeOH | 10 | 86 | 91:9 | 96 |
| 2 | 11 | MeOH | 10 | 30 | 85:15 | -20 |
| 3 | 12 | MeOH | 10 | <10 | 86:14 | -20 |
| 4 | 13 | MeOH | 10 | <10 | N.D. | N.D. |
| 5 | 10/DMAP | MeOH | 5 | 96 | 91:9 | >99 |
| 6 | 10/DMAP | MeOH | 2 | 92 | 75:25 | >99 |
| 7 | 10/DMAP | H$_2$O | 5 | 90 | 91:9 | >99 |
| 8 | 10/DMAP | brine | 10 | 10 | 86:14 | 96 |
| 9 | 10 | H$_2$O | 10 | N.R. | N.R. | N.R. |
| 10 | 11/DMAP | H$_2$O | 10 | N.R. | N.R. | N.R. |
| 11 | 12/DMAP | H$_2$O | 10 | N.R. | N.R. | N.R. |
| 12 | 13/DMAP | H$_2$O | 10 | N.R. | N.R. | N.R. |

89% yield, 79% ee

| Entry | Product | Catalyst (mol %) | Solvent | Time (h) | Yield (%)[a] | syn/anti[b] | ee (%)[c] |
|---|---|---|---|---|---|---|---|
| 1 | (Ph product) | 5 | MeOH | 8 | 96 | 91:9 | >99 |
|   |   |   | H$_2$O | 12 | 90 | 91:9 | >99 |
| 2 | (4-BrC$_6$H$_4$ product) | 5 | MeOH | 8 | 87 | 86:14 | 96 |
|   |   |   | H$_2$O | 12 | 75 | 63:37 | 91 |
| 3 | (4-MeOC$_6$H$_4$ product) | 5 | MeOH | 8 | 79 | 72:28 | 93 |
|   |   |   | H$_2$O | 12 | 76 | 63:37 | 92 |
| 4 | (2-furyl product) | 5 | MeOH | 8 | 94 | 88:12 | 96 |
|   |   |   | H$_2$O | 12 | 61 | 64:36 | 95 |
| 5 | (1-Naphthyl product) | 5 | MeOH | 24 | 92 | 91:9 | 96 |
|   |   |   | H$_2$O | 36 | 87 | 78:22 | 96 |

(cont. on next page)

| Entry | Product | Catalyst (mol %) | Solvent | Time (h) | Yield (%)[a] | syn/anti[b] | ee (%)[c] |
|---|---|---|---|---|---|---|---|
| 6 | (Cy) | 10 | MeOH | 72 | 60 | 60:40 | 93 |
|   |     |    | H$_2$O | 96 | 56 | 60:40 | 99 |
| 7 | (CH$_2$CH$_2$Ph) | 10 | MeOH | 72 | 70 | 57:43 | 96 |
|   |     |    | H$_2$O | 96 | 65 | 57:43 | 96 |
| 8 | (Ph, Et) | 5 | MeOH | 48 | 89 | 91:9 | 98 |
|   |     |    | H$_2$O | 56 | 83 | 91:9 | 98 |
| 9 | (Ph, iPr) | 10 | MeOH | 48 | 86 | 99:1 | 99 |
|   |     |    | H$_2$O | 24 | 94 | 96:4 | 99 |
| 10 | (4-BrC$_6$H$_4$, iPr) | 10 | MeOH | 72 | 86 | 98:2 | >99 |
|    |    |    | H$_2$O | 36 | 85 | 98:2 | >99 |
| 11 | (1-Naphthyl, iPr) | 10 | MeOH | 72 | 86 | 96:4 | 99 |
|    |    |    | H$_2$O | 96 | 85 | 96:4 | 99 |
| 12 | (Ph, gem-diMe) | 10 | MeOH | 96 | 88 | ---- | 95 |

(cont. on next page)

Fig. 14 (cont.)
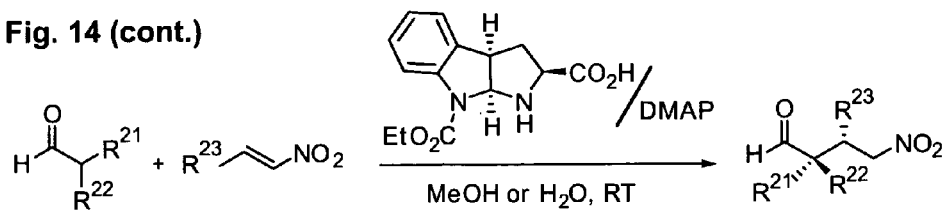
| Entry | Product | Catalyst (mol %) | Solvent | Time (h) | Yield (%)[a] | syn/anti[b] | ee (%)[c] |
|---|---|---|---|---|---|---|---|
| 13 | 4-BrC₆H₄ | 10 | MeOH | 96 | 85 | --- | 95 |
| 14 | 2-furyl | 10 | MeOH | 96 | 88 | --- | 95 |
| 15 | 4-MeOC₆H₄ | 10 | MeOH | 96 | 86 | --- | 92 |
| 16 | 2-Naphthyl | 10 | MeOH | 96 | 86 | --- | 95 |
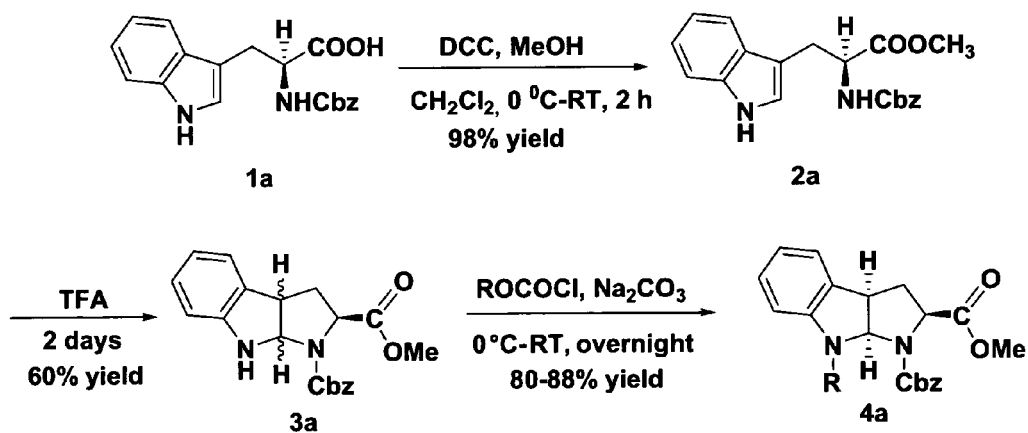
Fig. 15
(cont. on next page)

Fig. 15 (cont.)  (a) R= CO$_2$C$_2$H$_5$, R'=Ph; (b) R= OCOC$_2$H$_5$, R'=H; (c) R= CO$_2$C$_2$H$_5$, R'=m-xyl; (d) R= CO$_2$CH$_3$, R'=Ph; (e) R=COCH$_3$, R'=Ph; (f) R= CO$_2$CH(CH$_3$)$_2$, R'=Ph; (g) R= CO$_2$CH$_2$CH(CH$_3$)$_2$, R'=Ph; (h) R= CO$_2$C$_6$H$_5$, R'=Ph

≡

Crystal Structure of 6a

Crystal Structure of 7a

| Peak # | RetTime [min] | Type | Width [min] | Area [mAU*s] | Height [mAU] | Area % |
|---|---|---|---|---|---|---|
| 1 | 8.626 | MM | 0.3158 | 5618.43359 | 296.55637 | 49.7512 |
| 2 | 10.329 | MM | 0.3608 | 5674.63721 | 262.15540 | 50.2488 |

Totals :   1.12931e4   558.71176

| Peak # | RetTime [min] | Type | Width [min] | Area [mAU*s] | Height [mAU] | Area % |
|---|---|---|---|---|---|---|
| 1 | 8.662 | MM | 0.2686 | 1303.79114 | 80.88783 | 90.8346 |
| 2 | 10.327 | MM | 0.2722 | 131.55505 | 8.05415 | 9.1654 |

Totals :   1435.34619   88.94198

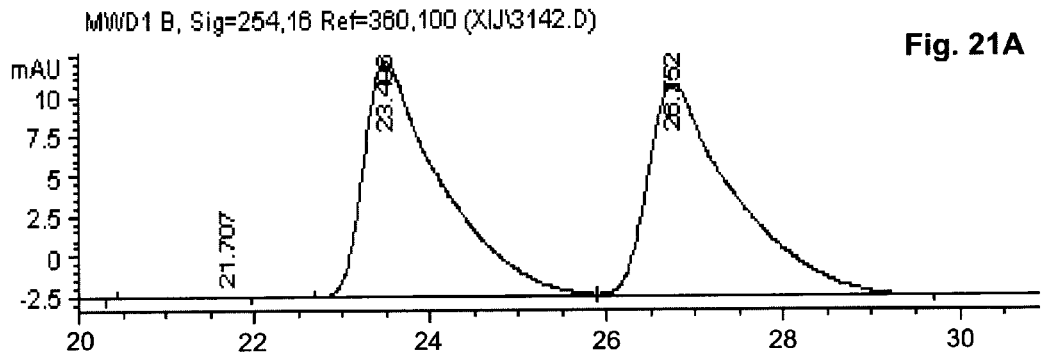
Fig. 21A
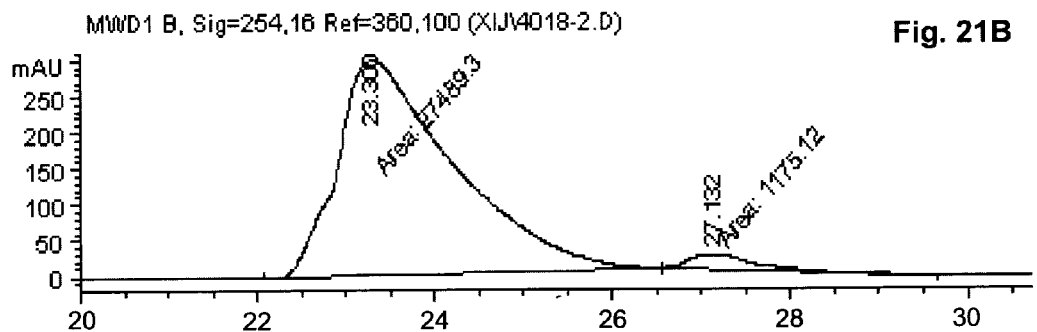
Fig. 21B
Fig. 21C
```
Peak  RetTime  Type  Width    Area        Height      Area
 #    [min]          [min]    [mAU*s]     [mAU]       %
----|--------|----|--------|-----------|-----------|--------|
 1    23.493   MM   1.0084   793.66083   13.11772    50.1506
 2    26.752   MM   1.1196   788.89288   11.74333    49.8494
Totals :                     1582.55371  24.86106
```
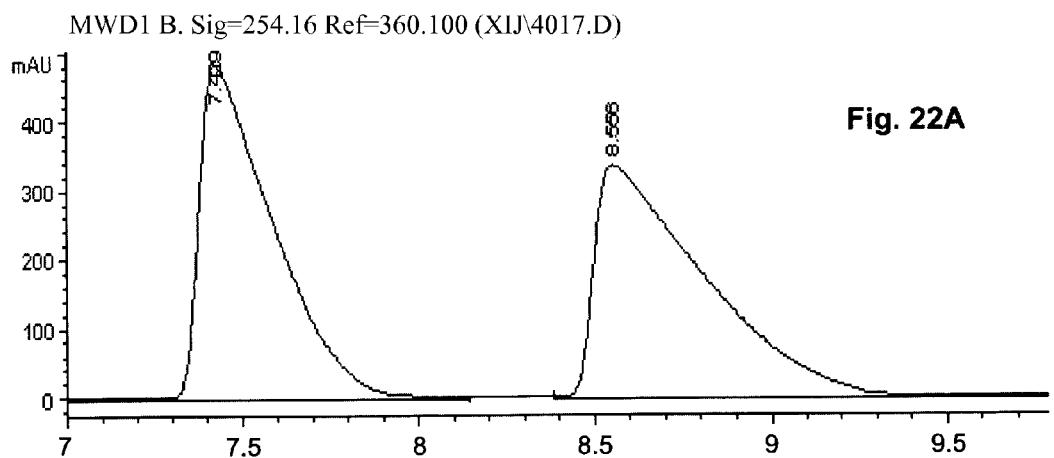
Fig. 22A Fig. 22B
| Peak # | RetTime [min] | Type | Width [min] | Area [mAU*s] | Height [mAU] | Area % |
|---|---|---|---|---|---|---|
| 1 | 7.429 | VV | 0.2103 | 7075.01709 | 484.78839 | 49.4591 |
| 2 | 8.556 | VV | 0.3014 | 7229.77734 | 338.16534 | 50.5409 |
Totals :     1.43048e4    822.95374
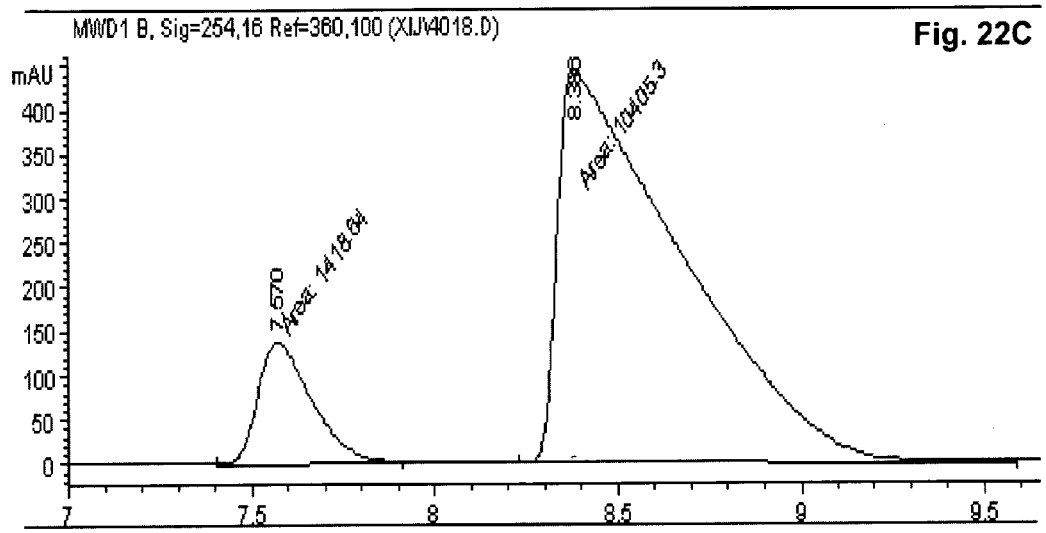
Fig. 22C
Fig. 22D
| Peak # | RetTime [min] | Type | Width [min] | Area [mAU*s] | Height [mAU] | Area % |
|---|---|---|---|---|---|---|
| 1 | 7.570 | MM | 0.1713 | 1418.63843 | 138.00569 | 11.9980 |
| 2 | 8.386 | MM | 0.3941 | 1.04053e4 | 439.99146 | 88.0020 |
Totals :     1.18240e4    577.99715
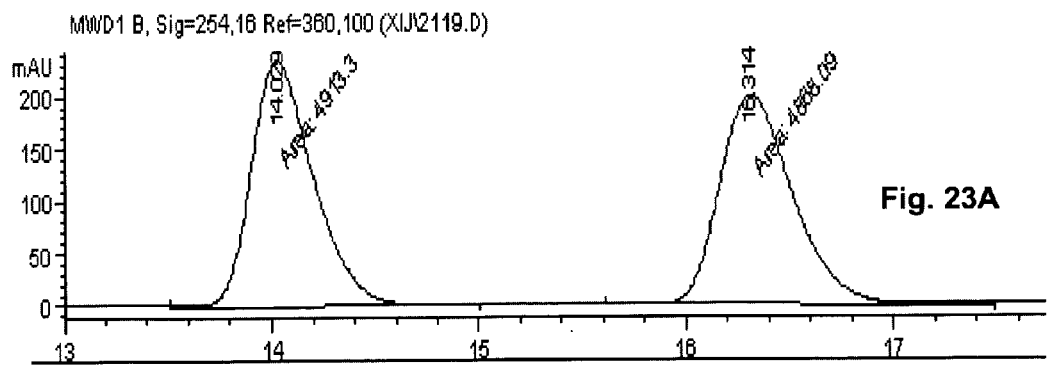
Fig. 23A

```
Peak RetTime Type  Width     Area       Height      Area
 #   [min]         [min]     [mAU*s]    [mAU]       %
----|-------|----|--------|-----------|-----------|--------|
  1  14.029 MM    0.3488   4913.30078  234.77055  50.2311
  2  16.314 MM    0.4066   4868.09326  199.54494  49.7689
Totals :                   9781.39404  434.31549
```
Fig. 23B
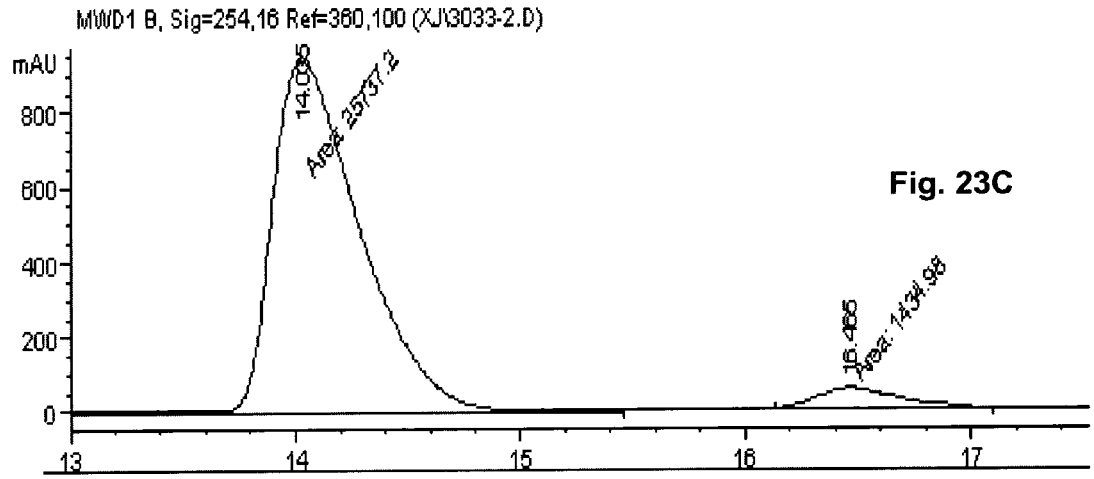
Fig. 23C
```
Signal 2: MWD1 B, Sig=254,16 Ref=360,100
```
Fig. 23D
```
Peak RetTime Type  Width     Area       Height      Area
 #   [min]         [min]     [mAU*s]    [mAU]       %
----|-------|----|--------|-----------|-----------|--------|
  1  14.035 MM    0.4564   2.57372e4   939.79205  94.7189
  2  16.465 MM    0.4318   1434.98071   55.38373   5.2811
```
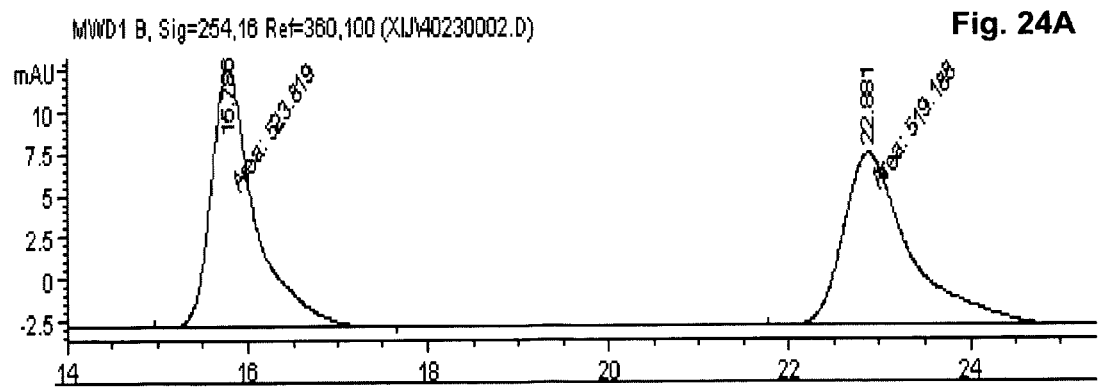
Fig. 24A

Fig. 24B
| Peak # | RetTime [min] | Type | Width [min] | Area [mAU*s] | Height [mAU] | Area % |
|---|---|---|---|---|---|---|
| 1 | 15.786 | MM | 0.5623 | 523.81909 | 15.52557 | 50.2220 |
| 2 | 22.881 | MM | 0.8419 | 519.18811 | 10.27842 | 49.7780 |
Totals : 1043.00720  25.80399
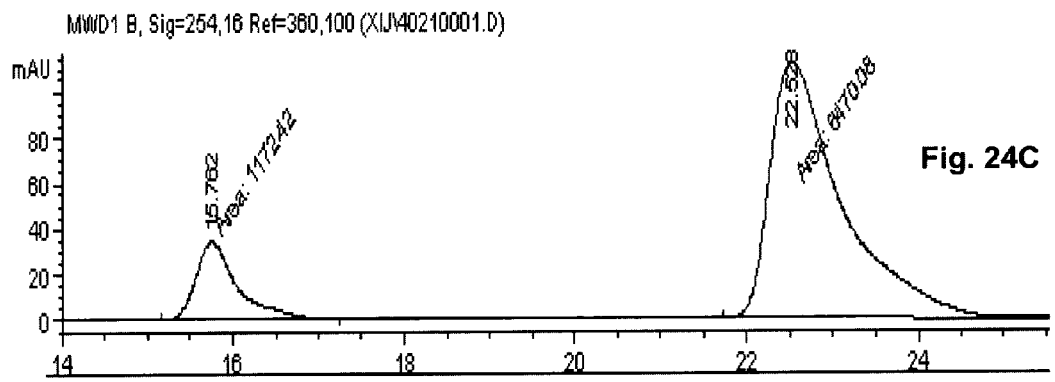
Fig. 24C
Fig. 24D
| Peak # | RetTime [min] | Type | Width [min] | Area [mAU*s] | Height [mAU] | Area % |
|---|---|---|---|---|---|---|
| 1 | 15.762 | MM | 0.5698 | 1172.42358 | 34.29093 | 15.3408 |
| 2 | 22.528 | MM | 0.9628 | 6470.07617 | 112.00441 | 84.6592 |
Totals : 7642.49976  146.29534
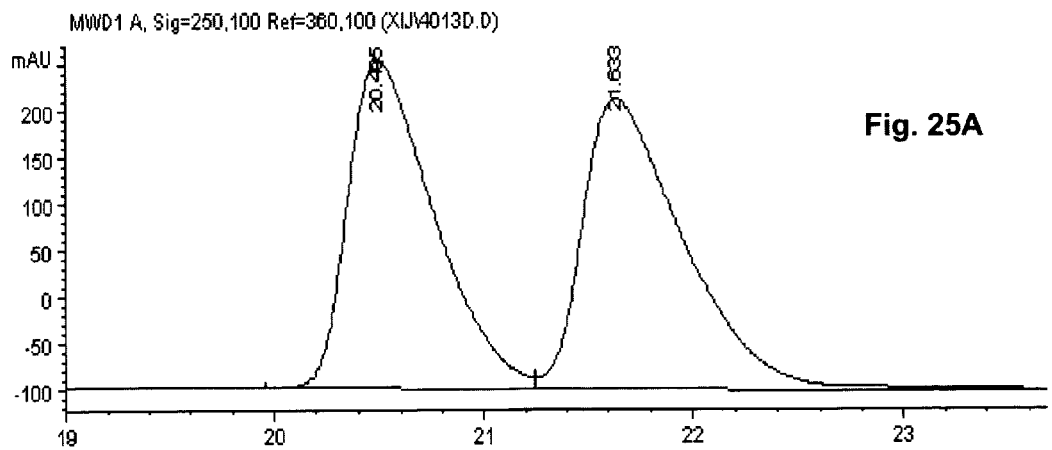
Fig. 25A

Fig. 25B
```
Peak RetTime Type  Width     Area       Height     Area
 #   [min]         [min]     [mAU*s]    [mAU]       %
----|-------|----|-------|----------|----------|--------|
  1  20.495  BV   0.4338  1.00781e4   352.21884  48.9305
  2  21.633  VP   0.5050  1.05187e4   312.25781  51.0695
Totals :                  2.05969e4   664.47665
```
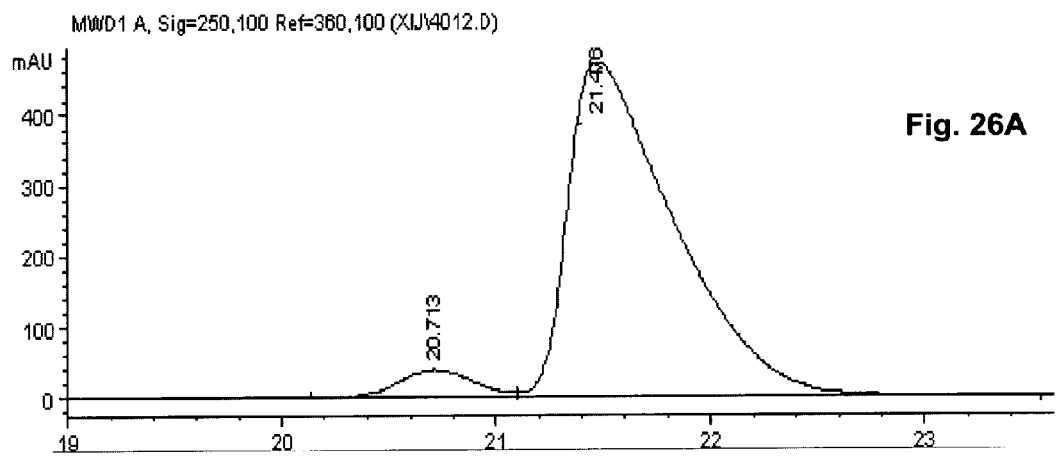
Fig. 26A
Fig. 26B
```
Peak RetTime Type  Width     Area       Height     Area
 #   [min]         [min]     [mAU*s]    [mAU]       %
----|-------|----|-------|----------|----------|--------|
  1  20.713  VV   0.3898   980.59454   39.48236   5.6858
  2  21.476  VB   0.5068  1.62657e4   473.49759  94.3142
Totals :                  1.72463e4   512.97995
```
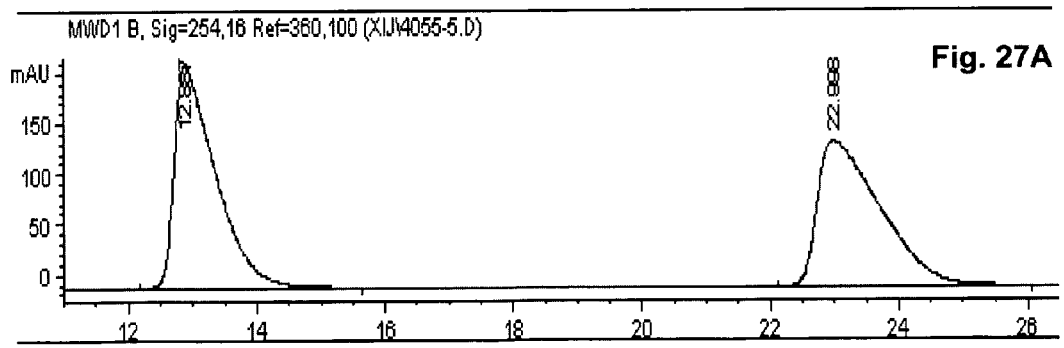
Fig. 27A Fig. 27B
```
Peak RetTime Type  Width     Area       Height      Area
 #   [min]        [min]     [mAU*s]    [mAU]        %
----|-------|----|-------|----------|----------|--------|
  1  12.887 BB   0.6461  1.00125e4   222.02794   49.9770
  2  22.998 BB   1.0194  1.00217e4   145.52457   50.0230
Totals :                 2.00342e4   367.55251
```
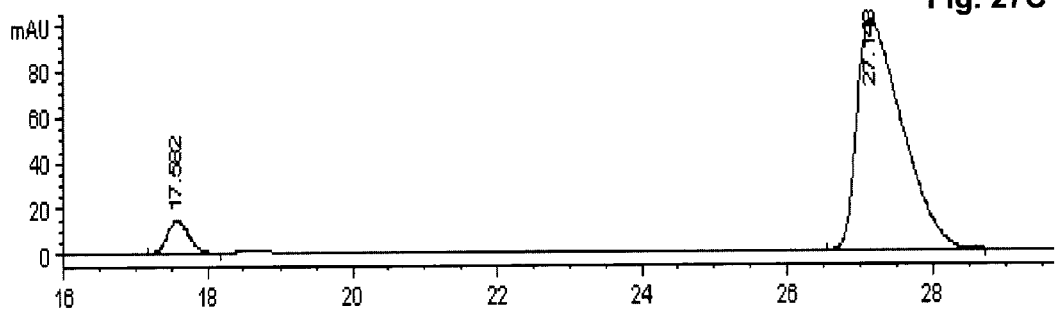
Fig. 27C
Fig. 27D
```
Peak RetTime Type  Width     Area       Height      Area
 #   [min]        [min]     [mAU*s]    [mAU]        %
----|-------|----|-------|----------|----------|--------|
  1  17.582 BB   0.3293   315.22769   14.75312    6.7544
  2  27.143 BB   0.6577  4351.79395  100.80508   93.2456
Totals :                 4667.02164  115.55820
```
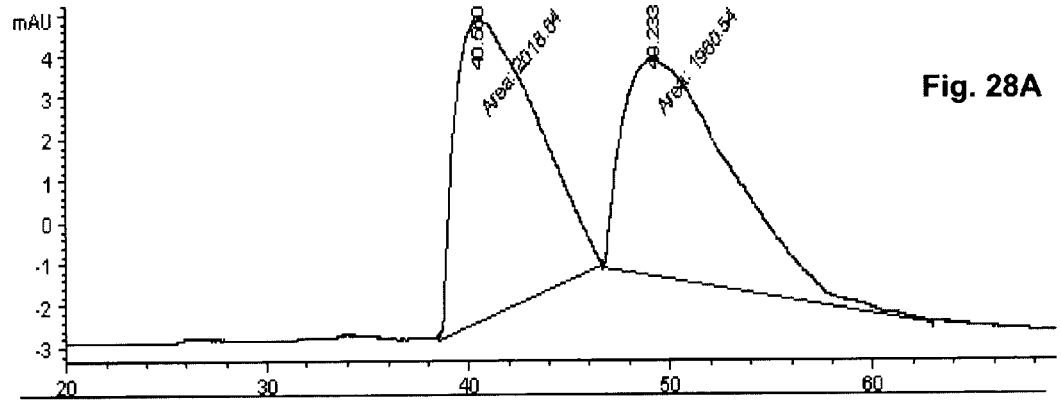
Fig. 28A
```
Peak RetTime Type  Width     Area       Height      Area
 #   [min]        [min]     [mAU*s]    [mAU]        %
----|-------|----|-------|----------|----------|--------|
  1  40.560 MM   4.6565  2018.64404    7.22515   50.7301
  2  49.233 MM   6.3145  1960.54309    5.17473   49.2699
Totals :                 3979.18713   12.39987
```
Fig. 28B

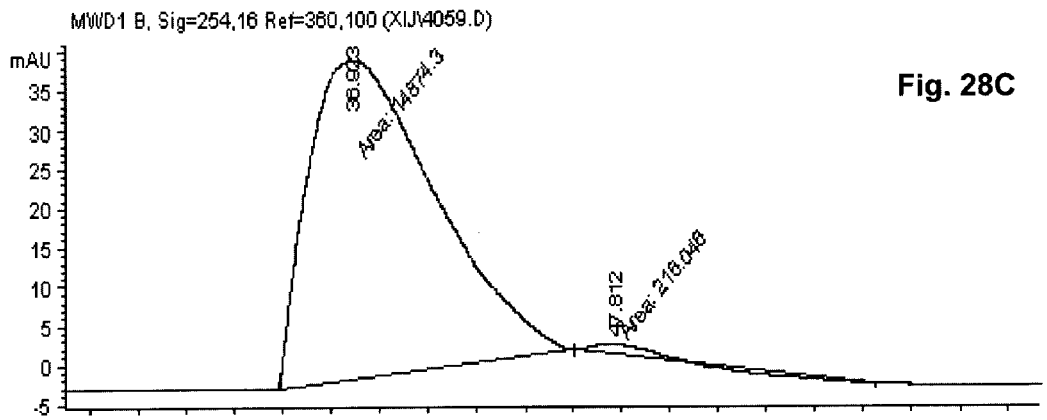
Fig. 28C
```
Peak RetTime Type  Width     Area       Height    Area
  #   [min]        [min]    [mAU*s]     [mAU]      %
----|-------|----|-------|-----------|-----------|--------|
  1  36.923 MM   4.2583  1.48743e4    40.88338  98.5683
  2  47.812 MM   2.7356   216.04626    1.31627   1.4317
Totals :                  1.50904e4    42.19965
```
Fig. 28D
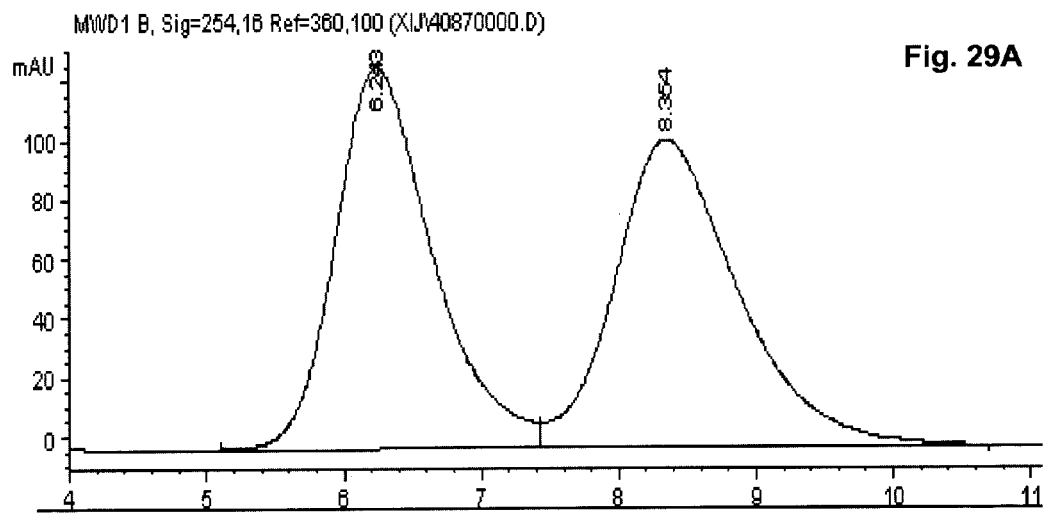
Fig. 29A
```
Peak RetTime Type  Width     Area       Height    Area
  #   [min]        [min]    [mAU*s]     [mAU]      %
----|-------|----|-------|-----------|-----------|--------|
  1   6.243 BV   0.7385  6277.34180  127.91251  49.4684
  2   8.354 VB   0.9268  6412.24951  103.22006  50.5316
Totals :                  1.26896e4   231.13258
```
Fig. 29B

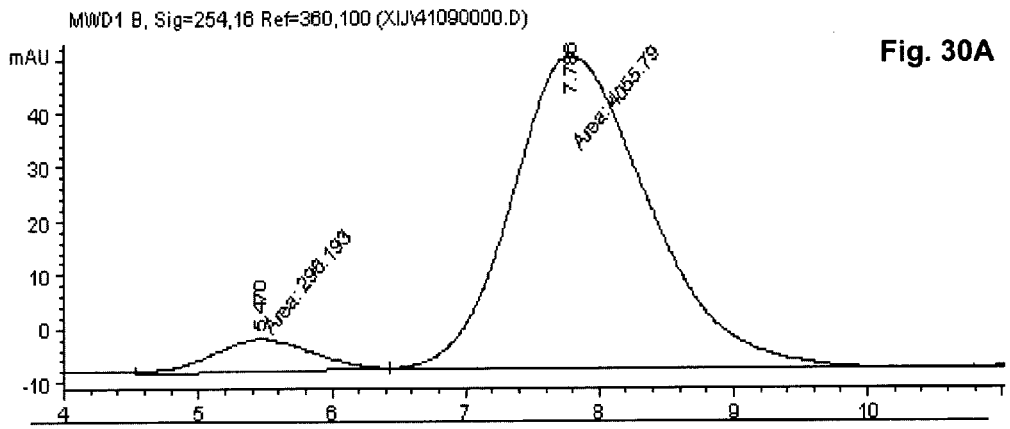
Fig. 30A
| Peak # | RetTime [min] | Type | Width [min] | Area [mAU*s] | Height [mAU] | Area % |
|---|---|---|---|---|---|---|
| 1 | 5.470 | MM | 0.8345 | 296.19272 | 5.91542 | 6.8059 |
| 2 | 7.786 | MM | 1.1686 | 4055.78931 | 57.84340 | 93.1941 |
| Totals : | | | | 4351.98203 | 63.75881 | |
Fig. 30B
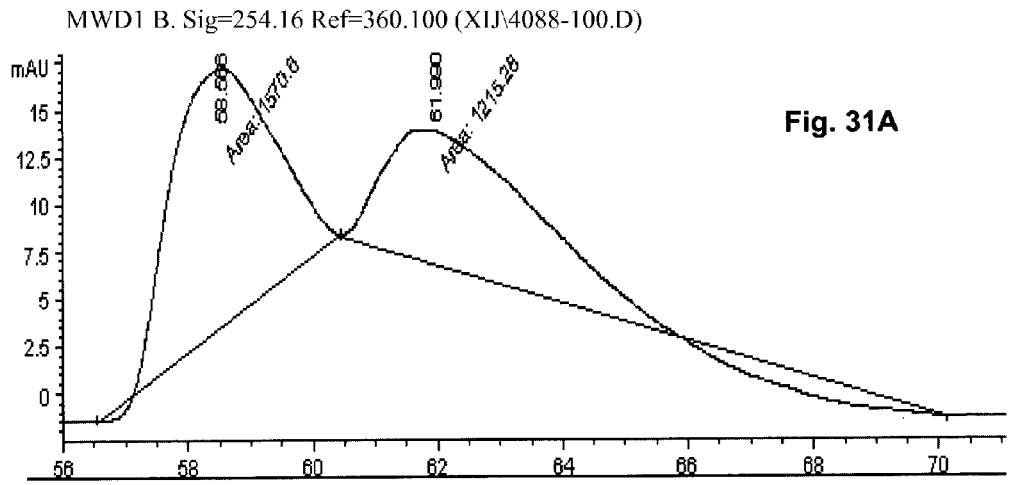
Fig. 31A
| Peak # | RetTime [min] | Type | Width [min] | Area [mAU*s] | Height [mAU] | Area % |
|---|---|---|---|---|---|---|
| 1 | 58.566 | MM | 1.4319 | 1570.59705 | 13.64452 | 56.3771 |
| 2 | 61.990 | MM | 2.8815 | 1215.27917 | 7.02910 | 43.6229 |
| Totals : | | | | 2785.87622 | 20.67362 | |
Fig. 31B

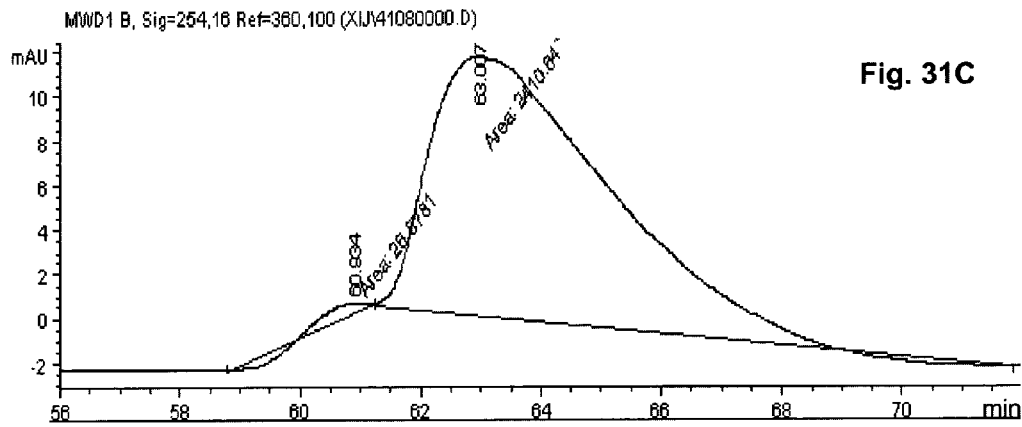
Fig. 31C
Fig. 31D
```
Peak RetTime Type  Width     Area       Height      Area
 #   [min]         [min]     [mAU*s]    [mAU]        %
----|-------|----|-------|----------|----------|--------|
  1  60.934 MM   1.1566    26.87814  3.87313e-1   1.1027
  2  63.007 MM   3.4503  2410.64160  11.64453    98.8973
Totals :                 2437.51974  12.03184
```
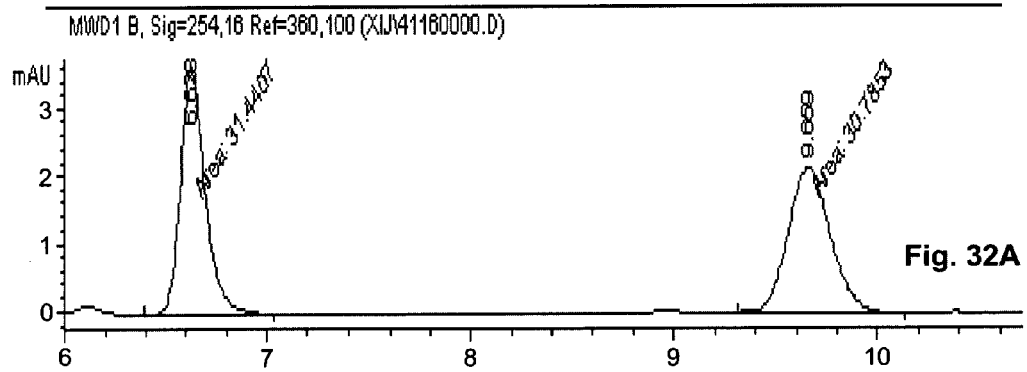
Fig. 32A
```
Peak RetTime Type  Width    Area      Height    Area
 #   [min]         [min]    [mAU*s]   [mAU]      %
----|-------|----|-------|----------|----------|--------|
  1   6.628 MM   0.1435   31.44070   3.65059  50.5266
  2   9.659 MM   0.2405   30.78528   2.13332  49.4734
Totals :                  62.22598   5.78390
```
Fig. 32B

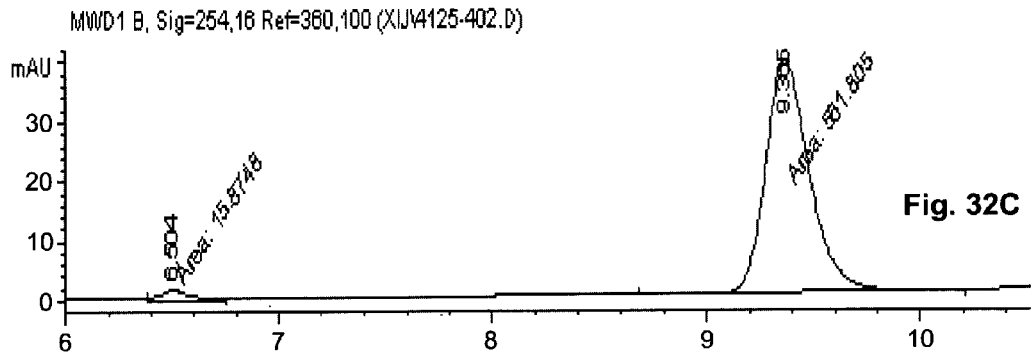
Fig. 32C
| Peak # | RetTime [min] | Type | Width [min] | Area [mAU*s] | Height [mAU] | Area % |
|---|---|---|---|---|---|---|
| 1 | 6.504 | MM | 0.1612 | 15.87481 | 1.64112 | 2.7480 |
| 2 | 9.365 | MM | 0.2389 | 561.80481 | 39.19201 | 97.2520 |
Totals : 577.67962 40.83313
Fig. 32D
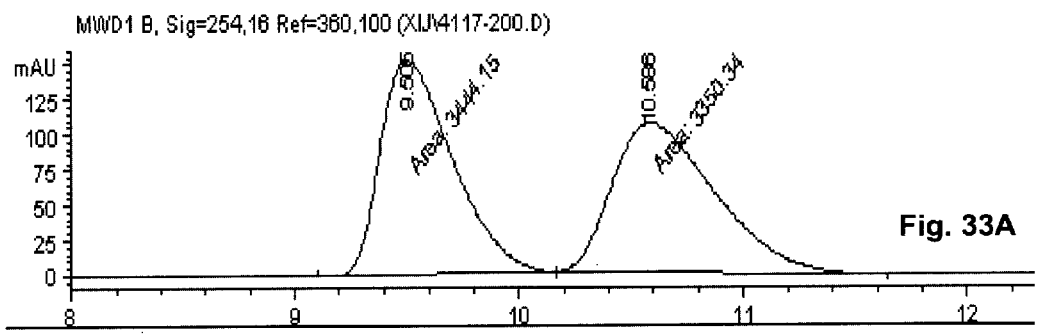
Fig. 33A
| Peak # | RetTime [min] | Type | Width [min] | Area [mAU*s] | Height [mAU] | Area % |
|---|---|---|---|---|---|---|
| 1 | 9.505 | MM | 0.3755 | 3444.14771 | 152.86559 | 50.6903 |
| 2 | 10.586 | MM | 0.5267 | 3350.33813 | 106.01103 | 49.3097 |
Totals : 6794.48584 258.87662
Fig. 33B
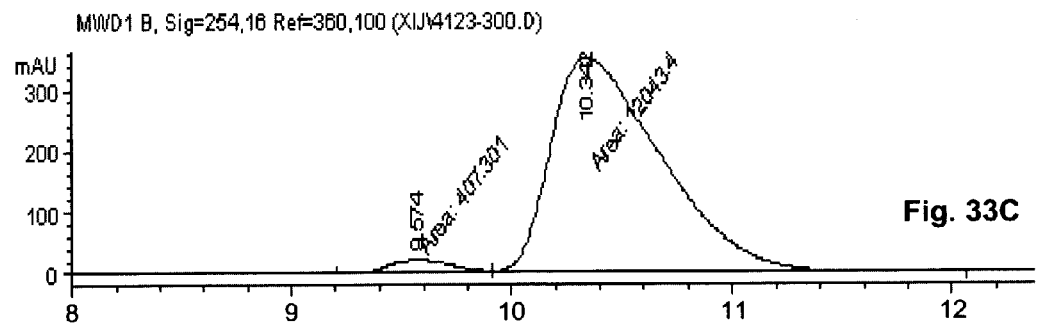
Fig. 33C Fig. 33D
```
Peak RetTime Type  Width     Area       Height     Area
 #   [min]         [min]     [mAU*s]    [mAU]      %
----|---------|----|--------|----------|----------|--------|
  1   9.574   MM   0.3200   407.30142   21.21614   3.2713
  2  10.342   MM   0.5756   1.20434e4  348.73599  96.7287
Totals :                    1.24507e4  369.95213
```
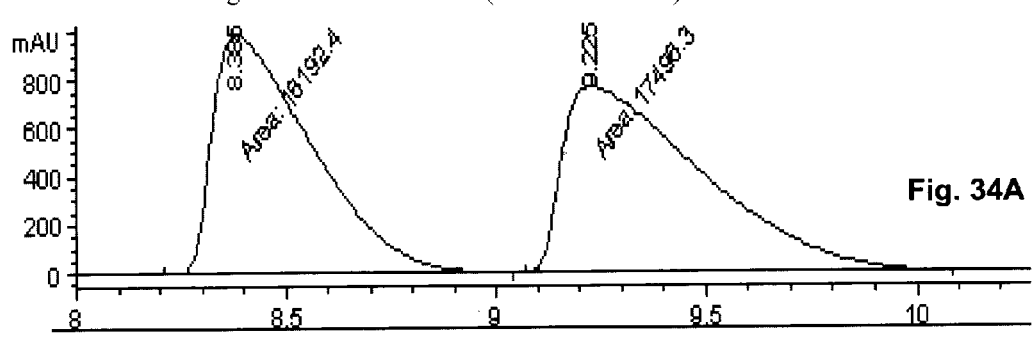
Fig. 34A
```
Peak RetTime Type  Width     Area       Height     Area
 #   [min]         [min]     [mAU*s]    [mAU]      %
----|---------|----|--------|----------|----------|--------|
  1   8.385   MM   0.2718   1.61924e4  992.88800  48.0647
  2   9.225   MM   0.3803   1.74963e4  766.82971  51.9353
Totals :                    3.36887e4 1759.71771
```
Fig. 34B
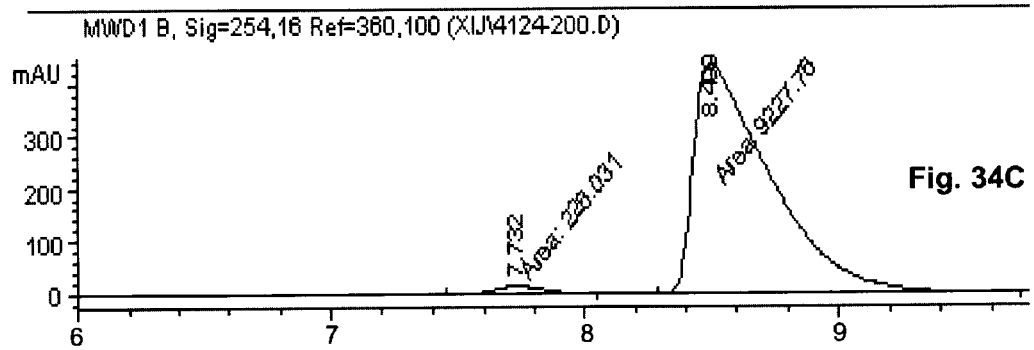
Fig. 34C
```
Peak RetTime Type  Width     Area       Height     Area
 #   [min]         [min]     [mAU*s]    [mAU]      %
----|---------|----|--------|----------|----------|--------|
  1   7.732   MM   0.2474   226.03139   15.22993   2.3909
  2   8.499   MM   0.3492  9227.76465  440.42603  97.6091
Totals :                   9453.79604  455.65595
```
Fig. 34D

TRICYCLIC CHIRAL COMPOUNDS AND THEIR USE IN ASYMMETRIC CATALYSIS

CROSS-REFERENCE TO RELATED APPLICATIONS

This application makes reference to and claims the benefit of priority of an application for "Novel Tricyclic Chiral Ligands" filed on Sep. 3, 2008 with the United States Patent and Trademark Office, and there duly assigned Ser. No. 61/093,843. The contents of said application filed on Sep. 3, 2008 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to novel tricyclic chiral compounds and their use in asymmetric catalysis. The tricyclic chiral compounds have a hexahydropyrrolo[2,3-b]-indole skeleton.

BACKGROUND

Driven by the ever-increasing demand for chiral chemicals, the development of new and efficient methods to provide enantioenriched products is of great interest to both academia and industry. Catalytic asymmetric reactions using organocatalysts provide one of the most powerful and economical synthetic approaches to a variety of enantiomerically enriched compounds. The development of new privileged chiral ligands and catalysts that exhibit high reactivity and enantioselectivity is always a challenging endeavour for an organic chemist. State-of-the-art chiral ligands generally come from the profound understanding of catalytic process, the creativity of organic chemists and sometimes, a degree of serendipity. The most important feature of privileged chiral catalysts is the highly rigid structures, with multiple oxygen-, nitrogen-, or phosphorous-containing functional groups to bind strongly to reactive metal centers [e.g. Yoon, T P, & Jacobsen, E N, *Science* (2003) 299, 1691-1693 or Pfaltz, A, & Drury III, W J, *PNAS* (2004) 101, 5723-5726]. Another important point is that it should be easily prepared and modified, thus fit well to a combinatorial approach for finding the most suitable ligand for a particular catalytic asymmetric transformation. A compound that has been ascribed as a "universal catalyst" due to its widespread application in organocatalysis is proline. However, it is widely accepted that proline is usually not an efficient catalyst in terms of yield and enantioselectivity for electrophiles that are poor hydrogen bond acceptors such as nitroalkenes.

Unfortunately, with most organocatalysts for asymmetric catalysis the use of high catalytic loading (>10 mol %), the need to use anhydrous organic solvents or/and the narrow substrate scope limit their applicability to complex molecule synthesis. Furthermore, the organocatalyzed functionalization of biomolecules in water remains a challenge.

Therefore, there remains a need for novel organocatalysts. It would also be particularly useful to provide an organocatalyst which can work nicely in both water and organic solvents.

SUMMARY OF THE INVENTION

The invention relates to a novel class of structurally rigid tricyclic chiral compounds based on hexahydropyrrolo[2,3-b]indole skeleton which can be synthesized from a L-tryptophan derivative in five steps. The ligands can be used for example as an efficient chiral ligand in the enantioselective borane reduction of prochiral ketones to afford the corresponding alcohols in excellent yield and high enantioselectivities, or in enatioselective carbon-carbon bond formation.

In a first aspect the invention provides a hexahydropyrrolo [2,3-b]indole compound of Formula (XX):

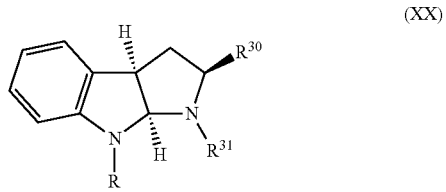

(XX)

In Formula (XX) R is one of —$COOR^3$, —$R^4COOR^3$, —$R^4CHO$, —$R^4COR^3$, —$R^4CONR^5R^6$, —$R^4COX$, —$R^4OP(=O)(OH)_2$, —$R^4P(=O)(OH)_2$), $R^4C(O)C(R^3)CR^5R^6$, —$R^4CO_2COR^3$ and $(R^3CO)_2O$. $R^{31}$ is one of hydrogen, —$COOR^3$, —$R^4COOR^3$, —$R^4CHO$, —$R^4COR^3$, —$R^4CONR^5R^6$, —$R^4COX$, —$R^4OP(=O)(OH)_2$, —$R^4P(=O)(OH)_2$), —$R^4C(O)C(R^3)CR^5R^6$, —$R^4CO_2COR^3$ and $(R^3CO)_2O$. $R^3$, $R^5$ and $R^6$ are independent from one another one of hydrogen, an aliphatic group with a main chain having 1 to about 20 carbon atoms, an alicyclic group, an aromatic group, an arylaliphatic group and an arylalicyclic group, comprising 0 to about 3 heteroatoms. The heteroatoms are independently selected from N, O, S, Se and Si. $R^4$ is one of an aliphatic bridge with a main chain having 1 to about 20 carbon atoms, an alicyclic bridge, an aromatic bridge, an arylaliphatic bridge and an arylalicyclic bridge, comprising 0 to about 3 heteroatoms. The heteroatoms are independently selected from N, O, S, Se and Si, X is halogen. Further, in Formula (XX) $R^{30}$ is one of —$C(OH)R^1R^2$ and —$COOR^{14}$. $R^1$, $R^2$ and $R^{14}$ are independent from one another one of hydrogen, an aliphatic group with a main chain having 1 to about 20 carbon atoms, an alicyclic group, an aromatic group, an arylaliphatic group and an arylalicyclic group, comprising 0 to about 3 heteroatoms. The heteroatoms are independently selected from N, O, S, Se and Si.

In a second aspect the invention provides a hexahydropyrrolo[2,3-b]indole compound of Formula (VII):

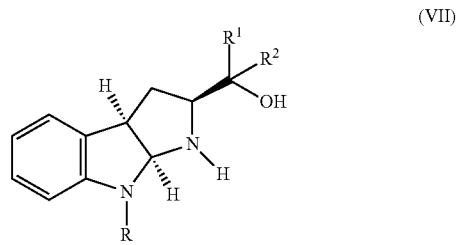

(VII)

In Formula (VII) R is one of —$COOR^3$, —$R^4COOR^3$, —$R^4CHO$, —$R^4COR^3$, —$R^4CONR^5R^6$, —$R^4COX$, —$R^4OP(=O)(OH)_2$, —$R^4P(=O)(OH)_2$), —$R^4C(O)C(R^3)CR^5R^6$, —$R^4CO_2COR^3$ and —$(R^3CO)_2O$. $R^3$ is one of hydrogen, $(C_1-C_{20})$-alkyl, alkenyl, alkynyl, cycloalkyl, cycloalkenyl, cycloalkylalkyl, aryl, alkylaryl, and arylalkyl. $R^4$ is one of hydrogen, $(C_1-C_{20})$-alkyl, alkenyl, alkynyl, cycloalkyl, cycloalkenyl, cycloalkylalkyl, aryl, alkylaryl, and arylalkyl. $R^5$ is one of hydrogen, $(C_1-C_{20})$-alkyl, alkenyl, alkynyl, cycloalkyl, cycloalkenyl, cycloalkylalkyl, aryl, alkylaryl, and arylalkyl. $R^6$ is one of hydrogen, $(C_1-C_{20})$-alkyl, alkenyl, alkynyl, cycloalkyl, cycloalkenyl, cycloalkylalkyl, aryl, alkylaryl, and arylalkyl. X is halogen. In some embodiments $R^3$ to $R^6$ are independent from one another one of hydrogen, $(C_1-C_{10})$ alkyl, $(C_3-C_8)$ cycloalkyl, $(C_1-C_3)$ alkylaryl, arylalkyl, where the alkyl radicals, may be substituted by one or more substituents, for example, —OH, —O—$(C_1-C_{10})$-alkyl, —O-phenyl, —O—CO—$(C_1-C_{10})$-alkyl, —O—CO-aryl, —CO—$(C_1-C_5)$-alkyl, —CO—O—$(C_1-C_5)$-alkyl, —CO—O-aryl, and aryl. Further, in Formula (VII) $R^1$ is independently selected from hydrogen, $(C_1-C_{20})$-alkyl, aryl, alkenyl, alkynyl, cycloalkyl, cycloalkenyl, cycloalkylalkyl, alkylaryl, and arylalkyl heteroaryl. Alkyl, alkenyl or alkynyl can be straight chained or branched, and may be substituted by one or more substituents. $R^2$ in Formula (VII) is independently selected from hydrogen, $(C_1-C_{20})$-alkyl, aryl, alkenyl, alkynyl, cycloalkyl, cycloalkenyl, cycloalkylalkyl, alkylaryl, arylalkyl, and heteroaryl. Alkyl, alkenyl or alkynyl can be straight chained or branched, and may be substituted by one or more substituents. $R^1$ and $R^2$ may in some embodiments be independent from one another one of hydrogen, $(C_1-C_{10})$-alkyl, $(C_3-C_8)$ cycloalkyl, $(C_1-C_3)$ alkylaryl, arylalkyl aryl, or heteroaryl. Again, the alkyl radicals, may be branched and substituted by one or more substituents, for example by —OH, —O—$(C_1-C_{10})$-alkyl, —O-phenyl, —O—CO—$(C_1-C_{10})$-alkyl, —CO—O—$(C_1-C_8)$-alkyl, —CO—O-aryl.

In a third aspect the invention provides a hexahydropyrrolo[2,3-b]indole compound of Formula (VIII):

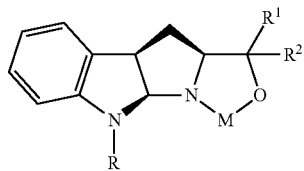

(VIII)

The compound of Formula (VIII) has a bowl-shaped conformation. In Formula (VIII) M is a metal selected from the group consisting of Group 1 to Group 14 metals, lanthanides and actinides. Further, in Formula (VIII) the moiety R is one of $COOR^3$, $R^3COOR^4$, $R^3CHO$, $R^3COR^4$, $R^3CONR^4R^5$, $R^3COX$, $R^3OP(=O)(OH)_2$, $R^3P(=O)(OH)_2$), $R^3C(O)C(R^4)CR^5R^6$, —$R^4CO_2COR^3$ and $(R^3CO)_2O$. $R^3$ is one of hydrogen, $(C_1-C_{20})$-alkyl, alkenyl, alkynyl, cycloalkyl, cycloalkenyl, cycloalkylalkyl, aryl, alkylaryl, or arylalkyl. $R^4$ is one of hydrogen, $(C_1-C_{20})$-alkyl, alkenyl, alkynyl, cycloalkyl, cycloalkenyl, cycloalkylalkyl, aryl, alkylaryl, and arylalkyl. $R^5$ is one of hydrogen, $(C_1-C_{20})$-alkyl, alkenyl, alkynyl, cycloalkyl, cycloalkenyl, cycloalkylalkyl, aryl, alkylaryl, or arylalkyl. $R^6$ is one of hydrogen, $(C_1-C_{20})$-alkyl, alkynyl, cycloalkyl, cycloalkenyl, cycloalkylalkyl, aryl, alkylaryl, and arylalkyl. X is halogen. Further, in Formula (VIII) $R^1$ is independently selected from hydrogen, $(C_1-C_{20})$-alkyl, aryl, alkenyl, alkynyl, cycloalkyl, cycloalkenyl, cycloalkylalkyl, alkylaryl, and arylalkyl heteroaryl. Alkyl, alkenyl or alkynyl can be straight chained or branched, and may be substituted by one or more substituents. $R^2$ in Formula (VIII) is independently selected from hydrogen, $(C_1-C_{20})$-alkyl, aryl, alkenyl, alkynyl, cycloalkyl, cycloalkenyl, cycloalkylalkyl, alkylaryl, arylalkyl, and heteroaryl. Alkyl, alkenyl or alkynyl can be straight chained or branched, and may be substituted by one or more substituents.

In a fourth aspect the invention provides a hexahydropyrrolo[2,3-b]indole compound of Formula (IX):

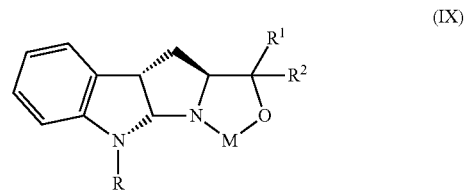

(IX)

The compound of Formula (IX) has an S-shaped conformation. In Formula (IX) M is a metal selected from the group consisting of Group 1 to Group 14 metals, lanthanides and actinides. Further, in Formula (IX) R is one of $COOR^3$, $R^3COOR^4$, $R^3CHO$, $R^3COR^4$, $R^3CONR^4R^5$, $R^3COX$, $R^3OP(=O)(OH)_2$, $R^3P(=O)(OH)_2$) $R^3C(O)C(R^4)CR^5R^6$, —$R^4CO_2COR^3$ and $(R^3CO)_2O$. $R^3$ is one of hydrogen, $(C_1-C_{20})$-alkyl, alkenyl, alkynyl, cycloalkyl, cycloalkenyl, cycloalkylalkyl, aryl, alkylaryl, or arylalkyl. $R^4$ is one of hydrogen, $(C_1-C_{20})$-alkyl, alkenyl, alkynyl, cycloalkyl, cycloalkenyl, cycloalkylalkyl, aryl, alkylaryl, and arylalkyl. $R^5$ is one of hydrogen, $(C_1-C_{20})$-alkyl, alkenyl, alkynyl, cycloalkyl, cycloalkenyl, cycloalkylalkyl, aryl, alkylaryl, or arylalkyl. $R^6$ is one of hydrogen, $(C_1-C_{20})$-alkyl, alkenyl, alkynyl, cycloalkyl, cycloalkenyl, cycloalkylalkyl, aryl, alkylaryl, and arylalkyl. X is halogen. Further, in Formula (IX) $R^1$ is independently selected from hydrogen, $(C_1-C_{20})$-alkyl, aryl, alkenyl, alkynyl, cycloalkyl, cycloalkenyl, cycloalkylalkyl, alkylaryl, and arylalkyl heteroaryl. Alkyl, alkenyl or alkynyl can be straight chained or branched, and may be substituted by one or more substituents. $R^2$ in Formula (IX) is independently selected from hydrogen, $(C_1-C_{20})$-alkyl, aryl, alkenyl, alkynyl, cycloalkyl, cycloalkenyl, cycloalkylalkyl, alkylaryl, arylalkyl, and heteroaryl. Alkyl, alkenyl or alkynyl can be straight chained or branched, and may be substituted by one or more substituents.

In a fifth aspect the invention provides a hexahydropyrrolo[2,3-b]indole compound of Formula (VI):

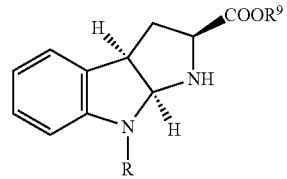

(VI)

In Formula (VI) R is one of $COOR^3$, $R^3COOR^4$, $R^3CHO$, $R^3COR^4$, $R^3CONR^4R^5$, $R^3COX$, $R^3OP(=O)(OH)_2$, $R^3P(=O)(OH)_2$) $R^3C(O)C(R^4)CR^5R^6$, —$R^4CO_2COR^3$ and $(R^3CO)_2O$. $R^3$ is one of hydrogen, $(C_1-C_{20})$-alkyl, alkenyl, alkynyl, cycloalkyl, cycloalkenyl, cycloalkylalkyl, aryl, alkylaryl, or arylalkyl. $R^4$ is one of hydrogen, $(C_1-C_{20})$-alkyl, alkenyl, alkynyl, cycloalkyl, cycloalkenyl, cycloalkylalkyl, aryl, alkylaryl, and arylalkyl. $R^5$ is one of hydrogen, $(C_1-C_{20})$-alkyl, alkenyl, alkynyl, cycloalkyl, cycloalkenyl, cycloalkylalkyl, aryl, alkylaryl, or arylalkyl. $R^6$ is one of hydrogen, $(C_1-C_{20})$-alkyl, alkenyl, alkynyl, cycloalkyl, cycloalkenyl, cycloalkylalkyl, aryl, alkylaryl, and arylalkyl. X is halogen. $R^9$ in Formula (VI) is alkyl.

In a sixth aspect the invention provides a hexahydropyrrolo[2,3-b]indole compound of Formula (IV):

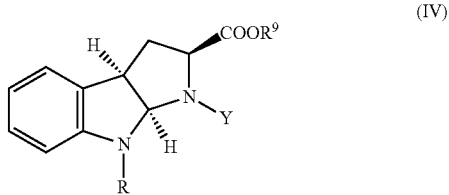

(IV)

In Formula (IV) R is one of COOR³, R³COOR⁴, R³CHO, R³COR⁴, R³CONR⁴R⁵, R³COX, R³OP(=O)(OH)₂, R³P(=O)(OH)₂) R³C(O)C(R⁴)CR⁵R⁶, —R⁴CO₂COR³ and (R³CO)₂O. R³ is one of hydrogen, ($C_1$-$C_{20}$)-alkyl, alkenyl, alkynyl, cycloalkyl, cycloalkenyl, cycloalkylalkyl, aryl, alkylaryl, or arylalkyl. R⁴ is one of hydrogen, ($C_1$-$C_{20}$)-alkyl, alkenyl, alkynyl, cycloalkyl, cycloalkenyl, cycloalkylalkyl, aryl, alkylaryl, and arylalkyl. R⁵ is one of hydrogen, ($C_1$-$C_{20}$)-alkyl, alkenyl, alkynyl, cycloalkyl, cycloalkenyl, cycloalkylalkyl, aryl, alkylaryl, or arylalkyl. R⁶ is one of hydrogen, ($C_1$-$C_{20}$)-alkyl, alkenyl, alkynyl, cycloalkyl, cycloalkenyl, cycloalkylalkyl, aryl, alkylaryl, and arylalkyl. X is halogen. Y in Formula (IV) is a nitrogen protecting group. R⁹ in Formula (IV) is alkyl.

In a seventh aspect the invention provides a hexahydropyrrolo[2,3-b]indole compound of Formula (IVA):

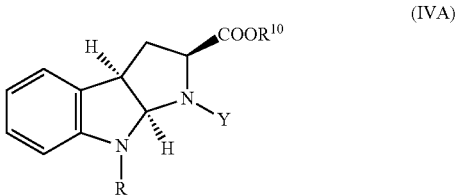

(IVA)

In Formula (IVA) R is one of COOR³, R³COOR⁴, R³CHO, R³COR⁴, R³CONR⁴R⁵, R³COX, R³OP(=O)(OH)₂, R³P(=O)(OH)₂) R³C(O)C(R⁴)CR⁵R⁶, —R⁴CO₂COR³ and (R³CO)₂O. R³ is one of hydrogen, ($C_1$-$C_{20}$)-alkyl, alkenyl, alkynyl, cycloalkyl, cycloalkenyl, cycloalkylalkyl, aryl, alkylaryl, or arylalkyl. R⁴ is one of hydrogen, ($C_1$-$C_{20}$)-alkyl, alkenyl, alkynyl, cycloalkyl, cycloalkenyl, cycloalkylalkyl, aryl, alkylaryl, and arylalkyl. R⁵ is one of hydrogen, ($C_1$-$C_{20}$)-alkyl, alkenyl, alkynyl, cycloalkyl, cycloalkenyl, cycloalkylalkyl, aryl, alkylaryl, or arylalkyl. R⁶ is one of hydrogen, ($C_1$-$C_{20}$)-alkyl, alkenyl, alkynyl, cycloalkyl, cycloalkenyl, cycloalkylalkyl, aryl, alkylaryl, and arylalkyl. X is halogen. Y in Formula (IVA) is a nitrogen protecting group. R¹⁶ in Formula (IVA) is a protecting group that may be removable by hydrogenolysis, e.g. aryl-methylenyl.

In an eighth aspect the invention provides a hexahydropyrrolo[2,3-b]indole compound of Formula (VIA):

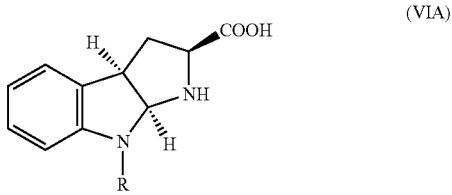

(VIA)

In Formula (VIA) R is one of COOR³, R³COOR⁴, R³CHO, R³COR⁴, R³CONR⁴R⁵, R³COX, R³OP(=O)(OH)₂, R³P(=O)(OH)₂) R³C(O)C(R⁴)CR⁵R⁶, —R⁴CO₂COR³ and (R³CO)₂O. R³ is one of hydrogen, ($C_1$-$C_{20}$)-alkyl, alkenyl, alkynyl, cycloalkyl, cycloalkenyl, cycloalkylalkyl, aryl, alkylaryl, or arylalkyl. R⁴ is one of hydrogen, ($C_1$-$C_{20}$)-alkyl, alkenyl, alkynyl, cycloalkyl, cycloalkenyl, cycloalkylalkyl, aryl, alkylaryl, and arylalkyl. R⁵ is one of hydrogen, ($C_1$-$C_{20}$)-alkyl, alkenyl, alkynyl, cycloalkyl, cycloalkenyl, cycloalkylalkyl, aryl, alkylaryl, or arylalkyl. R⁶ is one of hydrogen, ($C_1$-$C_{20}$)-alkyl, alkenyl, alkynyl, cycloalkyl, cycloalkenyl, cycloalkylalkyl, aryl, alkylaryl, and arylalkyl. X is halogen.

In a ninth aspect the invention provides a method of preparing a compound of Formula (VI) according to the fifth aspect (supra). The method includes providing a compound of Formula (IV) according to the sixth aspect (supra). Moiety Y in the compound of Formula (VI) is generally cleavable via hydrogenolysis. The method includes exposing the compound of Formula (IV) to H₂ in the presence of a Pd/C catalyst. Thereby the method includes allowing deprotection of the Nα group of compound (IV).

In a tenth aspect the invention provides a method of preparing a compound of Formula (VIA) according to the eighth aspect (supra). The method includes providing a compound of Formula (IV A) according to the seventh aspect (supra). As said above, generally (but not necessarily) moiety Y in the compound of Formula (IVA) is cleavable via hydrogenolysis. The method further includes exposing the compound of Formula (IVA) to H₂ in the presence of a Pd/C catalyst. Thereby the method firstly includes allowing deprotection of the Nα group of compound (IVA). The method thereby secondly also includes allowing the cleavage of the ester bond to moiety R¹⁰ of compound IVA).

In an eleventh aspect the invention provides a method of preparing a compound of Formula (VII) according to the second aspect (supra). The method includes reacting a compound of Formula (VI) according to the fifth aspect (supra) with a compound R¹MgX, R²MgX or a mixture of R¹MgX and R²MgX. R¹ in R¹MgX is independently selected from hydrogen, ($C_1$-$C_{20}$)-alkyl, aryl, alkenyl, alkynyl, cycloalkyl, cycloalkenyl, cycloalkylalkyl, alkylaryl, and arylalkyl heteroaryl. R² in R²MgX is independently selected from hydrogen, ($C_1$-$C_{20}$)-alkyl, aryl, alkenyl, alkynyl, cycloalkyl, cycloalkenyl, cycloalkylalkyl, alkylaryl, arylalkyl, and heteroaryl.

In a twelfth aspect the invention provides a method of preparing a compound of Formula (IV) according to the sixth aspect (supra). The method includes contacting a hexahydropyrrolo[2,3-b]indole compound of Formula (III)

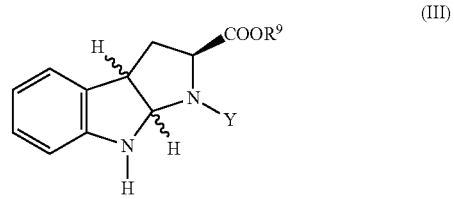

(III)

with an acyl halide RCOX in the presence of a base. In Formula (III) Y is a nitrogen protecting group, and R⁹ is alkyl.

In a thirteenth aspect the invention provides a method of preparing a compound of Formula (IVA) according to the seventh aspect (supra). The method includes contacting a hexahydropyrrolo[2,3-b]indole compound of Formula (IIIA)

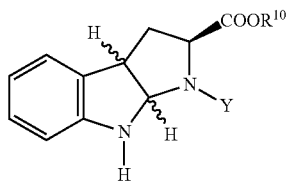

(IIIA)

with an acyl halide RCOX in the presence of a base. In Formula (IIIA) Y is a nitrogen protecting group, and $R^{19}$ is aryl-methylenyl.

In a fourteenth aspect the invention provides a method of preparing a compound of Formula (VIII) according to the third aspect (supra). The method includes reacting a compound of Formula (VII) according to the second aspect with a metal compound selected from the group consisting of Group 1 to Group 14 metals, lanthanides and actinides.

In a fifteenth aspect the invention provides a method of preparing a compound of Formula (IX) according to the fourth aspect (supra). The method includes reacting a compound of Formula (VII) according to the second aspect with a metal compound selected from the group consisting of Group 1 to Group 14 metals, lanthanides and actinides.

In a sixteenth aspect the invention provides the use of the compound of Formulas (VII), (VIII), (IX), (IV) and (VI) according to the second to the sixth aspects as a ligand for asymmetric catalysis.

In a seventeenth aspect the invention provides the use of the compound of Formula (VIA) according to the nineth aspect (supra) as a ligand for asymmetric catalysis.

BRIEF DESCRIPTION OF THE DRAWINGS

The invention will be better understood with reference to the detailed description when considered in conjunction with the non-limiting examples and the accompanying drawings.

FIG. 13A depicts exemplary catalysts used in the asymmetric Michael reaction of propanal to nitroalkenes depicted in the scheme of FIG. 13B. FIG. 13C is a table depicting exemplary data on the catalytic asymmetric Michael addition of FIG. 13B. Reactions were conducted with 2 equiv of aldehyde, 1 equiv of nitrostyene at room temperature in the presence of catalyst with 1:1 catalyst:DMAP. $^a$ Isolated yield. $^b$ Dr (syn/anti) was determined by chiral HPLC analysis. $^c$ Reported values refer to the syn isomer and were determined by chiral HPLC on a chiral stationary phase.

FIG. 15 depicts schematically the preparation and characterization of exemplary chiral ligands of Formula VII, starting from a commercially available Nα-protected L-tryptophan (1) (cf. also FIG. 2).

FIG. 20 depicts chiral HPLC analysis of (R)-1-phenylethanol obtained using a catalyst of general Formula (VII) on a Dacicel Chiralcel OD column.

FIG. 21 depicts chiral HPLC analysis of (S)-2-Bromo-1-phenylethanol obtained using a catalyst of general Formula (VII) on a Dacicel Chiralcel OD column (FIG. 21C corresponding to FIG. 21A).

FIG. 22 depicts chiral HPLC analysis of (R)-1-(4-Bromophenyl)-ethanol obtained using a catalyst of general Formula (VII) on a Dacicel Chiralcel OB-H column (FIG. 22B corresponding to FIG. 22A and FIG. 22D corresponding to FIG. 22C).

FIG. 23 depicts chiral HPLC analysis of (R)-1-(2-Naphthyl)-ethanol obtained using a catalyst of general Formula (VII) on a Dacicel Chiralcel AS-H column column.

FIG. 24 depicts chiral HPLC analysis of (R)-1-(2-(6-methoxy)-Naphthyl)-ethanol obtained using a catalyst of general Formula (VII) on a Dacicel Chiralcel OD column.

FIG. 25 depicts chiral HPLC analysis of racemic 1-(4-Nitrophenyl)-ethanol on a Chiralcel OB-H column as a reference.

FIG. 26 depicts chiral HPLC analysis of (R)-1-(4-Nitrophenyl)-ethanol obtained using a catalyst of general Formula (VII) on a Chiralcel OB-H column.

FIG. 27 depicts chiral HPLC analysis of (R)-1-(3-fluorophenyl)-ethanol obtained using a catalyst of general Formula (VII) on a Chiralcel OB-H column.

FIG. 28 depicts chiral HPLC analysis of (R)-1-(4-Trifluoromethylphenyl)-ethanol obtained using a catalyst of general Formula (VII) on a Chiralcel OJ column.

FIG. 29 depicts chiral HPLC analysis of racemic 1-(3-Trifluoromethylphenyl)-ethanol obtained using a catalyst of general Formula (VII) on a Chiralcel OBH column as a reference (cf. FIG. 30).

FIG. 30 depicts chiral HPLC analysis of (R)-1-(3-Trifluoromethylphenyl)-ethanol obtained using a catalyst of general Formula (VII) on a Chiralcel OBH column.

FIG. 31 depicts chiral HPLC analysis of (R)-1-(4-methylsulfonylphenyl)ethanol obtained using a catalyst of general Formula (VII) on a Chiralcel OBH column.

FIG. 32 depicts chiral HPLC analysis of (R)-1-(3,5-difluorophenyl)ethanol obtained using a catalyst of general Formula (VII) on a Chiralcel OB-H column.

FIG. 33 depicts chiral HPLC analysis of (R)-3,5-bistrifluoromethylphenyl ethanol obtained using a catalyst of general Formula (VII) on a Chiralcel OB-H column.

FIG. 34 depicts chiral HPLC analysis of (R)-1-(3,4-difluorophenyl)ethanol obtained using a catalyst of general Formula (VII) on a Chiralcel OB-H column.

DETAILED DESCRIPTION OF INVENTION

The present invention relates to the design and synthesis of a series of a new class of structurally rigid tricyclic chiral ligands based on the hexahydropyrrolo[2,3-b]indole skeleton which can be synthesized from an L-tryptophan derivative in four and five steps, respectively.

Figure 6:
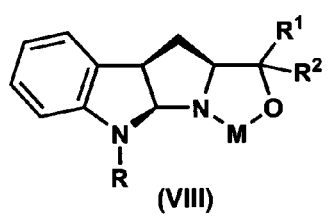
FIG. 6 depicts the two different isomers of metal complexes exemplified by a compound of Formula (VIII) with $R^1=R^2=ph$, and a compound of Formula (IX) together with a 3D model thereof.
Figure 6:
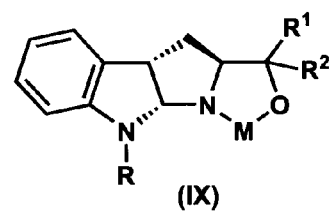
Figure 6:
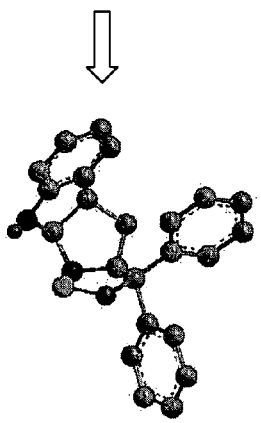
Figure 6:
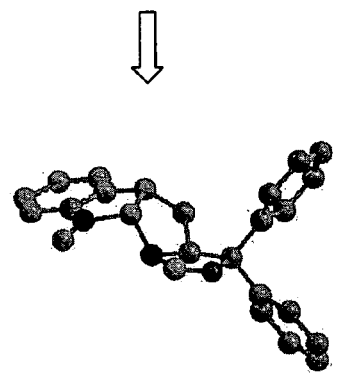

The invention is based on the identification of the tryptophan-based hexahydropyrrolo[2,3-b]indole skeleton as a rigid backbone that is capable for use to induce chirality. Two possible isomers, endo or exo isomer could be generated in the ring closure of tryptophan (Taniguchi, M, & Hino, T, *Tetrahedron* (1981) 37, 1487-1494; Bourne, G T, et al., *Perkin Trans. I* (1991) 1693-1699; Crich, D, & Banerjee, A, *Acc. Chem. Res.* (2007) 40, 151-161). These two isomers upon complexes with metal will result in rigid conformations: Bowl shaped conformation of Formula VIII or S shaped conformation of Formula IX (shown in FIG. 6).

In one general aspect the invention relates to a hexahydropyrrolo[2,3-b]indole compound of general Formula (XX):

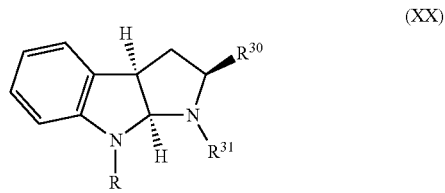

(XX)

In this general Formula (XX) R may be —COOR$^3$, —R$^4$COOR$^3$, —R$^4$COSR$^3$, R$^4$COSeR$^3$, —R$^4$CHO, —COR$^3$, —R$^4$COR$^3$, —R$^4$CONR$^3$R$^5$, —R$^4$COX, —R$^4$OP(=O)(OH)$_2$, —R$^4$P(=O)(OH)$_2$), —SO$_2$R$^3$, —R$^4$C(O)C(R$^3$)CR$^5$R$^6$, —R$^4$CO$_2$C(R$^3$)O, aryl or aryl-methylenyl. R$^{31}$ may be hydrogen, —COOR$^3$, —R$^4$COOR$^3$, —R$^4$COSR$^3$, R$^4$COSeR$^3$, —R$^4$CHO, —COR$^3$, —R$^4$COR$^3$, —R$^4$CONR$^3$R$^5$, —R$^4$COX, —R$^4$OP(=O)(OH)$_2$, —R$^4$P(=O)(OH)$_2$), —SO$_2$R$^3$, —R$^4$C(O)C(R$^3$)CR$^5$R$^6$ or —R$^4$CO$_2$C(R$^3$)O, i.e

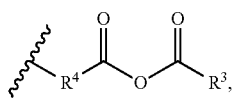

as well as aryl or aryl-methylenyl. $R^3$, $R^5$ and $R^6$ are independently from one another hydrogen, or an aliphatic, an alicyclic, an aromatic, an arylaliphatic, or an arylalicyclic group that includes 0 to about 3 heteroatoms independently selected from the group consisting of N, O, S, Se and Si. $R^4$ is one of an aliphatic bridge, an alicyclic bridge, an aromatic bridge, an arylaliphatic bridge and an arylalicyclic bridge, comprising 0 to about 3 heteroatoms. The heteroatoms may again be independently selected from N, O, S, Se and Si, Where $R^3$, $R^4$, $R^5$ and/or $R^6$ are an aliphatic moiety (including an aliphatic bridge), they typically have a main chain that has one to about 20 carbon atoms, including about 2 to about 20 carbon atoms, about 1 to about 15 carbon atoms, about 2 to about 15 carbon atoms, about 2 to about 10 carbon atoms or about 1 to about 10 carbon atoms. X is a halogen or a pseudohalogen.

In some embodiments R and/or $R^{31}$ is/are a nitrogen protecting group, of which numerous are known to those skilled in the art. In some embodiments R and $R^{31}$ are identical. In some embodiments R and $R^{31}$ are different from each other. In some embodiments $R^{31}$ is a nitrogen protecting group that is removable, i.e. cleavable from the nitrogen atom, in the presence of hydrogen ($H_2$). Examples of nitrogen protecting groups that are removed upon treatment with $H_2$ include, but are not limited to, formyl, benzyl, p-methylbenzyl, p-ethylbenzyl, p-trifluoromethylbenzyl, p-methylbenzyl, 4-methoxybenzyl, 9-phenylfluorenyl, diphenylmethyl, triphenylmethyl, phenylethoxycarbonyl, carbobenzyloxy (Cbz), p-dihydroxyboryl)benzyloxy carbonyl, benzisoxazolyl-methoxy carbonyl. In some embodiments R is a nitrogen protecting group that is stable in the presence of $H_2$. A large number of such nitrogen protecting groups are available. As a couple of illustrative examples may serve methyl, tert-butyl, allyl, prenyl, methoxymethyl, 2,4-dinitrophenyl, p-methoxyphenyl, o-methoxyphenyl, fluorenyl, benzenesulfenyl, benzoyl, 4-toluenesulfonyl (Tosyl, Ts), methoxycarbonyl, ethoxycarbonyl, 9-fluorenylmethyloxycarbonyl (FMOC), 2,6-di-t-butyl-9-fluorenylmethyloxycarbonyl, 2,7-bis(trimethylsilyl)fluorenylmethyloxycarbonyl, 2,2,2-trichloroethoxycarbonyl, trimethylsilylethoxycarbonyl, 1,1-dimethyl-2,2-dibromoethoxy-carbonyl, 2-(N,N-dicyclohexylcarboxamidoethoxycarbonyl, tert-butyloxycarbonyl (BOC), p-methoxybenzyl carbonyl (Moz or MeOZ), 1-(3,5-di-tert-butylphenyl)-1-methylethoxycarbonyl, triisopropylsiloxycarbonyl, vinyloxycarbonyl, prenyloxycarbonyl, p-methoxybenzyl-oxycarbonyl, methylsulfonylethylethoxy carbonyl, 2-(p-toluenesulfonyl)ethoxy carbonyl, m-nitrophenyloxy carbonyl, to name a few.

$R^{30}$ in general Formula (XX) may be $-C(OR^{11})R^{12}R^{13}$, $-C(SR^{11})R^{12}R^{13}$, $-C(SeR^{11})R^{12}R^{13}$, $-COOR^{14}$, $-COSR^{16}$, $-COSeR^{16}$, $-CON(R^{16})R^{17}$, $-CN$ or $-CHO$. $R^{11}$ may be hydrogen, $-OSO_2R^{15}$, $-Si-R^{16}R^{17}R^{18}$ or an aliphatic, an alicyclic, an aromatic, an arylaliphatic or an arylalicyclic group that includes 0 to about 3 heteroatoms independently selected from the group consisting of N, O, S, Se, and Si. $R^{12}$ and $R^{13}$ are independently from one another hydrogen, fluorine, $-Si-R^{16}R^{17}R^{18}$ or an aliphatic, an alicyclic, an aromatic, an arylaliphatic, or an arylalicyclic group that includes 0 to about 3 heteroatoms independently selected from the group consisting of N, O, S, Se and Si. $R^{14}$ may be hydrogen, halogen, $-Si-R^{16}R^{17}R^{18}$ or an aliphatic, an alicyclic, an aromatic, an arylaliphatic or an arylalicyclic group that includes 0 to about 3 heteroatoms independently selected from the group consisting of N, O, S, Se and Si. As a further illustration, in some embodiments where $R^{30}$ is $COOR^{14}$, $R^{14}$ may be alkyl or aryl-methylenyl. $R^{15}$ may be an aliphatic, an alicyclic, an aromatic, an arylaliphatic or an arylalicyclic group that includes 0 to about 3 heteroatoms independently selected from the group consisting of N, O, S, Se and Si. $R^{16}$, $R^{17}$ and $R^{18}$ are independently from one another hydrogen, or an aliphatic, an alicyclic, an aromatic, an arylaliphatic, or an arylalicyclic group that includes 0 to about 3 heteroatoms independently selected from the group consisting of N, O, S, Se and Si. In some embodiments one or more of $R^{11}$, $R^{12}$, $R^{13}$, $R^{14}$, $R^{16}$, $R^{17}$ and/or $R^{18}$ is/are, as applicable, identical to R. In some embodiments $R^{11}$, $R^{12}$, $R^{13}$, $R^{14}$, $R^{16}$, $R^{17}$ and/or $R^{18}$ is/are different from R.

In some embodiments where $R^{30}$ is $-COOR^{14}$, $-COSR^{16}$, $-COSeR^{16}$ or $-CON(R^{16})R^{17}$, $R^{14}$, $R^{16}$ and $R^{17}$ are independently hydrogen or a protecting group that can be removed in the presence of the moiety R. Hence in some embodiments the bond between R and the corresponding nitrogen of the hexahydropyrrolo[2,3-b]indole selection is at least essentially stable under conditions where $R^{14}$, $R^{16}$ and/or $R^{17}$, as may be applicable, are removable, including where these moieties are (/this moity is), removed. In some embodiments $R^{30}$ is identical to $R^{31}$. In some embodiments $R^{14}$, $R^{16}$, and $R^{17}$ are different from $R^{31}$. In some embodiments where $R^{30}$ is $-COOR^{14}$, $-COSR^{16}$, $-COSeR^{16}$ or $-CON(R^{16})R^{17}$, $R^{14}$, $R^{16}$ and $R^{17}$ are independently hydrogen or a protecting group that can be removed under conditions where $R^{31}$ can be removed. Accordingly in some and $R^{31}$ from a compound of general structure (XX) where R is a moiety that includes one or more of $R^{14}$, $R^{16}$ and $R^{17}$, as defined above.

In some embodiments $R^{31}$ is removable upon contact with $H_2$, i.e. by hydrogenolysis. $R^{31}$ may accordingly be a protecting group that is cleavable by means of exposure to $H_2$. Illustrative examples of respective moieties $R^{31}$ are benzyl carbamoyl, trifluoroacetyl, benzyl and triphenylmethyl (Trityl).

The term "aliphatic" means, unless otherwise stated, a straight or branched hydrocarbon chain, which may be saturated, i.e. alkyl or alkylene, or mono- or poly-unsaturated and include heteroatoms (see above). An unsaturated aliphatic group contains one or more double and/or triple bonds (alkenyl or alkynyl moieties). The branches of the hydrocarbon chain may include linear chains as well as non-aromatic cyclic elements. The (main) chain of an aliphatic moiety (including bridge), may, unless otherwise stated, be of any length, and contain any number of branches. Typically, the hydrocarbon (main) chain includes 1 to about 5, to about 10, to about 15, to about 20, to about 30 or to about 40 carbon atoms. Examples of alkenyl radicals are straight-chain or branched hydrocarbon radicals which contain one or more double bonds. Alkenyl radicals normally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, neopentyl, sec.-butyl, tert.-butyl, neopentyl and 3,3-dimethylbutyl. Both the main chain as well as the branches may furthermore contain heteroatoms as for instance N, O, S, Se or Si or carbon atoms may be replaced by these heteroatoms.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

The term "aromatic" means an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moietie may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-, (azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. In this regard, the term "aryl-methylenyl" includes the moieties —CH$_2$ar, —CHar$_2$ and -Car$_3$, with 'ar' representing an aromatic moiety. The two aromatic moieties in embodiment —CHar$_2$ and the three aromatic moieties in embodiment -Car$_3$ may be identical or different. The term "aryl-methylenyl" also includes the moiety —CH(alkyl)ar, with alkyl representing a cyclic or straight alkyl chain of 1 to about 10, 1 to about 8 or 1 to about 6 main chain atoms, including methyl, ethyl, propyl, isopryl, n-butyl or isobutyl. Typically, the hydrocarbon (main) chain of an arylaliphatic compound includes 5, 6, 7 or 8 main chain atoms in each ring of the aromatic moiety. Examples of arylaliphatic moieties include, but are not limited, to 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or 7,8-dibutyl-5,6-diethyl-isoquinoline.

As already indicated above, each of the terms "aliphatic", "alicyclic", "aromatic" and "arylaliphatic" as used herein is meant to include both substituted and unsubstituted forms of the respective moiety. Substituents may be any functional group such as —COOH (carboxy), —OH (hydroxy), —SH (thiol-), a dithiane-, —SeH (seleno-), —CHO (aldehyde), —CO— (carbonyl), —S(O$_2$)— (sulfonyl), sulfo-, sulfido-, —O— (oxo), sulfate (—OSO$_3$H), —NH$_2$ (amino), —NO (nitro), —NS, —NSe, a halogen such as —Br (bromo), —Cl (chloro) or —F (fluoro), an amino-, an imino-, an amido-, an imido-, an azido-, a diazo-, a cyano-, an isocyano-, a thiocyano-, a nitro-, a nitroso-, a sulfonyl- (e.g. a trifluoromethyl sulfonyl-, p-toluenesulfonyl-, bromobenzenesulfonyl-, nitrobenzenesulfonyl-, or a methane-sulfonyl), silyl-, silano- or a siloxy-group.

In some embodiments where $R^{30}$ is COOR$^{14}$, a compound of general Formula (XX) can be represented by Formula (XXI)

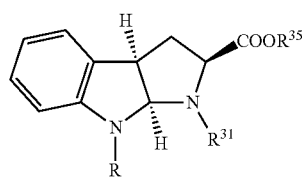

(XXI)

In Formula (XXI) R and $R^{31}$ are as defined above. $R^{35}$ is one of hydrogen, alkyl and a protecting group that is removable in the presence of the moiety R. An example of such a protecting group is arylmethylenyl. As already explained above, in some embodiments $R^{35}$ is identical to R, while in other embodiments $R^{35}$ is different from R. In some embodiments $R^{35}$ is a protecting group that can be removed in the presence of the moiety R. Thus in some embodiments the ester bond between $R^{35}$ and the carboxyl group can be cleaved under conditions where the bond between R and the nitrogen of the hexahydropyrrolo[2,3-b]indole selection is left at least essentially intact. In some embodiments $R^{35}$ is identical to $R^{31}$. In some embodiments $R^{35}$ is different from $R^{31}$. In some embodiments $R^{35}$ is a protecting group that can be removed under conditions where $R^{31}$ can be removed. Accordingly in some embodiments it is possible to simultaneously remove both $R^{35}$ and $R^{31}$ from a compound of general structure (XX).

In the Formulas depicting hexahydropyrrolo[2,3-b]indole compounds as used herein, the well established wedge representation is used to define the stereochemical configuration of the tricyclic moieties. The wedge representation defines one orientation of a substituent relative to another substituent and relative to a ring structure (see e.g. Pine, Hendrickson, Cram, Hammond: Organic Chemistry, McGraw-Hill, 4th edition, 1981, pages 97-99 & 115-119). By defining nonsuperimposable mirror images the absolute stereochemistry can accordingly be derived from the respective wedge representation.

The stereochemistry of the respective compound may be analysed according to any method known in the art, such as for instance 2D-NMR based on homo- or heteronuclear J-coupling values (Riccio, R., et al., *Pure Appl. Chem.* (2003) 75, 2-3, 295-308), electron ionisation mass spectrometry, polarimetry, circular dichroism spectroscopy (e.g. using the split Cotton-effect based on the Davydov splitting, see e.g. Allemark, S. G., *Nat. Prod. Rep.* (2000) 17, 145-155), enantioselective chromatography, derivatization in combination with standard analytical techniques such as NMR, including any suitable 2D-NMR technique, for example based on the nuclear Overhauser effect, as well as X-ray crystallography or solid state NMR (see e.g. Harper, J. K., et al., *J. Org. Chem.* (2003) 68, 4609-4614).

In embodiments where $R^{31}$ is hydrogen, a respective compound may also be represented by Formula (XXI A)

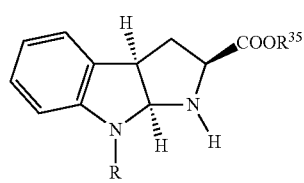

(XXIA)

In Formula (XXI A) R and $R^{35}$ are as defined above.

Accordingly, in other embodiments a compound of Formula (XXI) can be represented by Formula (XXIB)

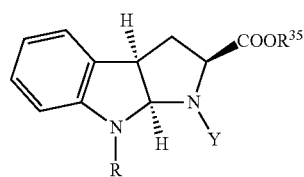

(XXIB)

In Formula (XXIB) R and $R^{35}$ are as defined above. Y is a nitrogen protecting group. In some embodiments Y is removable upon contact with $H_2$, i.e. by hydrogenolysis. Examples of a suitable nitrogen protecting group include, but are not limited to, a carbamate, methyl, t-butyl, N-allyl, benzyl, N-4-methoxybenzyl, N-2,4-dimethoxybenzyl, N-2-hydroxybenzyl, N-prenyl, N-cinnamyl, N-propargyl, methoxymethyl, N-([2-(Trimethylsilyl)ethoxy]methyl, N-3-Acetoxypropyl, N-cyanomethyl, an N-2-Azanor-borne, N-2,4-dinitrophenyl, N-p-methoxyphenyl, N-o-methoxyphenyl, N-Ifluorenyl, N-9-phenylfluorenyl, an amide or an aminocarbonyl group of a general underlying structure that corresponds to urea (cf. also above for further examples). Illustrative examples of carbamates are methyl-carbamate, ethylcarbamate, t-butyl carbamate, t-amyl carbamate, vinylcarbamate, allyl carbamate, triisopropylsiloxicarbamate, 4-nitrocinnamyl carbamate, 9-Fluorenylmethyl carbamate (Fmoc), 2,6-dibutyl-9-Fluorenylmethyl carbamate (Dtb-Fmoc), 2,7-bis(trimethylsilyl) fluorenylmethyl carbamate (Bts-Fmoc), 17-tetrabenzo[a,c,g,i]-fluorenylmethyl carbamate, 9-(2-sulfo)fluorenylmethyl carbamate, 2-chloro-3-indenyl-methyl carbamate (Climoc), benz[f]inden-3-ylmethyl carbamate (Bimoc), 9-(2,7-dibromo)-fluorenylmethyl carbamate, 1,1-dioxobenzyo[b] thiophene-2-ylmethyl carbamate (Bsmoc), 2-methylsulfonyl-3-phenyl-1-prop-2-enyloxy carbamate (Mspoc), 2,7-di-t-butyl[9-(10,10-di-oxo-10,10,10,10-tetrahydrothioxanthyl)]methyl carbamate (DBD-Tmoc), 2,2,2-trichloroethyl carbamate (Troc), 2-trimethylsilyl carbamate (Teoc), (2-phenyl-2-trimethylsilyl)ethyl carbamate (Psoc), 2-phenylethyl carbamate, 2-chloroethyl carbamate, 1,1-dimethyl-2,2-dibromoethyl carbamate, 1,1-dimethyl-2,2,2-trichloroethyl carbamate, 2-(2'-pyridyl)ethyl carbamate, 2-(4'-pyridyl)ethyl carbamate, 2,2-bis(4'-nitrophenyl)ethyl carbamate, 2-[(2-nitro-phenyl)dithio]-1-phenylethyl carbamate, 2-(N,N'-dicyclohexylcarboxamido)ethyl carbamate, 1-adamantyl carbamate, 1-(1-adamantyl)-1-methyl carbamate, 1-methyl-1-(4-biphenyl-yl)ethyl carbamate, 1-(3,5-di-t-butylphenyl)-1-methylethyl carbamate, 8-quiolyl carbamate, N-hydroxypiperidinyl carbamate, an alkyldithio carbamate (in particular with alkyl being methyl, ethyl, isopropyl, n-propyl or t-butyl), phenyldithio carbamate, 3,5-di-t-butylbenzyl carbamate, p-methoxybenzyl carbamate, p-nitrobenzyl carbamate, a halobenzyl carbamate, 2-naphtylmethyl carbamate, diphenylmethyl carbamate, 9-anthrylmethyl carbamate, 4-phenylacetoxy carbamate, 4-azidobenzyl carbamate, 2-methylthioethyl carbamate, 2-methylsulfonylethyl carbamate, 2-(p-toluenesulfonyl) ethyl carbamate, [2-(1,3-dithiany)-methyl carbamate, 1,1-dimethyl-2-cyanoethyl carbamate, 2-(4-nitrophenyl)ethyl carbamate, m-nitrophenyl carbamate, 3,5-dimethoxybenzyl carbamate, phenyl(o-nitrophenyl)methyl carbamate and 4-methoxyphenacyl carbamate. Illustrative examples of suitable amides are formamide, acetamide, chloroacetamide, trifluoroacetamide, phenylacetamide, 3-phe-nylpropanamide, pent-4-enamide, picolinamide, 3-pyridylcarboxacetamide, benzamide, p-phenylbenzamide, o-(benzyloxymethyl)benzamide, o-hydroxy-trans-cinnamide, 2-([t-butyl-diphenylsiloxy]methyl]benzoyl, o-hydroxy-trans-cinnamide, 4-chlorobutanamide, aceto-acetamide and 2-methyl-2-(o-phenylazophenoxy)propanamide. Illustrative examples of suitable aminocarbonyl groups of a general underlying structure that corresponds to urea are the phenothiazinyl-(10)-carbonyl group, the N-p-tuloenesulfonylaminocarbonyl group, the N'-phenylaminothiocarbonyl group, the 4-hydroxyphenylaminocarbonyl group and the 3-hydroxytryptaminocarbonyl group. Further suitable examples of a nitrogen protecting group include, but are not limited to, sulfonyl groups such as methanesulfonyl, trifluoromethanesulfonyl, t-butylmethanesulfonyl, benzylsulfonyl, 2-(trimthylsilyl) ethanesulfonyl, p-toluenesulfonyl, o-anisylsulfonyl, dinitrobenzenesulfonyl or naphtalenesulphonyl. Yet further suitable examples of a nitrogen protecting group include, but are not limited to, silyl groups such as t-butyldiphenylsilyl, sulfenyl groups such as benzenesulfenyl, 2,4-dinitro-benzenesulfenyl, pentachlorobenzenesulfenyl, triphenylmethylsulfenyl or 3-nitro-2-pyridinesulfenyl.

In some embodiments $R^{30}$ in general Formula (XX) is —C($R^1$)($R^2$)OH. Typically, in such embodiments Y in general Formula (XX) is hydrogen. In some embodiments a respective hexahydropyrrolo[2,3-b]indole compound can be represented by Formula (VII):

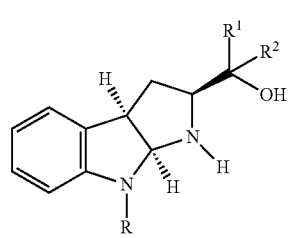

(VII)

In Formula (VII) R is one of —COOR³, —R⁴COOR³, —R⁴CHO, —R⁴COR³, —R⁴CONR⁵R⁶, —R⁴COX, —R⁴OP(=O)(OH)₂, —R⁴P(=O)(OH)₂, —R⁴C(O)C(R³)

CR$^5$R$^6$ and —R$^4$CO$_2$C(R$^3$)O. R$^3$, R$^5$ and R$^6$ are independent from one another one of hydrogen, an aliphatic group, an alicyclic group, an aromatic group, an arylaliphatic group and an arylalicyclic group, that includes 0 to about 3 heteroatoms, such as one, two or three heteroatoms. Examples of suitable heteroatoms, i.e. atoms different from carbon, include, but are not limited to, N, O, S, Se and Si. R$^4$ is one of an aliphatic bridge, an alicyclic bridge, an aromatic bridge, an arylaliphatic bridge and an arylalicyclic bridge, that includes 0 to about 3 heteroatoms, such as N, O, S, Se and Si. In a compound of Formula (VII) an aliphatic group (including an aliphatic bridge) typically has a main chain that has 1 to about 20 carbon atoms, such as 1 to about 15, 1 to about 12, or 1 to about 10 carbon atoms, including about 2 to about 20 carbon atoms, about 2 to about 15 carbon atoms, 1 about 2 to about 12 or about 2 to about 10 carbon atoms. Accordingly, in some embodiments a corresponding aliphatic group is (C$_1$-C$_{10}$) alkyl. As indicated above, the aliphatic group may in addition have up to three heteroatoms. As explained above, aliphatic groups may be alkyl radicals, which may be substituted by one or more substituents, such as by —OH, —O—(C$_1$-C$_{10}$)-alkyl, —O-phenyl, —O—CO—(C$_1$-C$_{10}$)-alkyl, —O—CO-aryl, —CO—(C$_1$-C$_5$)-alkyl, —CO—O—(C$_1$-C$_5$)-alkyl, —CO—O-aryl, or aryl. Likewise, an alicyclic group, an aromatic group, an arylaliphatic group and an arylalicyclic group may be substituted by one or more identical or different substituents. These may for instance be selected from the group of halogen, (C$_1$-C$_5$)-alkyl or phenyl, —OH, —O—(C$_1$-C$_5$)-alkyl, (C$_1$-C$_2$)-alkylenedioxy, —NO$_2$, —CO—(C$_1$-C$_5$)-alkyl, —CF$_3$, —CN, —CONR$^7$R$^8$, —COOH, —CO—O—(C$_1$-C$_5$)-alkyl, —(C$_1$-C$_5$)-alkyl, where R$^7$ and R$^8$ are independent from one another one of hydrogen, an aliphatic group, an alicyclic group, an aromatic group, an arylaliphatic group and an arylalicyclic group, that includes 0 to about 3 heteroatoms, such as one, two or three heteroatoms. In some embodiments an alicyclic, an aromatic, an arylaliphatic or an arylalicyclic group (including a respective bridge) representing one of R$^3$, R$^4$, R$^5$ and R$^6$ may likewise have a main chain that has 1 to about 20, such as 1 to about 15, 1 to about 12, or 1 to about 10 carbon atoms, including about 2 to about 20 carbon atoms, about 2 to about 15 carbon atoms, 1 about 2 to about 12 or about 2 to about 10 carbon atoms. In some embodiments a corresponding alicyclic group is (C$_3$-C$_8$) cycloalkyl, such as a four-membered, a five-membered, a six-membered a seven-membered or an eighth-membered alicyclic ring. In some embodiments some or all of R$^3$, R$^4$, R$^5$ and R$^6$, as present in a corresponding compound, are identical. X is a halogen atom, such as F, Cl, Br, or I.

R$^1$ and R$^2$ are independent from each another selected from hydrogen, an aliphatic group, an alicyclic group, an aromatic group, an arylaliphatic group and an arylalicyclic group. The above said for an aliphatic group and embodiments of an alicyclic, an aromatic, an arylaliphatic or an arylalicyclic group, also applies to R$^1$ and R$^2$. In some embodiments R$^1$ and R$^2$ are identical, whereas in other embodiments they are different. In one such embodiment R$^1$ and R$^2$ are both aryl. As noted above, aryl may be phenyl, naphthyl, or alkylaryl, for example, tolyl, xylyl, or heteroaryl, all of which may be substituted by one or more identical or different substituents selected from the group halogen, (C$_1$-C$_5$)-alkyl or phenyl, —OH, —O—(C$_1$-C$_5$)-alkyl, (C$_1$-C$_2$)-alkylenedioxy, —NO$_2$, —CO—(C$_1$-C$_5$)-alkyl, —CF$_3$, —CN, —CONR$^7$R$^8$, —COOH, —CO—O—(C$_1$-C$_5$)-alkyl, —(C$_1$-C$_5$)-alkyl. R$^7$ and R$^8$ are independent from one another one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si. As also explained above, aliphatic groups may be alkyl radicals, which may be substituted by one or more substituents, such as by —OH, —O—(C$_1$-C$_{10}$)-alkyl, —O-phenyl, —O—CO—(C$_1$-C$_{10}$)-alkyl, —O—CO-aryl, —CO—(C$_1$-C$_5$)-alkyl, —CO—O—(C$_1$-C$_5$)-alkyl, —CO—O-aryl, or aryl.

In some embodiments a respective a hexahydropyrrolo[2,3-b]indole compound is provided in form of a compound of Formula (VIII)

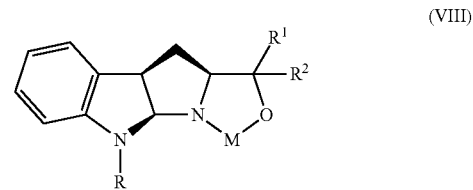

(VIII)

As can be taken from Formula (VIII), the compound has a bowl-shaped conformation. In Formula (VIII) M is a metal compound selected from the group consisting of Group 1 to Group 14 metals of the periodic table of the chemical elements (according to the new IUPAC system), lanthanides and actinides. In some embodiments M may for instance be a compound of a metal of Group 13, such as a boron compound, including an organo borane compound, an aluminium compound, including an aluminium organic compound, an indium compound, including an indium organic compound, or a gallium compound, including a gallium organic compound. In some embodiments M may for instance be a compound of a metal of Group 13, such as Zinc compound. In some embodiments M may be a compound of a metal of Group 14, such as tin compound. In some embodiments M may be a compound of a metal of Group 12, such as a zinc compound or a cadmium compound. In some embodiments M may be a compound of a metal of Group 11, such as a copper or a silver compound. In some embodiments M may be a compound of a metal of Group 9, such as an iridium compound or a rhodium compound. In some embodiments M may be a compound of a metal of Group 4, such as a titanium compound or a zirconium compound. In some embodiments M may be a compound of a lanthanide such as lanthanum or cerium. As a few illustrative examples, M may in some embodiments be one of BH$_3$, B$_2$H$_6$, B$_5$H$_9$, B$_{10}$H$_{14}$, AlCl$_3$, ZnCl$_2$, Zn(OTf)$_2$, ZnEt$_2$, SnCl$_2$, TiCl$_4$, Ti(Oi-Pr)$_4$, Cp$_2$TiCl$_2$, ZrCl$_4$, Cp$_2$ZrCl$_2$, InCl$_3$, In(OTf)$_3$, Cu(OAc)$_2$, (IrCp*Cl$_2$)$_2$, (Ir(COD)Cl)$_2$, LnCl$_3$, and LnCp$_2$Cl$_2$. R, R$^1$ and R$^2$ are as defined above.

In some embodiments a respective hexahydropyrrolo[2,3-b]indole compound has an S-shaped conformation and can be represented by Formula (IX)

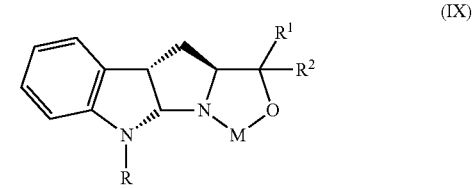

(IX)

In Formula (IX) moieties M, R, R$^1$ and R$^2$ are as defined above.

In some embodiments $R^{30}$ in general Formula (XX) is —COOR$^9$ or —COOR$^{10}$. In some of these embodiments a respective hexahydropyrrolo[2,3-b]indole compound can be represented by Formula (VI)

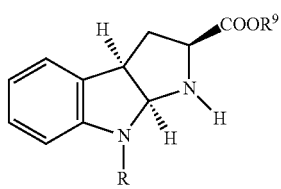

(VI)

In Formula (VI) $R^9$ is an aliphatic moiety, which may in some embodiments have a main chain that includes 1 to about 20 carbon atoms, such as such as 1 to about 15, 1 to about 12, or 1 to about 10 carbon atoms. Accordingly, in some embodiments a corresponding aliphatic group is $(C_1-C_{10})$ alkyl. As indicated above, the aliphatic group may in addition have up to three heteroatoms. In some embodiments, $R^9$ is one of methyl, ethyl, n-propyl, iso-propyl, n-butyl, iso-butyl, tert-butyl or trifluoromethyl. In some embodiments R and $R^9$ are identical.

In some of these embodiments a respective hexahydropyrrolo[2,3-b]indole compound can be represented by Formula (IV)

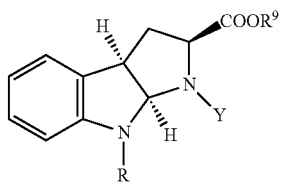

(IV)

In Formula (IV) Y is a nitrogen protecting group (cf. above). Y may in some embodiments be sensitive to $H_2$, i.e. removable by hydrogenolysis. In one embodiment, the nitrogen protecting group is selected from the group consisting of alkoxycarbonyl, benzyhdryl, trifluoroacetyl group, t-butoxycarbonyl group, carbamates including methyl, ethyl and substituted ethyl carbamates, amides, cyclic imide derivatives, N-Alkyl and N-Aryl amines, imine derivatives, and enamine derivatives. R and $R^9$ are as defined above.

In further embodiments a respective hexahydropyrrolo[2,3-b]indole compound can be represented by Formula (IVA)

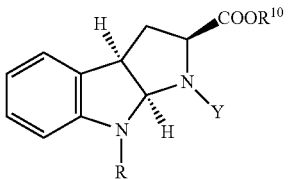

(IVA)

In Formula (IV A) $R^{10}$ is a protecting group that is removable in the presence of the moiety R. An example of such a protecting group is arylmethylenyl. Examples of suitable aryl-methylenyl groups include, but are not limited to, benzyl, diphenylmethyl, dibenzysuberyl, 2,4,6-trimethylbenzyl, p-bronobenzyl, o-nitrobenzyl, p-nitrobenzyl, 4-sulfobenzyl, 4-picolyl, 2-naphthylmethyl and 1,2,3,4-tetrahydro-1-naphthyl. As already explained above, in some embodiments $R^{10}$ is a protecting group that can be removed in the presence of the moiety R. Thus in some embodiments the ester bond between $R^{10}$ and the carboxyl group can be cleaved under conditions where the bond between R and the nitrogen of the hexahydropyrrolo[2,3-b]indole selection is left at least essentially or entirely intact. In some embodiments $R^{10}$ is a protecting group that can be removed under conditions where Y can be removed. Accordingly in some embodiments it is possible to simultaneously remove both Y and $R^{10}$ from a compound of general structure (IV A). An example of conditions where this is achievable is an embodiment where $R^{10}$ is arylmethylenyl and its removal is carried out via hydrogenolysis. R and Y are as defined above. In some embodiments Y may be removable by hydrogenolysis.

In further embodiments a respective hexahydropyrrolo[2,3-b]indole compound can be represented by Formula (VIA)

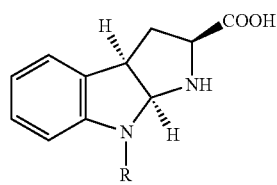

(VIA)

In Formula (VIA) R is as defined above.

Compounds according to the invention of the Formula (VII) can be obtained as shown in FIG. 15. Starting from the commercially available Nα-protected L-tryptophan 1, for example Nα-carbobenzyloxy-L-tryptophan, initial DCC coupling with methanol followed by acid catalyzed ring closure provided the hexahydro[2,3-b]pyrrolo indole 3 as diastereoisomeric cyclic tautomers. In agreement with literature precedent (Taniguchi, M, & Hino, T, *Tetrahedron* (1981) 37, 1487-1494; Bourne, G T., et al., *J. Chem. Soc., Perkin Trans. I* (1991) 1693-1699; Crich, D, & Banerjee, A, *Acc. Chem. Res.* (2007) 40, 151-161), after sodium carbonate-mediated protection, the thermodynamically stable trans isomer of compound (IV) was obtained and the less stable diastereoisomer reverted back to starting material 1. Initial attempts to direct Grignard addition to compound (IV) (cf. FIG. 2) were, surprisingly, unsuccessful. No reaction was observed. It was speculated that this effect might be caused by the highly crowded nature of the structure. To remove the steric effect, an alternative approach was followed by removing the protecting group first, followed by subsequent Grignard addition. This strategy proved successful and a series of chiral ligands 7a-h were obtained in good yields (FIG. 15).

Thus the present invention provides a method of preparing a compound of Formula (VII)

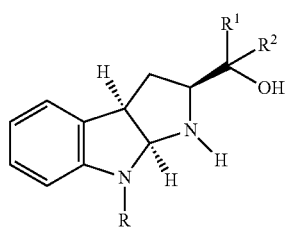

(VII)

by reacting a compound of Formula (VI)

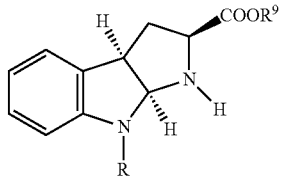

with a Grignard reagent $R^1MgX$, $R^2MgX$ or a mixture of $R^1MgX$ and $R^2MgX$. $R^1$ and $R^2$ in the Grignard reagent and in Formula (VI) are as defined above. R in Formulas (VII) and (VI) and Y in Formula (VI) are also as defined above. Generally, Y is removable upon contact with $H_2$, i.e. by hydrogenolysis.

The present invention further provides a method of forming a compound of Formula (XXI A)

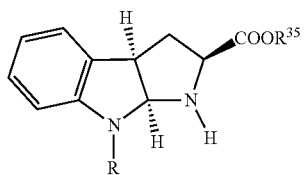

in which R and $R^{35}$ are as defined above. $R^{31}$ of Formula (XXI) is hydrogen. The method includes providing a compound of Formula (XXIB)

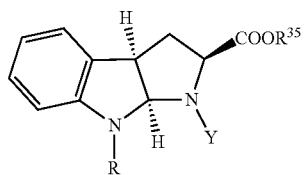

In Formula (XXIB) R and $R^{35}$ are as defined above. Y is a nitrogen protecting group (supra), which is generally removable upon contact with $H_2$, i.e. by hydrogenolysis. The method further includes contacting the compound of Formula (XXIB) with $H_2$ in the presence of a suitable catalyst such as a heterogeneous catalyst. Typical examples of a heterogeneous catalyst are a Raney catalyst (e.g. Raney nickel), Adam's catalyst, Palladium black or a carrier based catalst such as a Pd/C, Ni/C, Rh/C or a Lindlar catalyst, Palladium Black, or Raney nickel. Thereby cleavage of the bond between moiety Y and the corresponding nitrogen atom of the tricyclic compound of Formula (XXIB) is allowed to occur. Accordingly, deprotection of the Nα group of the compound of Formula (XXIB) is allowed. Where $R^{35}$ is arylmethylenyl such as benzyl a cleavage of the ester bond to moiety $R^{35}$ is in the same process effected. Thus deprotection of the carboxyl group of the tricyclic compound of Formula (XXIB) is allowed to occur in such embodiments.

Deprotection of the Nα group of the compound of Formula (XXIB) may be allowed to occur in any desired solvent, whether nonpolar (aprotic), dipolar protic or dipolar aprotic. Typically an organic solvent is used. Examples of non-polar solvents include, but are not limited to, hexane, heptane, cyclohexane, benzene, toluene, pyridine, dichloromethane, 1,2-dichloroethane, chloroform, carbon tetrachloride, carbon disulfide, tetrahydrofuran, dioxane, diethyl ether or diisopropylether. Examples of dipolar aprotic liquids are methyl ethyl ketone, chloroform, tetrahydrofuran, dioxane, ethylene glycol monobutyl ether, pyridine, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, methanol, ethanol, propanol, isopropanol, butanol, N,N-diisopropylethylamine, and dimethylsulfoxide. In some embodiments allowing deprotection of the Nα group of the compound of Formula (XXIB) and thus of the formation of a compound of Formula (XXI A) is carried out in a polar protic solvent. Examples of polar protic solvents include, but are not limited to methanol, ethanol, butyl alcohol, formic acid, dimethylarsinic acid $[(CH_3)_2AsO(OH)]$, N,N-dimethyl-formamide, N,N-diisopropylethylamine, or chlorophenol.

In some embodiments the method of forming a compound of Formula (XXI A) is a method of forming a compound of Formula (VI) according to the present invention (see above)

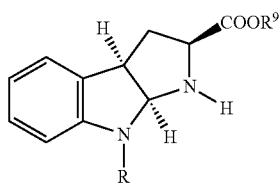

The method includes providing a compound of Formula (IV) as defined above

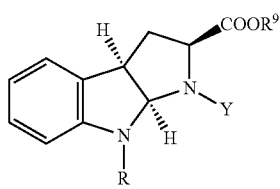

The method further includes contacting the compound of Formula (IV) with $H_2$ in the presence of a Pd/C catalyst, a Ni/C catalyst, a Rh/C catalyst or another suitable catalyst as illustrated above. Thereby cleavage of the bond between moiety Y and the corresponding nitrogen atom of the tricyclic compound of Formula (IV) is allowed to occur. Hence, the method includes allowing the Nα group of the compound of Formula (IV) to be deprotected in the presence of Pd/C catalyst.

In some embodiments providing the compound of Formula (IV) includes providing a compound of Formula (III)

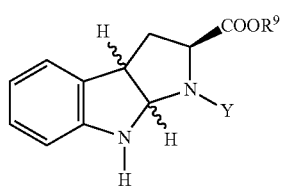

In Formula (III) $R^9$ is alkyl as defined above. In some embodiments, $R^9$ is $(C_1-C_{10})$ alkyl, such as methyl, ethyl, propyl, or butyl. Y is a nitrogen protecting group as explained above. In one embodiment, the nitrogen protecting group is selected from alkoxycarbonyl, benzhydryl, the trifluoroacetyl group, the t-butoxycarbonyl group, a carbamate including methyl-, ethyl- and substituted ethyl carbamates, an amide, a cyclic imide derivative, an N-Alkyl amine, an N-Aryl amine, an imine derivative, and an enamine derivative. The compound of Formula (III) is contacted with an acyl halide RCOX in the presence of an inorganic base such as an alkali base. The inorganic base typically has an alkali metal, alkali earth metal, or other metallic cation, and an anion such as hydroxide, carbonate or bicarbonate. Examples of a suitable inorganic base include, but are not limited to, sodium carbonate, sodium hydrogen carbonate, potassium carbonate, potassium hydrogen carbonate sodium hydroxide, potassium hydroxide and calcium carbonate. In Formula RCOX moiety X is halogen such as F, Cl, Br or I. R is as defined above.

Contacting the compound of Formula (III) with an acyl halide RCOX may be carried out in any desired solvent in which the acyl halide is stable to n extent that the desired reaction can proceed. Accordingly, typically an organic solvent is used. In some embodiments contacting the compound of Formula (III) with an acyl halide RCOX is carried out in a dipolar protic solvent. Examples of dipolar aprotic solvents include, but are not limited to, methyl ethyl ketone, chloroform, tetrahydrofuran, dioxane, ethylene glycol monobutyl ether, pyridine, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, methanol, ethanol, propanol, isopropanol, butanol, N,N-diisopropylethylamine, and dimethylsulfoxide.

In related embodiments of forming a compound of Formula (XXI A) (supra) according to the invention a compound of Formula (VIA), as defined above, is synthesized.

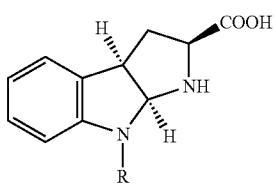

(VIA)

In Formula (VIA) R is as defined above.

The respective method (or embodiment with regard to forming a compound of Formula (XXIA)) includes providing a compound of Formula (IV A) as defined above

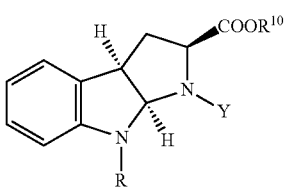

(IVA)

The method further includes contacting the compound of Formula (IV A) with $H_2$ in the presence of a Pd/C catalyst. Thereby cleavage of the bond between moiety Y and the corresponding nitrogen atom of the tricyclic compound of Formula (IV) is allowed to occur. Hence, the method includes allowing the Nα group of the compound of Formula (IV) to be deprotected in the presence of Pd/C catalyst. Further the cleavage of the ester bond between moiety $R^{10}$ and the corresponding carbonyl group is allowed to occur.

In some embodiments providing the compound of Formula (IV) includes providing a compound of Formula (III A) as defined above

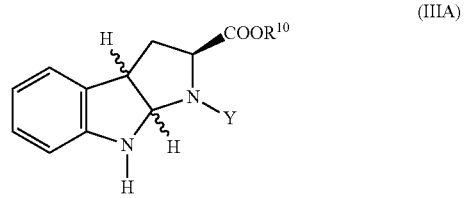

(IIIA)

The compound of Formula (III A) is contacted with an acyl halide RCOX in the presence of an inorganic base such as an alkali base. Examples of a suitable inorganic base include, but are not limited to, sodium carbonate, potassium carbonate, sodium hydroxide, potassium hydroxide and calcium carbonate. In Formula RCOX moiety X is halogen such as F, Cl, Br or I, and R is as defined above. In some embodiments contacting the compound of Formula (III A) with an acyl halide RCOX is carried out in a dipolar protic solvent (supra).

A compound of Formula (VI) as defined above is used in a further method according to the invention. The respective method is a method of forming a compound of Formula (VII) as defined above

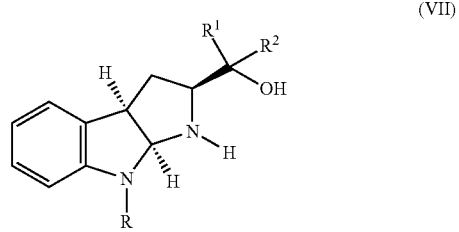

(VII)

The method includes providing a compound of Formula (VI), for instance by forming the same as defined above, or by obtaining the same in another way. The compound of Formula (VI)

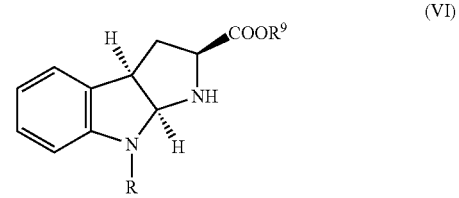

(VI)

is contacted with a compound $R^1MgX$, $R^2MgX$ or a mixture of $R^1MgX$ and $R^2MgX$. $R^1$ and $R^2$ are as defined above and X is halogen (supra). As noted above, in some embodiments $R^1$ and $R^2$ are identical, in which case only one compound $R^1MgX$ or $R^2MgX$ needs to be contacted with the compound of Formula (VI). In some embodiments contacting the compound of Formula (VI) with a compound $R^1MgX$, $R^2MgX$ or a mixture thereof is carried out in a dipolar protic solvent (supra).

Further, a method of forming a compound of Formula (IV) as defined above is provided

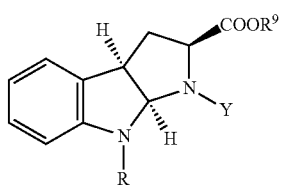

(IV)

The method includes providing a compound of Formula (III) as defined above

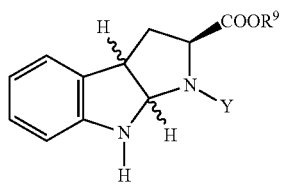

(III)

The compound of Formula (III) is contacted with an acyl halide RCOX (supra) in the presence of an inorganic base as defined above. In some embodiments contacting the compound of Formula (III) with an acyl halide RCOX is carried out in a dipolar protic solvent (supra).

In a related method the invention provides a method of forming a compound of Formula (IVA) as defined above

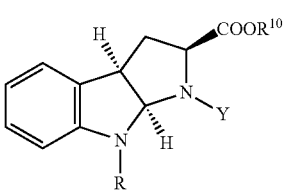

(IVA)

The method includes providing a compound of Formula (IIIA) as defined above

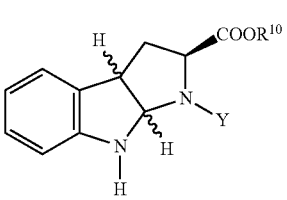

(IIIA)

The compound of Formula (III A) is contacted with an acyl halide RCOX (supra) in the presence of an inorganic base as defined above. In some embodiments contacting the compound of Formula (III A) with an acyl halide RCOX is carried out in a dipolar protic solvent (supra).

The present invention also provides a method of forming a compound of Formula (VIII) as defined above

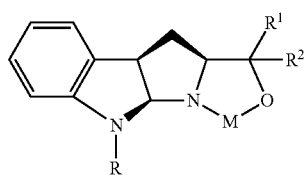

(VIII)

The method includes providing a compound of Formula (VII) as defined above, for instance by forming the same as defined above, or by obtaining the same in another way. The compound of Formula (VII)

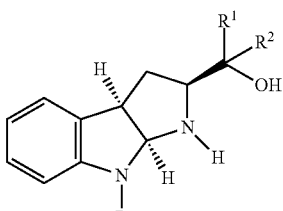

(VII)

is contacted with a metal compound selected from the group consisting of Group 1 to Group 14 metals, lanthanides and actinides. In one embodiment of the invention, the metal compound M is selected from the group consisting of $BH_3$, $B_2H_6$, $B_5H_9$, $B_{10}H_{14}$, $AlCl_3$, $ZnCl_2$, $Zn(OTf)_2$, $ZnEt_2$, $SnCl_2$, $TiCl_4$, $Ti(Oi\text{-}Pr)_4$, $Cp_2TiCl_2$, $ZrCl_4$, $Cp_2ZrCl_2$, $InCl_3$, $In(OTf)_3$, $Cu(OAc)_2$, $(IrCp^*Cl_2)_2$, $(Ir(COD)Cl)_2$, $LnCl_3$, $LnCp_2Cl_2$.

The present invention also provides a method of preparing a compound of Formula (IX) as defined above

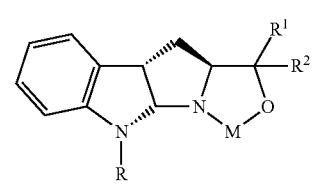

(IX)

The method includes providing a compound of Formula (VII) as defined above, for instance by forming the same as defined above, or by obtaining the same in another way. The compound of Formula (VII)

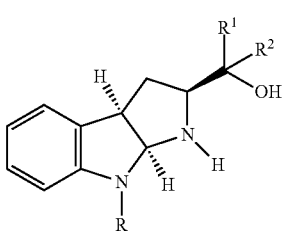

(VII)

is contacted with a metal compound selected from the group consisting of Group 1 to Group 14 metals, lanthanides and actinides, (see above).

As explained above, in one embodiment, the metal compound M can be selected from the group consisting of $BH_3$, $B_2H_6$, $B_5H_9$, $B_{10}H_{14}$, $AlCl_3$, $ZnCl_2$, $Zn(OTf)_2$, $ZnEt_2$, $SnCl_2$, $TiCl_4$, $Ti(Oi\text{-}Pr)_4$, $Cp_2TiCl_2$, $ZrCl_4$, $Cp_2ZrCl_2$, $InCl_3$, $In(OTf)_3$, $Cu(OAc)_2$, $(IrCp^*Cl_2)_2$, $(Ir(COD)Cl)_2$, $LnCl_3$, and $LnCp_2Cl_2$. It is noted that a compound of Formula (IX) is often not stable under acidic conditions. However, using a radical reagent such as N-phenylselenophtalimide in an aprotic nonpolar solvent in the presence of pyridinium p-toluenesulfonate such difficulties may be avoided (cf. e.g Depew, K M, et al., *J. Am. Chem. Soc.* (1999) 1221, 11953-11963).

The present invention also relates to the use of the compounds of Formula VII as chiral ligand for asymmetric catalysis, particularly to the asymmetric reduction of ketones. In these uses the respective compound serves as a so called "active catalyst" in that it converts an achiral reactant to a chiral product. Such a chiral product has asymmetry, in that it is non-superposable on its mirror image. Without the intent of being bound by theory it is believed that the tricyclic rigid ring system of the hexahydropyrrolo-[2,3-b]indole skeleton provides a chiral pocket that directs the stereochemistry of reactions catalysed by a respective compound. Hence, the chiral moiety has a mirror image, which would provide the chiral chromatography stationary phase with identical physical properties in non-chiral environments. As illustrated in e.g. FIG. 5 or FIG. 8 the invention thereby provides a variety of methods of stereoselective synthesis.

The use of these chiral ligands for asymmetric catalysis is for example illustrated in the asymmetric reduction of ketones as shown in the examples below (see also FIGS. 11 and 12). Such a use includes the formation of enantiomerically enriched, including at least essentially enantiomerically pure, secondary alcohols. The term "at least essentially enantiomerically pure" refers to an enantiomeric excess (e.e.) of at least 95%, such as an excess (e.e.) of at least 96%, at least 97%, at least 98% or at least 99%, including an e.e. of more than 99.5%. As an illustrative example, a sample with 98.5% of R isomer and 1.5% of S isomer has an enantiomeric excess of 97%. Accordingly, such a mixture can also be taken as a mixture of 97% pure R isomer with 3% of a racemic mixture. In the exemplary scheme on top of FIG. 11, $R^{23}$ and $R^{33}$ are independently from one another an aliphatic, an alicyclic, an aromatic, an arylaliphatic, or an arylalicyclic group that includes 0 to about 3 heteroatoms independently selected from the group consisting of N, O, S, Se and Si. Any reducing agent such as a borane, a silane, or a hydride such as tetrahydridoborate or tetrahydridoaluminate may be used, with which a compound of Formula (VII) may be employed as a ligand.

Figure 13D:
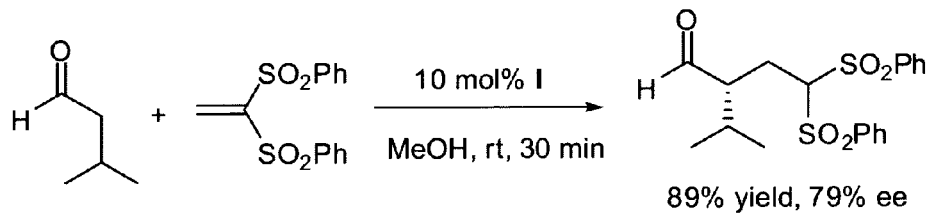
FIG. 13D depicts a further asymmetric Michael reaction, the (10) catalysed addition of isovaleraldehyde to vinyl sulphone.
Figure 14:
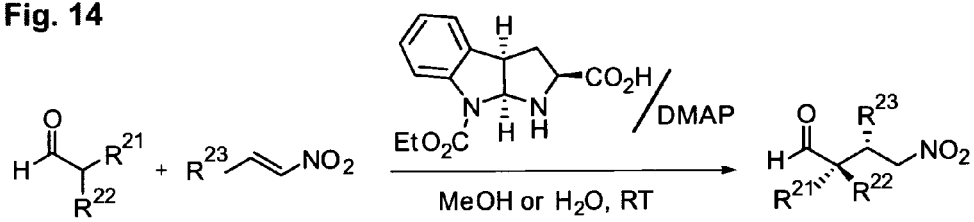
FIG. 14 is a table depicting exemplary data on the catalytic asymmetric Michael addition of unmodified aldehydes to Nitroalkenes. Reactions were conducted with 2 equiv of aldehyde, 1 equiv of nitrostyene at room temperature or 4 equiv of aldehyde at 60° C. (for bulky aldehydes in entries 12-14), in the presence of catalyst with 1:1 catalyst/DMAP. Generally 0.2 mmol nitroalkene, 0.4 mmol aldehyde were used at room temperature and 0.2 mmol nitroalkene, 0.8 mmol aldehyde at 60° C. $^a$ Isolated yield. $^b$ Dr was determined by chiral HPLC analysis after purification $^c$ Reported values refer to the syn isomer and were determined by chiral HPLC on a chiral stationary phase. Cy in entry 6 means cyclohexyl.
Figure 14:
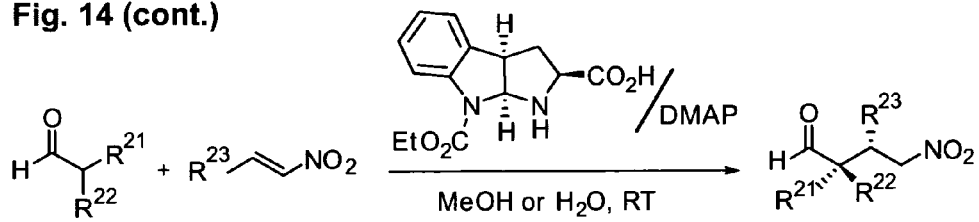

The asymmetric Michael reaction is recognized as a highly important enantioselective carbon-carbon bond-forming reaction. Accordingly, the suitability of the compounds of Formula (VI A) of the invention has been examined. The data summarized in FIG. 13 and FIG. 14 illustrate the suitability of the catalysts to be used in a variety of solvents. In some embodiments a basic cocatalyst is used together with the compound of Formula. In some embodiments the basic cocatalyst is an organic compound such as an amine, for example an amine such as ethylamine, triethylamine, n-butylamine, di-n-butylamine, piperidine, isopropylamine, dimethylamine, cyclohexylamine, dicyclohexyl-amine pyridine, methylpyridine, dimethylpyridine or 4-(N,N-dimethylamino)pyridine.

The Michael reaction can in typical embodiments be represented by the following two equations:

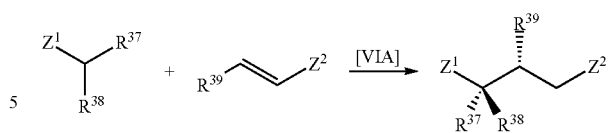

In the compounds depicted in these equations moieties both $Z^2$, $Z^3$ and $Z^3$ (in the second equation) are an electron withdrawing group such as one of $NO_2$, CN, $C(R^{40})O$, $COOR^{40}$, $CONR^{40}R^{41}$ and $SO_2R^{40}$ wherein $R^{40}$ and $R^{41}$ are independent from one another one of hydrogen, an aliphatic group, an alicyclic group, an aromatic group, an arylaliphatic group and an arylalicyclic group, comprising 0 to about 3 heteroatoms independently selected from the group consisting of N, O, S, Se and Si. $R^{38}$ and $R^{39}$ are independently from one another hydrogen, fluorine or one of an aliphatic, an alicyclic, an aromatic, an arylaliphatic, or an arylalicyclic group that includes 0 to about 3 heteroatoms independently selected from the group consisting of N, O, S, Se and Si. $R^{37}$ is a further electron withdrawing group as exemplified above or it is hydrogen or flourine or one of an aliphatic group, an alicyclic group, an aromatic group, an arylaliphatic group and an arylalicyclic group, comprising 0 to about 3 heteroatoms independently selected from the group consisting of N, O, S, Se and Si. Accordingly, the Michael donor in the Michael addition is for instance in some embodiments a carbonyl group such as an aldehyde, a ketone or carboxyl group. The Michael acceptor in the Michael addition is in some embodiments a nitro group, a carbonyl group, a carboxyl group or a sulphonyl group. An example of vinyl sulphones as the Michael acceptor is depicted in FIG. 13D. In the conjugate addition of isovaleraldehyde to 1,1-bis(phenylsulfonyl)ethylene, the desired product could be obtained in 89% yield and 79% ee without optimization (FIG. 13D). In contrast thereto, proline gave low yield and low ee for this reaction.

It is noted that where both $Z^2$ and $Z^3$ are the cyano group poor yields with products in undeterminable amounts have been found. The respective reaction conditions may need to be further analysed. It may nevertheless be advisable to carry out the Michael reaction depicted in the second equation with the proviso that not both $Z^2$ and $Z^3$ are CN.

Without the intend of being bound by theory it is speculated that upon addition of a base such as 4-(N,N-dimethylamino)pyridine (DMAP), an acid-base interaction between the carboxylic acid and the amino groups should lead to the formation of an ammonium salt, which renders the base as the stereo controlling module.

The Michael reaction may for example be carried out in a protic dipolar solvent, for instance an alcoholic solvent such as ethanol, propanol, isopropanol, butanol, methanol, tert-butanol, isobutanol, tert-amyl alcohol, cyclohexanol or phenol. In particular where a basic cocatalyst is used, the reaction may also be carried out in an aqueous solvent. The Michael reaction may also be carried out in an aprotic dipolar solvent such as tetrahydrofuran, dioxane, pyridine, dimethylformamide or acetonitrile (see above for more examples).

Enantiomers have identical physical and chemical properties except for the rotation of the plane of polarized light and a potential different reaction rate with other chiral compounds. The product of an asymmetric Michael reaction may however have more than one stereogenic center (see e.g. FIG. 8), In such a compound each center generally has a pair of enantiomers (unless a meso form exists) and the obtained product has diastereomers. Diastereomers may be defined as stereoisomers that are not enantiomers. Diastereomers do not merely differ in structure purely in the left and right handedness of their orientations and accordingly do not share identical properties. They have different, although similar, melting points, boiling points, solubilities, reactivity, and all other physical, chemical, and spectral properties. Relative to the main chain of a respective molecule that has diastereomers two non-hydrogen substituents at two stereoigenic centers may be on the same side of the plane defined by the main chain. This isomer can be called "syn". The other isomer, having two non-hydrogen substituents on opposite sides of the plane defined by the main chain, can be called "anti". This nomenclature is frequently used herein to address' diastereomers.

The invention is further illustrated by the following exemplary embodiments and non limiting Examples.

EXEMPLARY EMBODIMENTS OF THE INVENTION

Figure 1:
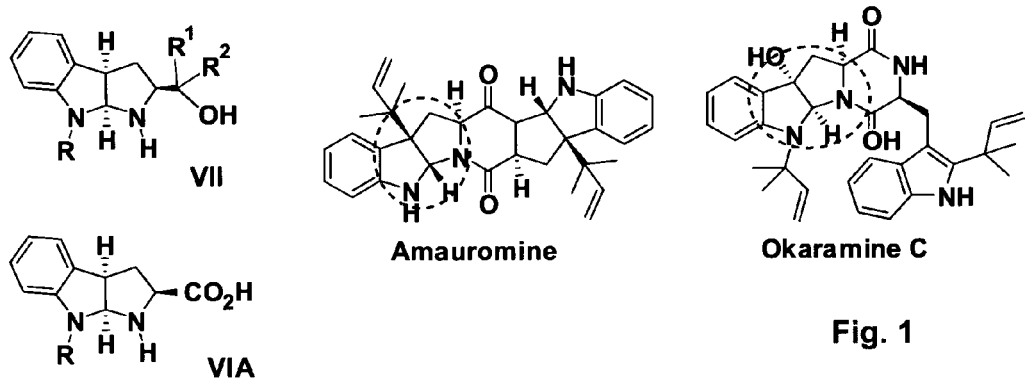
FIG. 1 compares the structures of two exemplary compounds of the invention, a compound of Formula VII and a compound of Formula (VI A), and of some natural products with hexahydropyrrolo[2,3-b]indole skeleton.

FIG. 1 structurally compares two compounds of the invention to some natural products with hexahydropyrrolo[2,3-b] indole skeleton. The hexahydropyrrolo[2,3-b]indole appears to be a key structural component of many indole alkaloids exhibiting a diverse range of biological activities (Taniguchi, M, & Hino, T, Tetrahedron (1981) 37, 1487; Bourne et al., 1991, supra; Crich & Banerjee, 2007, supra). This tricylic rigid ring system has a stable bowl-shaped conformation.

Figure 2:
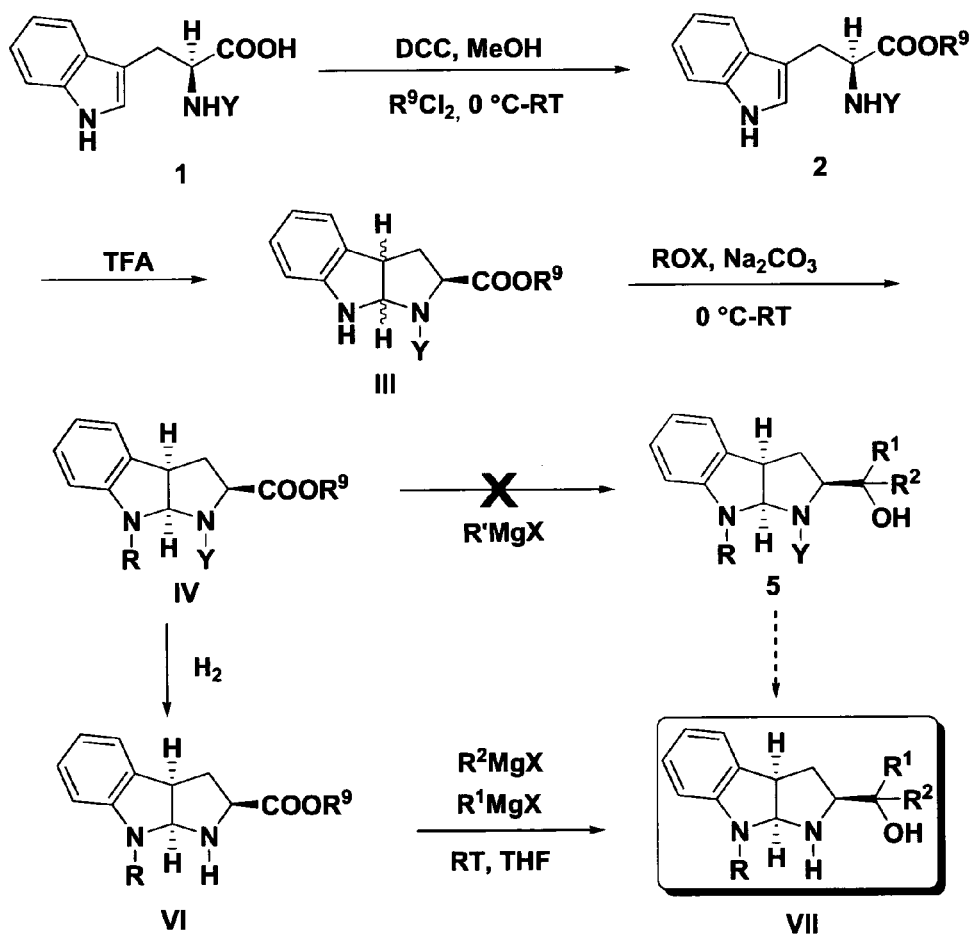
FIG. 2 depicts schematically the synthesis of a compound of Formula (VII), starting from a commercially available Na-protected L-tryptophan (1).
Figure 3:
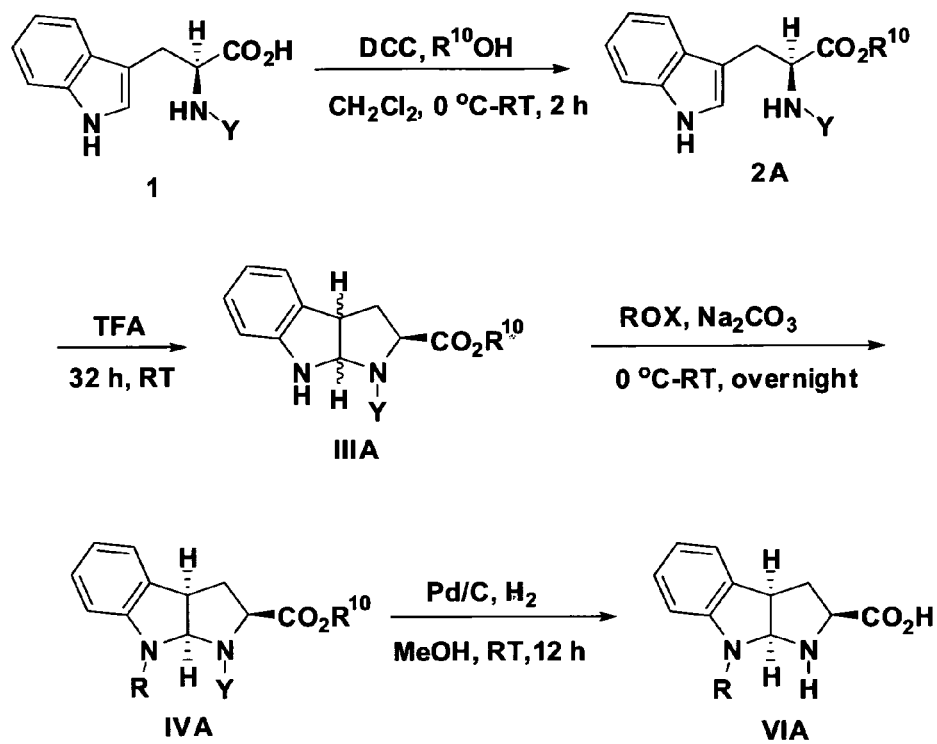
FIG. 3 depicts schematically the synthesis of a compound of Formula (VIA), starting from a commercially available Na-protected L-tryptophan (1).

FIG. 2 depicts a method of preparing a compound of Formula VII, starting from a commercially available Na-protected L-tryptophan compound (cf. also below). A related method, starting from comparable or the same L-tryptophan compound, results in the formation a compound of Formula VIA, as shown in FIG. 3.

Figure 7:
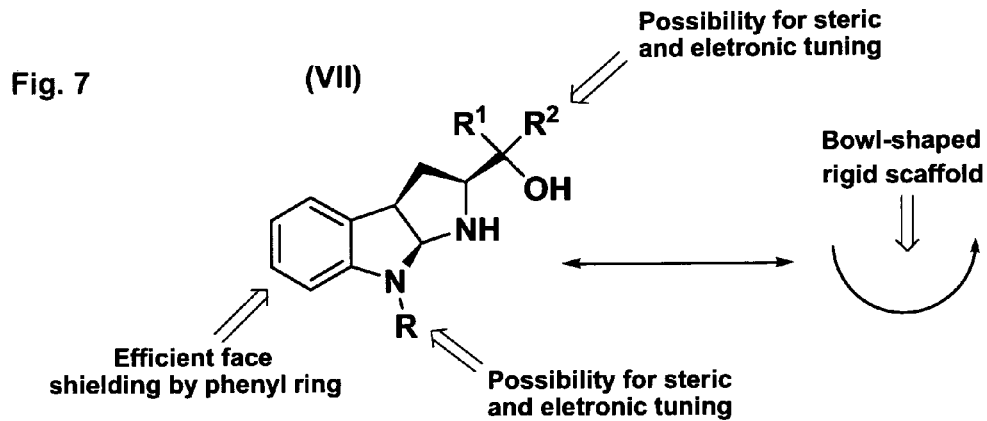
FIG. 7 illustrates the potential of design of structurally rigid chiral ligands based on the general structure of a compound of Formula (VIII).
Figure 8A:
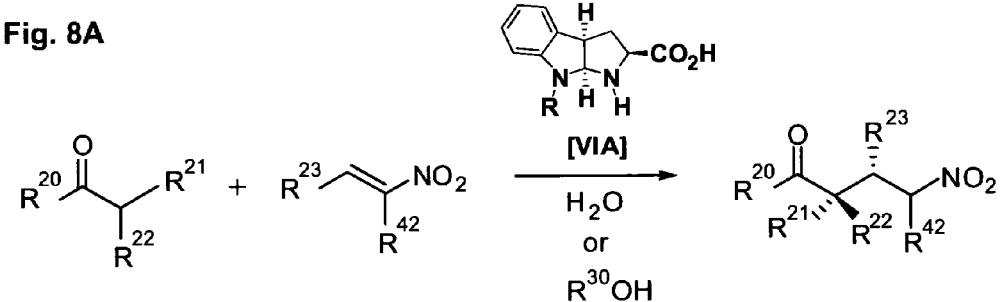
FIG. 8A illustrates the use of a compound of Formula (VI A) in a catalytic asymmetric Michael addition with the Michael acceptor being a nitro group.
Figure 8B:
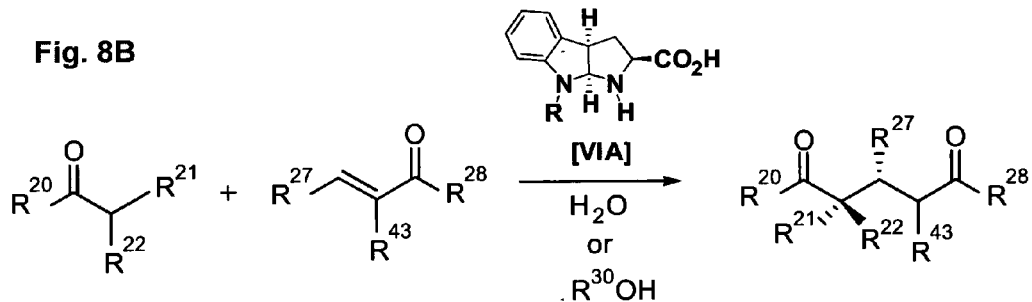
FIG. 8B illustrates the use of a compound of Formula (VI A) in a catalytic asymmetric Michael addition with the Michael acceptor being a carbonyl group.
Figure 8C:
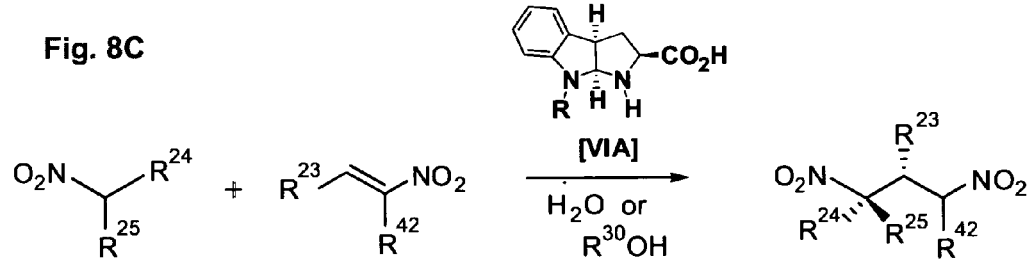
FIG. 8C illustrates the use of a compound of Formula (VI A) in a catalytic asymmetric Michael addition with the Michael acceptor being a nitro group.
Figure 8D:
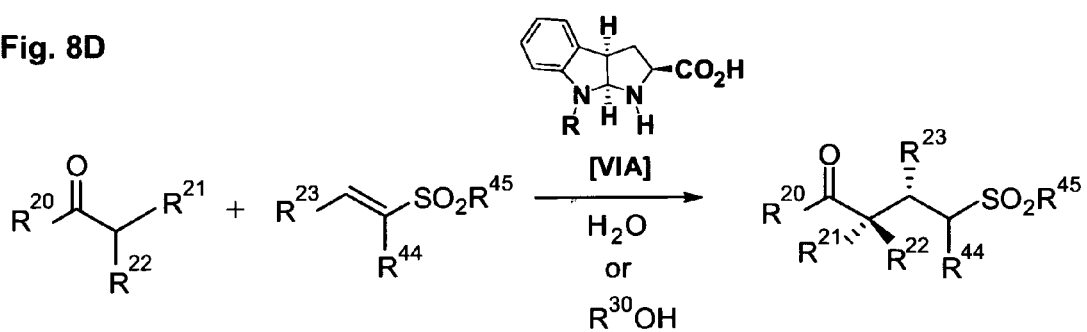
FIG. 8D depicts the use of a compound of Formula (VIA) in a catalytic asymmetric Michael addition with the Michael acceptor being a sulfonyl group.
Figure 8E:
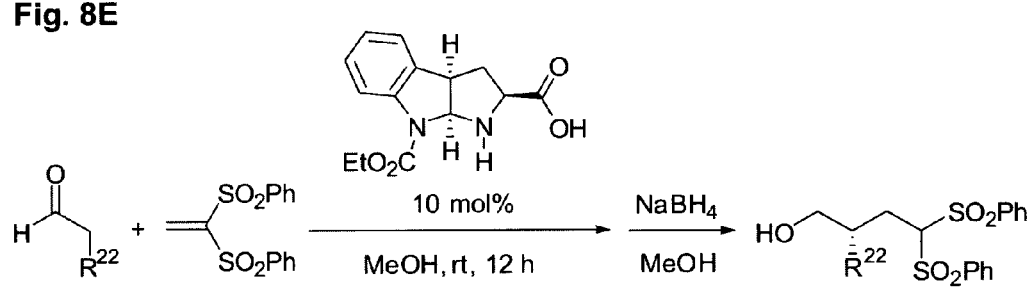
FIG. 8E and FIG. 8F illustrate experimental examples on the use of a compound of Formula (VIA) in a catalytic asymmetric Michael addition (CAN in FIG. 8F represents ceric ammonium nitrate $(NH_4)_2Ce(NO'_3)_6$).
Figure 8E:
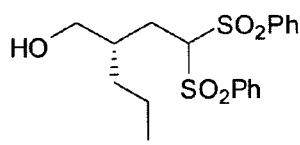
Figure 8E:
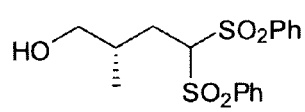
Figure 8E:
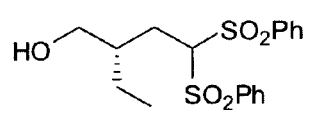
Figure 8E:
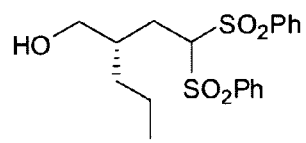
Figure 8F:
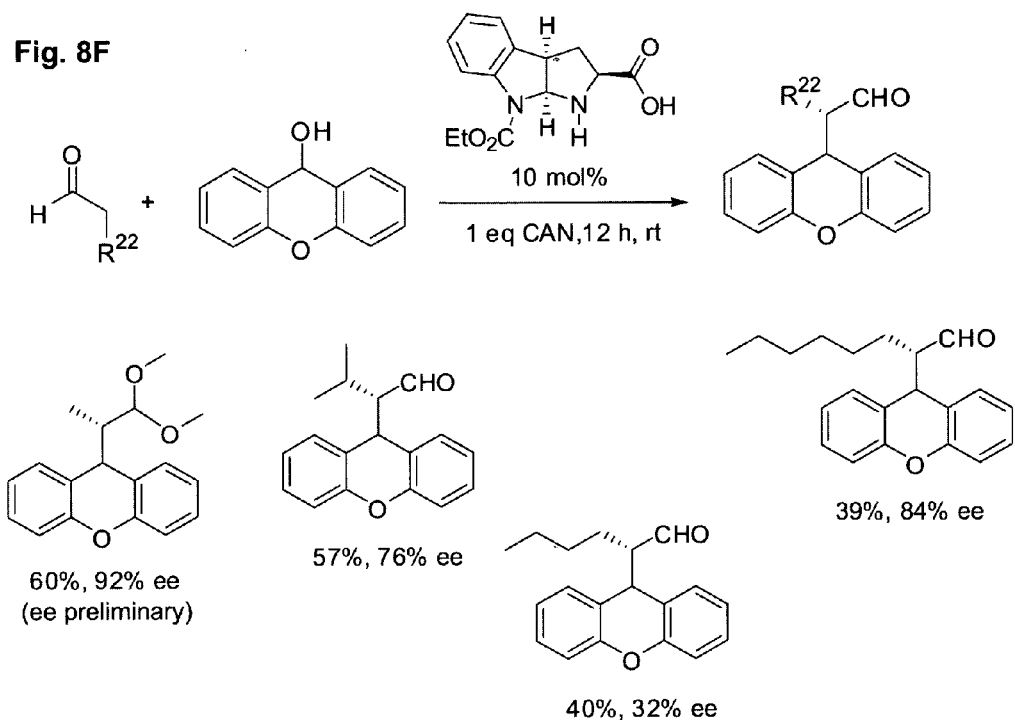
Figure 8G:
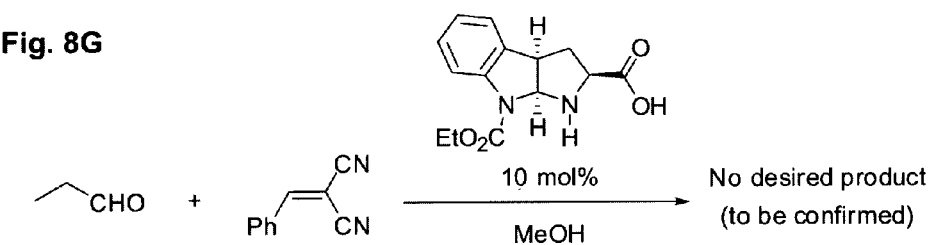
FIG. 8G depicts the preliminary result of an experimental example that may indicate an exception from the general applicability of the catalytic asymmetric Michael addition according to the invention or that may be difficult to carry out.
Figure 8H:
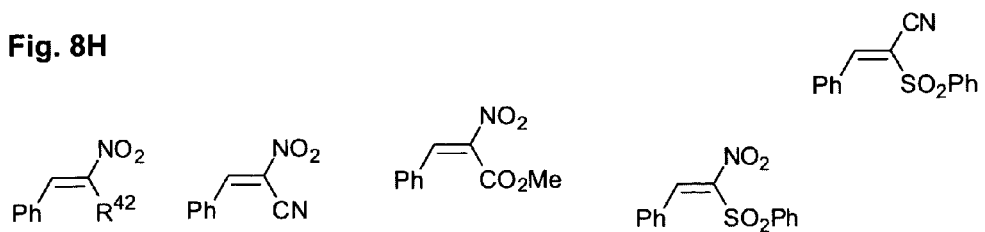
FIG. 8H depicts further examples of compounds for which preliminary data indicate their suitability as Michael acceptors.

Based on the tricyclic rigid scaffold of hexahydropyrrolo [2,3-b]indole skeleton and promising generality, a series of a new class of chiral ligands of general Formula (VII) was designed as illustrated in FIG. 7. This diversified ligand scaffold offers remarkably high tunability in both steric and electronic properties by judicious selection of the substituted R group at the amine N atom and $R^1$ and $R^2$ groups at the tertiary alcohol. Furthermore, two more stereogenic centers were incorporated as structural analogues in addition to the proline features, opening up new perspectives in ligands design.

Figure 5:
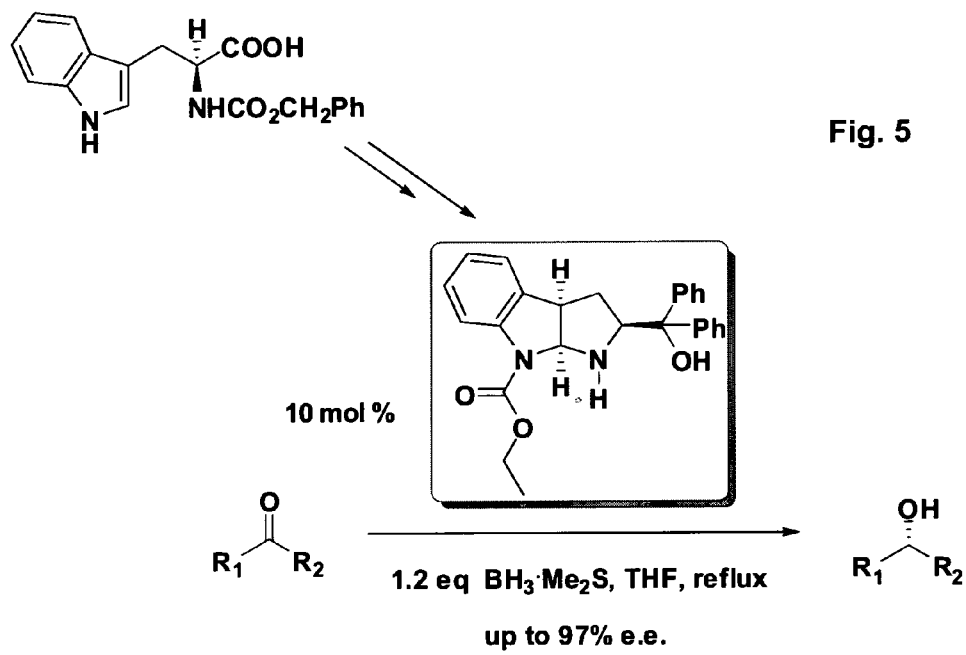
FIG. 5 illustrates the use of a compound of Formula (VII) in the asymmetric reduction of a ketone.

The chiral ligands of Formula (VII) can be used for asymmetric catalysis, as illustrated in the asymmetric reduction of ketones in FIG. 5. FIG. 11 and FIG. 12 depict examples of applications in this regard. An initial study was conducted using chiral ligand 7a with $B(OMe)_3$ to generate a borane complex in situ for the asymmetric reduction of 2-acetonaphthone at room temperature. Unfortunately, the desired product was obtained in only 37% e.e. Direct reflux with borane resulted in higher enantioselectivity (89% e.e.). Screening the different substituting groups showed ethyl carbamate protected ligand 7a to be a particularly suitable ligand for this reaction. Under the optimized reaction conditions, ligand 7a was applied to the asymmetric borane reduction of a variety of aromatic ketones (FIG. 11).

Figure 11:
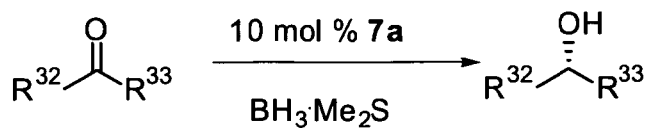
FIG. 11 is a table depicting exemplary data on the catalytic asymmetric reduction of ketones. Reactions were performed with 0.5 mmol ketone, 0.6 mmol borane, 10% of the respective ligand in 2 mL THF at reflux temperature. $^a$ Isolated yield by column chromatography. $^b$ ee determined by HPLC analysis using a Daicel Chiralcel AS-H column.
Figure 12A:
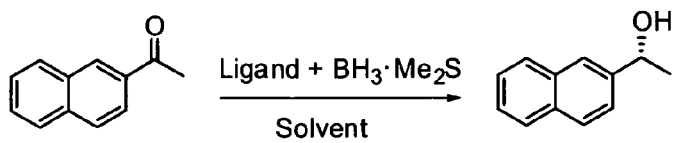
FIG. 12A is a table depicting exemplary data on optimizations of the enantioselective borane reduction of Acetonaphthone according to a use of the present invention. Reactions were performed with 0.5 mmol acetonaphthone, 0.6 mmol borane, 10% of the respective ligand in 2 mL of solvent at reflux temperature. $^a$ Isolated yield by column chromatography. $^b$ ee determined by HPLC analysis using a Daicel Chiralcel AS-H column. $^c$ Catalyst prepared by 0.1 eq ligand with 0.12 eq $B(OMe)_3$ at RT and reduction at RT. $^d$ Catalyst prepared by 0.1 eq ligand with 0.12 eq $B(OMe)_3$ at reflux condition and reduction at refulx condition. $^e$ Ligand was recycled once. $^f$ Ligand was recycled twice Ligand was recycled third time.
Figure 12B:
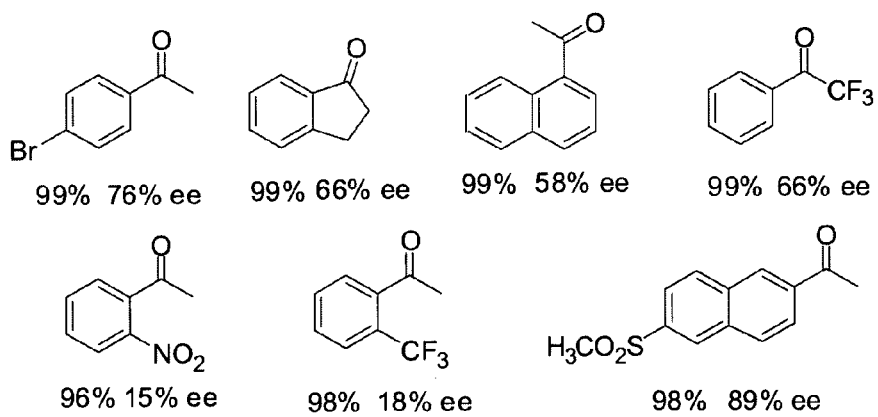
FIG. 12B depicts further examples of compounds that were tested in the enantioselective borane reduction and the observed yields and ee.

As summarized in FIG. 11, high yields and enantioselectivities are obtained for prochiral ketones containing electron-withdrawing or electron-donating groups. Especially noteworthy is that (R)-3,5-Bistrifluoromethyl phenyl ethanol (BTMP), which is an interesting chiral building block for a number of pharmaceutically interesting targets such as an NK-1 receptor antagonist (Naud, F, et al., Org. Process Res. Dev. (2007) 11, 519-523; Pollard, D., et al., Tetrahedron: Asymmetry (2006) 17, 554-559), can be obtained in 99% yield and 93% e.e. (FIG. 11, entry 10). For aliphatic ketone, moderate enantioselectivity was obtained (FIG. 11, entry 12). Notably, chiral ligand 7a can be recovered with 90% yield and reused for 3 times without loss of activity and enantioselectivity for the asymmetric reduction of 2-acetonaphthone (see in Specific Examples below). For the examples depicted in FIG. 11 reactions were performed with 0.5 mmol ketone, 0.6 mmol borane and 10% ligand in 2 mL THF at reflux temperature. [a] Isolated yield by column chromatography. [b] ee determined by HPLC analysis using Daicel Chiralcel AS-H column. For the examples depicted in FIG. 12 reactions were performed with 0.5 mmol acetonaphthone 0.6 mmol borane, 10% ligand in 2 mL of solvent at reflux temperature. [a] Isolated yield by column chromatography. [b] ee determined by HPLC analysis using a Daicel Chiralcel AS-H column. [c] Catalyst prepared by 0.1 eq ligand with 0.12 eq $B(OMe)_3$ at RT and reduction at RT. [d] Catalyst prepared by 0.1 eq ligand with 0.12 eq $B(OMe)_3$ at reflux condition and reduction at refulx condition [e] Ligand was recycled once. [f] Ligand was recycled twice [g] Ligand was recycled third time.

FIG. 8 illustrates the use of compounds of Formula VIA in asymmetric Michael reactions. On a general basis a Michael reaction is a nucleophilic addition to a vinylog carbon-carbon double bond, typically a 1,4-addition. The reaction can serve in inter alia forming a cyclic compound or extending an aliphatic chain by several carbon atoms in one step. Accordingly, such a reaction is a suitable model to illustrate the chiral capabilities of a compound. The reaction may for example be carried out by adding a carbonyl compound to an α,β-unsaturated nitro compound (FIG. 8A), by adding a carbonyl compound to an α,β-unsaturated carbonyl compound (FIG. 8B), by adding a nitro compound to an α,β-unsaturated nitro compound (FIG. 8C), or by adding a carbonyl compound to an α,β-unsaturated sulfonyl compound (FIG. 8D).

Accordingly, in FIG. 8A, FIG. 8B, FIG. 8C and FIG. 8D $R^{20}$, $R^{23}$, $R^{27}$ and $R^{28}$ may independently from each other be hydrogen, $-OR^{26}$, $-SiR^{26}$, $-SiR^{26}$, $-SR^{26}$, $-SeR^{26}$, an aliphatic group, an alicyclic group, an aromatic group, an arylaliphatic group or an arylalicyclic group. $R^{21}$, $R^{22}$, $R^{24}$, $R^{25}$, $R^{42}$ and $R^{43}$ may independently from each other be hydrogen, $-COOR^{26}$, $-COSR^{26}$, $-COSeR^{26}$, $-CONR^{26}R^{34}$, $-CN$, $-COX$, $-OR^{26}$, $-SO_2R^{26}$, $-SiR^{26}$, $-SR^{26}$, $-SeR^{26}$, an aliphatic group, an alicyclic group, an aromatic group, an arylaliphatic group or an arylalicyclic group. X is halogen. $R^{26}$ and $R^{34}$ are independent from one another one of hydrogen, an aliphatic group, an alicyclic group, an aromatic group, an arylaliphatic group or an arylalicyclic group. $R^{22}$ in FIG. 8E has the same meaning as above.

Figure 10A:
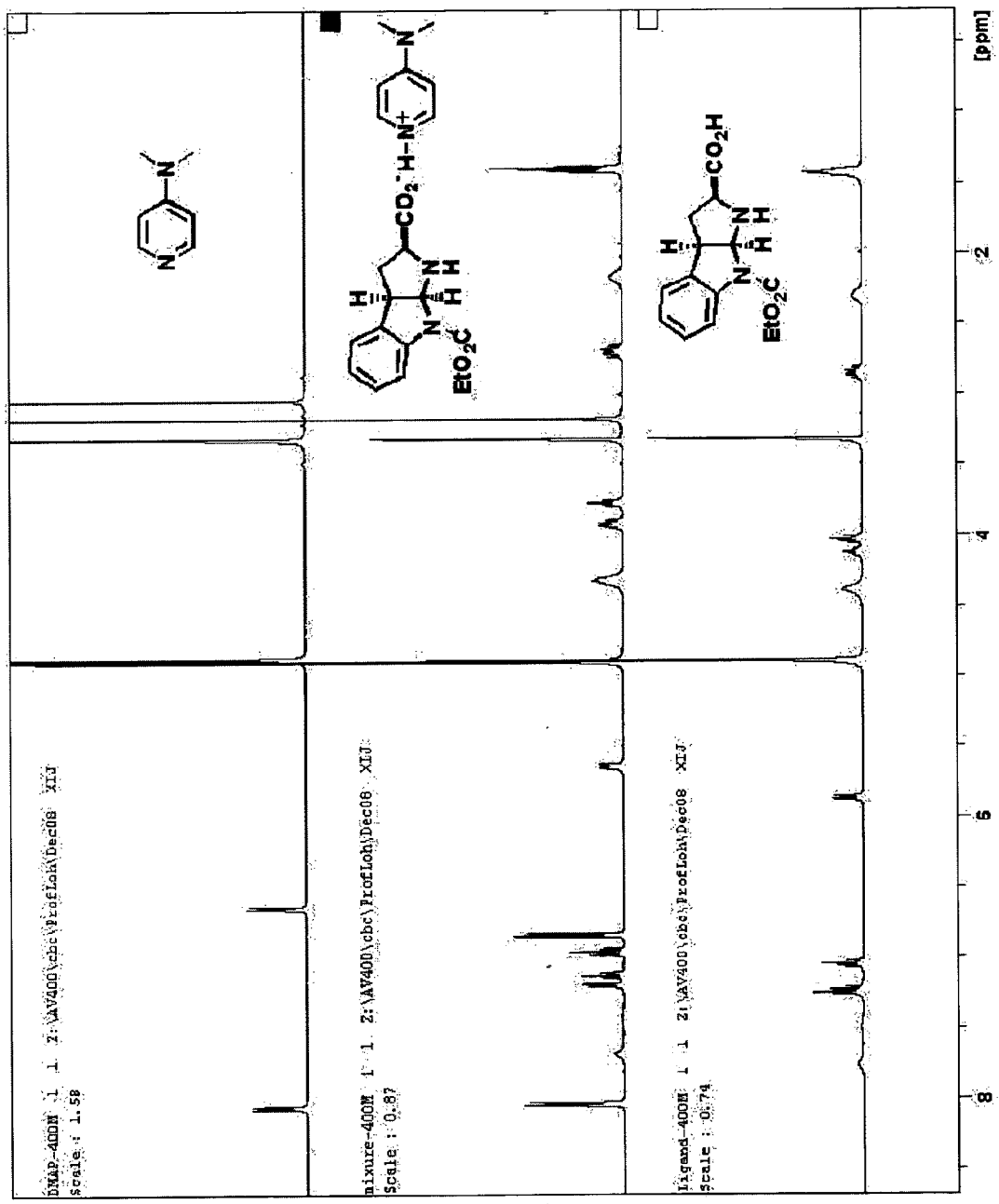
FIG. 10A depicts $^1$HNMR spectra showing the salt formation of (10) and DMAP ($CD_3OD$).
Figure 10B:
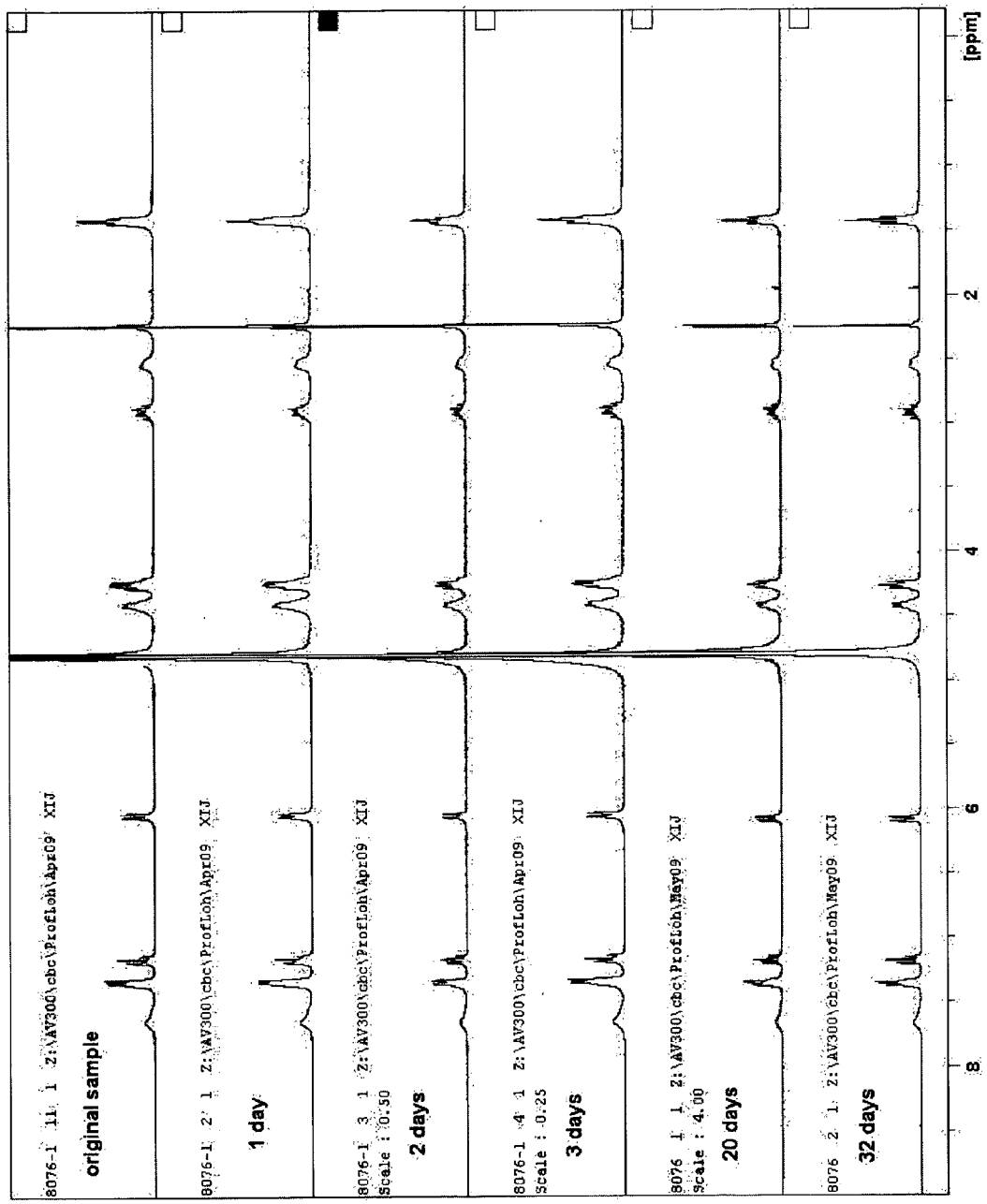
FIG. 10B depicts $^1$HNMR spectra showing the stability of catalyst (10) in water ($D_2O$). No peak change and chemical shift change occurred even after 32 days.
Figure 10C:
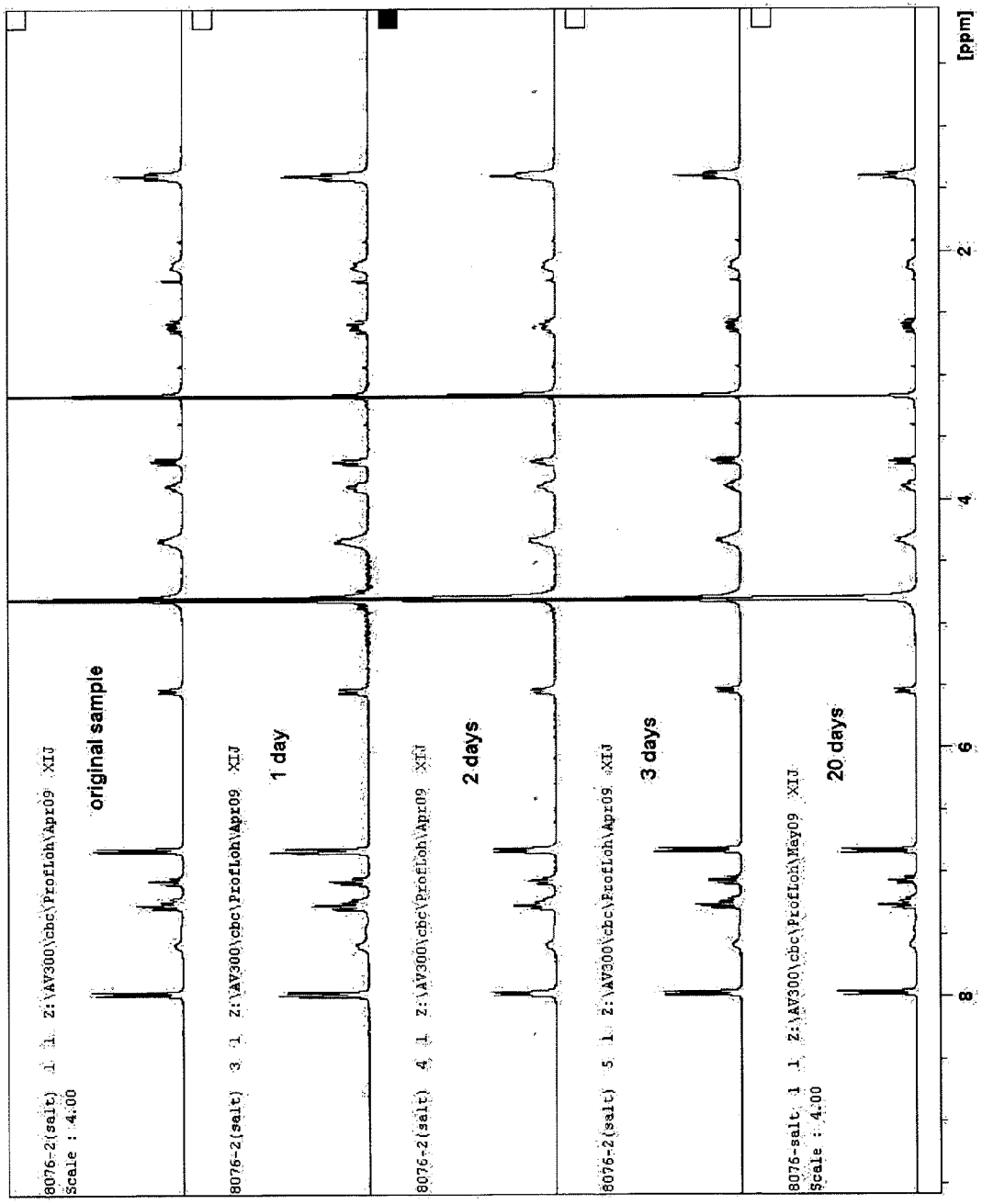
FIG. 10C depicts $^1$HNMR spectra showing the stability of catalyst (10)/DMAP in water ($D_2O$). No peak change and chemical shift change occurred even after 20 days.

FIG. 10A compares the $^1$H-NMR spectra of pure DMAP (top panel), the isolated compound of Formula VI A (lower panel), and a mixture of both compounds (center panel). Note the significant changes in chemical shift: protonation of DMAP causes signals to be moved to lower field, whereas signals of the catalyst are moved to higher field, which indicate the salt formation. As can be taken from FIG. 10B and FIG. 10C the catalyst is stable in water over extended periods of time.

FIG. 13 and FIG. 14 illustrate the catalytic asymmetric Michael addition of propanal to nitroalkenes. With chiral catalyst (10) in hand, the inventors proceeded to investigate its application for asymmetric catalysis. To demonstrate the efficiency of (10), the enantioselective Michael addition of aldehydes (for recent reviews see (a) Mossé S, & Alexakis, A, Chem. Commun. (2007) 3123. (b) Vicario, J L, et al., Synthesis (2007) 2065. (c) Tsogoeva, S B, Eur. J. Org. Chem. (2007) 1701. For some representatives, see: (e) Mase, N, et al., J. Am. Chem. Soc. (2006) 128, 4966. (f) Hayashi, Y, et al., Angew.

Chem. Int. Ed. (2005) 44, 4212. (g) Wang, W, et al., Angew. Chem. Int. Ed. (2005) 44, 1369. (h) Palomo, C E, et al., Angew. Chem. Int. Ed. (2006) 45, 5984. (i) Palomo, C, et al., Angew. Chem. Int. Ed. (2006) 45, 5984) to nitroalkenes was selected as the testing ground since nitroalkanes are versatile synthetic intermediates.

The desired product could be obtained in 86% yield and 96% e.e. in the presence of 10 mol % catalyst (10) using 2 equiv propanal at room temperature in MeOH (entry 1 of FIG. 13). In contrast, catalysts 11, 12 and 13 gave much less desirable results in MeOH (FIG. 13, entries 2-4). Without being bound by theory, these results demonstrate that it is proline's skeleton and not the hydrogen bonding interaction which account for its failure in this reaction. It was further shown that when a base such as DMAP is added, an acid-base interaction between the carboxylic acid and the amine groups leads to an ammonium salt which renders the base as the stereo controlling module, hence alleviating the need for tedious chemical structural modification. This is inline with the concept of the self-assembly of organocatalysts proposed recently [Clarke, M L, & Fuentes, J A, Angew. Chem. Int. Ed. (2007) 46, 930; Mandal T, & Zhao, C G, Angew. Chem. Int. Ed. (2008) 47, 7714-7717; Schmuck, C, & Wienand, W, J. Am. Chem. Soc. (2003) 125, 452; Gac, S L, et al., Tetrahedron (2007) 63, 10721]. More than 99% e.e. was achieved when DMAP was added and the catalyst loading could be decreased to as low as 2 mol % (entries 4 & 5 of FIG. 13). $^1$H NMR revealed that the salt was formed rapidly and quantitatively with significant chemical shift of all the protons (see FIG. 10). Both (10) and (10)/DMAP are soluble in water and are stable as shown by $^1$H NMR. More importantly, the (10)/DMAP catalyst could also catalyze the reaction in water (entry 7 of FIG. 13). Very low yield was obtained when using brine as solvent (entry 8 of FIG. 13). However, no reaction was observed using either (11)/DMAP, (12)/DMAP or (13)/DMAP, or (10) itself in pure water (entries 9-12 of FIG. 13). Next, various substrates were examined and the reaction exhibited broad applicability with respect to both the Michael acceptor and the donor. The adducts were obtained in almost optically pure form (99% ee) and with good syn diastereoselectivity. The stereochemistry was confirmed by X-ray crystal structure of one of the products (see below and FIG. 16). Both aromatic and aliphatic aldehydes, aryl- and alkyl-substituted nitroalkenes gave the desired products in good yields and excellent enantioselectivities (entries 1-11 of FIG. 14). For more bulky isobutyraldehyde, which was found to be a poor nucleophile in only 68% ee using 20 mol % diarylprolinol ether catalyst [Hayashi, Y, et al., Angew. Chem. Int. Ed. (2005) 44, 4212], were obtained with 92-95% ee with various nitrostyrenes with the respective exemplary catalyst (entries 12-14 of FIG. 14). In view of the high efficiency and high catalytic activity shown both in organic solvents and water with low catalyst loading, the catalyst (10)/DMAP can be seen as an "artificial enzyme". Most of the earlier reports for such a reaction were carried out at 0° C. or even lower temperature with 10 equiv aldehydes. Using, catalyst (10), only 2 equiv of aldehydes was employed and excellent ee could be obtained at room temperature.

Figure 4A:
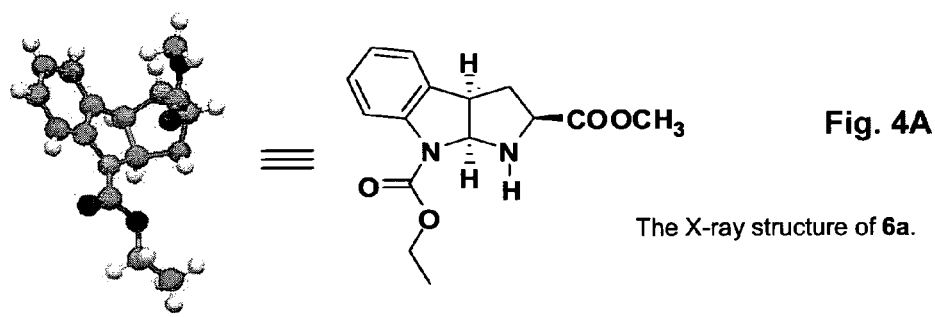
FIG. 4A depicts an illustrative example of a compound of Formula (VI) together with a schematic of its X-ray structure.
Figure 4B:
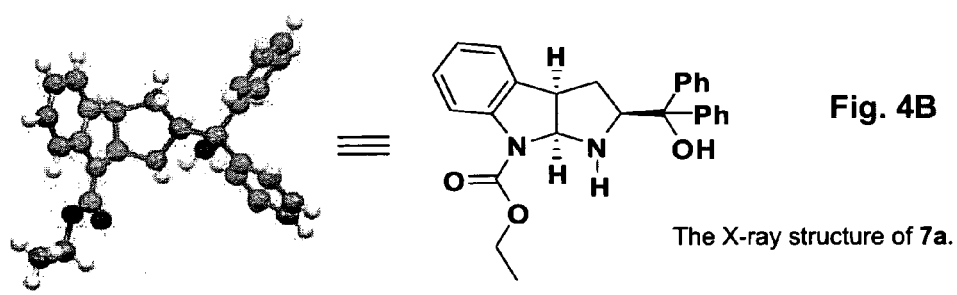
FIG. 4B depicts an illustrative example of a compound of Formula (VII) together with a schematic of its X-ray structure.

To probe the mechanism of this reaction, different possible conformers of the enamine intermediate were subjected to DFT calculation to determine the lowest energy conformation (see the Examples below for details). As expected, the ethyl carbamate group control the geometry of the enamine to adopt the syn enamine conformation (FIG. 2). From this conformer, it can be seen that at the Si face of the enamine, there are several highly electronegative atoms such as O and N which could function as hydrogen bond acceptors. Therefore when the enamine is immersed into protic solvents such as methanol and water, the Si face is expected to develop strong hydrogen-bond networks which eventually block the attack of nitrostyrene from this side (Wang, J, et al., Chem. Eur. J. (2006) 12, 4321; Chen, X-H, et al., Chem. Eur. J. (2007) 13, 689). On this basis, nitrostyrene will attack the enamine from the less hindered Re face via transition state (XXXA), where a water molecule is probably involved by forming hydrogen bonds with the $CO_2H$ group and $NO_2$ which will lead to the desired (S,R) product (FIG. 9A) (Seebach, D, & Golinski, J, Helv. Chim. Acta (1981) 64, 1413; Seebach, D, et al., Helv. Chim. Acta (1985) 68, 162). The activation energy of transition state (XXXA) is 64.61 kJ/mol lower than that of transition state (XXXB) without the water molecule as hydrogen-bond bridge. The whole system is stabilized by hydrogen bonds. The transition state (XXXC), which is consistent with Seebach's model, is also calculated and the energy of (XXXC) is 7.91 kJ/mol higher than that of the transition state (XXXA) (see the Examples below). This proposal is supported by the following experimental results: (1) methyl ester derivative 6a (cf. FIG. 4A) or the phenyl ester derivative could not catalyze the reaction with or without acid additive in MeOH or $H_2O$, which indicate the possible activation of nitrostyrene by the carboxylic acid (cf. the scheme of FIG. 13B):

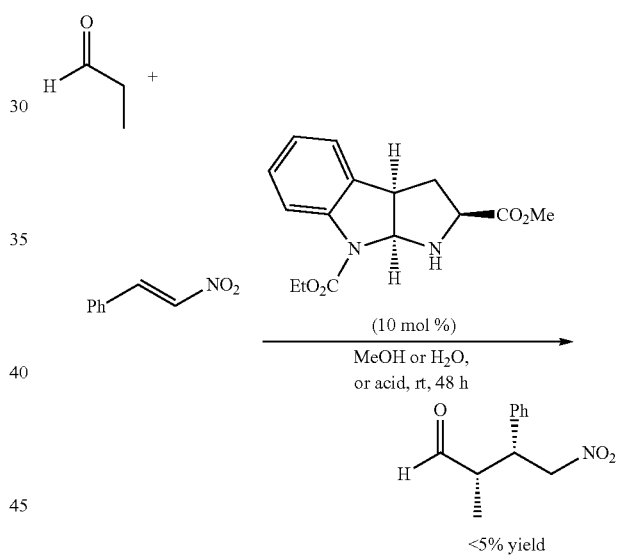

(2) the reaction was much slower in aprotic solvent such as DMSO and DMF which implies that $H_2O$ may be involved in the reaction through hydrogen-bonding interaction. Although the role of DMAP is not clear at this moment, the DMAP salt was found to improve the solubility of the catalyst and could also function as phase transfer catalyst when the reaction was carried out in water. Without being bound by theory, this structurally rigid tricyclic skeleton provides a well-organized environment for asymmetric induction as well as a hydrophobic pocket to enable this reaction to proceed smoothly in water. As for catalysts 11, 12 and 13 (cf. FIG. 13A), they could not satisfy the above criteria.

EXAMPLES

General Methods

Experiments involving moisture and/or air sensitive components were performed in oven-dried glassware under a positive pressure of nitrogen using freshly distilled solvents. Commercial grade solvents and reagents were used without further purification with the following exceptions: Dichloromethane was distilled from calcium hydride. THF was distilled from sodium and benzophenone. Hexane, ethyl acetate were fractionally distilled.

Borane-methyl sulfide complex was purchased from Aldrich. Aromatic ketone were purchased from Aldrich or prepared from Grignard reagents addition to corresponding aromatic aldehyde, then followed by standard IBX oxidation reaction. All the ketone and ligands were dried two times with anhydrous THF prior to use.

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate.

Flash chromatography was performed using Merck silica gel 60 with freshly distilled solvents. Columns were typically packed as slurry and equilibrated with the appropriate solvent system prior to use.

Infrared spectra were recorded on a Bio-Rad FTS 165 FTIR spectrometer. The oil samples were examined under neat conditions.

High Resolution Mass (HRMS) spectra were obtained using Finnigan MAT95XP GC/HRMS (Thermo Electron Corporation).

Proton nuclear magnetic resonance spectra ($^1$H NMR) were recorded on a Bruker Avance DPX 300 and Bruker AMX 400 spectrophotometer (CDCl$_3$ as solvent). Chemical shifts for $^1$H NMR spectra are reported as δ in units of parts per million (ppm) downfield from SiMe$_4$ (δ0.0) and relative to the signal of chloroform-d (δ 7.2600, singlet). Multiplicities were given as: s (singlet); d (doublet); t (triplet); q (quartet); dd (doublets of doublet); ddd (doublets of doublets of doublet); dddd (doublets of doublets of doublets of doublet); dt (doublets of triplet); or m (multiplets). The number of protons (n) for a given resonance is indicated by nH. Coupling constants are reported as a J value in Hz. Carbon nuclear magnetic resonance spectra ($^{13}$C NMR) are reported as δ in units of parts per million (ppm) downfield from SiMe$_4$ (δ 0.0) and relative to the signal of chloroform-d (δ 77.0, triplet). The proportion of diastereomers and geometric isomers was determined from the integration of $^1$H NMR and $^{13}$C NMR spectra.

Enantioselectivities were determined HPLC analysis employing a Daicel Chiracel column at 25° C. Optical rotation was measured using a JASCO P-1030. Polarimeter equipped with a sodium vapor lamp at 589 nm. Concentration is denoted as c and was calculated as grams per deciliters (g/100 mL) whereas the solvent. Absolute configuration of the products was determined by comparison with known compounds. X-ray crystallogphy analysis was performed on Bruker X8 APEX X-Ray diffractometer.

General Procedure for the Catalytic Asymmetric Michael Addition of Aldeydes to Nitrostyrene To a 4 mL sample vial equipped with a magnetic stirring bar, the mixture of catalyst (2.7 mg, 0.01 mmol), DMAP (1.2 mg, 0.01 mmol), nitroalkene (0.2 mmol) aldehyde (0.4 mmol) were added followed by MeOH or water (0.5 mL) at room temperature. The reaction mixture was stirred for the time indicated in FIG. 14, and then it was directly purified by preparative TLC (Hexane/EA, 4/1) to afford the product as inseparable isomers. Both enantiomeric excess and diastereomeric ratio (syn/anti) were determined by HPLC using chiral AS-H, AD-H or OD-H columns unless otherwise stated in comparison with the literature reported values.

General Procedure for the Enantioselective Ketone Reduction

To an oven-dried 10 mL round-bottom flask equipped with a magnetic stirring bar was added new chiral ligand 7a (0.07 mmol, 0.10 equiv). The ligand was azeotropically dried with anhydrous THF twice (2 mL×2) prior to the addition of 1.5 mL of THF. Then BH$_3$Me$_2$S (0.087 mmol, 10 mol/L) was added under nitrogen at room temperature and the mixture was stirred at 80° C. for 3 h. A solution of ketone (0.7 mmol) in dry THF (0.5 mL) was added dropwise by syringe pump over a period of 1 h at reflux temperature. Then the reaction mixture was cooled and quenched by dropwise addition of methanol (5 mL). After concentration by rotatory evaporation, the product was purified by column chromatography on silica gel (hexane-ethyl acetate 5:1) to afford the corresponding secondary alcohol. The enantiomeric excess was determined by chiral HPLC analysis employing a Daicel Chiracel column.

A general scheme of the preparation and characterization of a tryptophan derivative is shown in FIG. 2. FIG. 15 depicts further examples, showing the synthesis of chiral ligands 7a-h.

Synthesis of (S)-N-benzyloxycarbonyl-L-tryptophan methyl ester (2a)

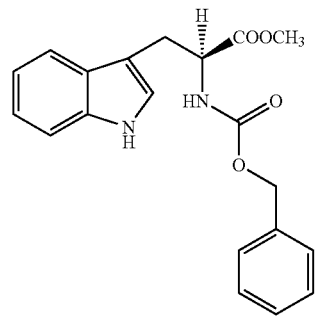

2

To a stirred suspension of (S)—N-benzyloxycarbonyl-L-tryptophan 1a (2.45 g, 7.2 mmol) in 10 ml anhydrous CH$_2$Cl$_2$, was added DMAP (0.1 g, 0.82 mmol) and methanol (0.28 g, 11.8 mmol). At 0° C., DCC in CH$_2$Cl$_2$ solution was slowly added to the mixture and then it was allowed to warm to room temperature and stirred overnight. After twice filtration and evaporation, the residue was purified by flash column chromatography (n-hexane/EA, 4:1 to 2:1) and afforded the desired product (S)-2a as a colourless oil (2.5 g, 98%).

$R_f$=0.19 (EA:Hexane=1:2)

$^1$H NMR (300 MHz, CDCl$_3$): δ8.94 (br, 1H), 7.49 (d, J=7.7 Hz, 1H), 7.25-6.98 (m, 9H), 6.81 (s, 1H), 5.84 (d, J=8.7 Hz, 1H), 4.98 (d, J=3.2 Hz, 2H), 4.68 (q, J=7.3 Hz, 1H), 3.25 (s, 3H), 3.21 (m, 2H);

$^{13}$C NMR (75 MHz, CDCl$_3$): δ 172.2, 155.9, 141.8, 136.8, 134.9, 128.6, 127.8, 126.9, 123.4, 122.3, 120.0, 118.4, 112.1, 109.4, 67.0, 65.1, 55.1;

FTIR (KBr, neat): ν 1707, 1508, 1456, 1436, 1215, 742 cm$^{-1}$;

HRMS (EI) calcd. for $C_{20}H_{20}O_4N_2$ 352.1418. found $[M]^+$ 352.1425.

(2S)-1-benzyl-2-methyl-3,3a,8,8a-tetrahydropyrrolo[2,3-b]indole-1,2(2H)-dicarboxylate (3a)

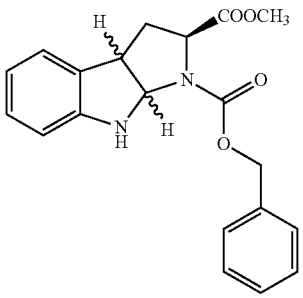

N-benzyloxycarbonyl-L-tryptophan methyl ester (S)-2 (1.34 g, 3.8 mmol) was dissolved in 5 ml TFA and stirred for two days, then the solution was added dropwise to a vigorously stirred two phase system consisting of saturated 100 ml $Na_2CO_3$ and 100 ml $CH_2Cl_2$ at 0° C. The two phase was separated and the aqueous solution was extracted with $CH_2Cl_2$ (30 ml×3). The combined organic phases were washed with brine and dried with anhydrous $MgSO_4$ and purified with flash column chromatography (EA/Hexane, 1:7-1:4) to give the product as colorless oil (0.8 g, 60%) which rapidly darkened on standing in air.

Major Isomer:

$R_f$=0.32 (EA:Hexane=1:4);

$^1$H NMR (400 MHz, $CDCl_3$): δ 7.42-7.24 (m, 5H), 7.05-6.99 (m, 2H), 6.68 (q, J=8.9 Hz, 1H), 6.60 (d, J=7.6 Hz, 1H), 5.59 (t, J=6.6 Hz, 1H), 5.30-5.09 (m, 2H), 3.92 (q, J=6.5 Hz, 1H), 3.19 (s, 1H, $CH_3$), 3.10 (s, 2H, $CH_3$), 2.65-2.54 (m, 2H);

$^{13}$C NMR (100 MHz, $CDCl_3$): δ 172.0, 154.6, 150.1, 136.2, 129.0, 128.6, 128.4, 127.6, 127.5, 127.4, 127.0, 124.0, 118.7, 109.1, 77.4, 67.0, 59.1, 51.9, 45.0, 34.0;

FTIR (KBr, neat): v 1732, 1712, 1602 $cm^{-1}$,

HRMS (EI) calcd. for $C_{20}H_{20}O_4N_2$ 352.1418. found $[M]^+$ 352.1413.

(2S,3aR,8aS)-1-benzyl-8-ethyl-2-methyl-3,3a-dihydropyrrolo[2,3-b]indole-1,2,8(2H,8aH)-tricarboxylate (4a)

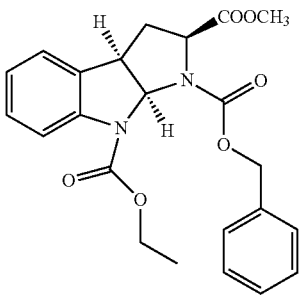

(2S)-1-benzyl-2-methyl-3,3a,8,8a-tetrahydropyrrolo[2,3-b]indole-1,2(2H)-dicarboxylate 3a (0.8 g, 2.27 mmol) was dissolved in 5 ml THF, then $Na_2CO_3$ (0.36 g, 3.40 mmol) and 5 ml $H_2O$ was added. At 0° C., ethyl chloroformate (0.22 ml, 2.26 mmol) was slowly added to the solution and stirred overnight. 10 ml water was added and the aqueous solution was extracted with EA (5 ml×3). The combined organic phases were washed with brine and dried with anhydrous $MgSO_4$ and purified with flash column chromatography (EA/Hexane, 1:4-1:2) to afford the desired product as colorless oil (0.77 g, 80%).

$R_f$=0.43 (EA:Hexane=1:2);

$^1$H NMR (300 MHz, $CDCl_3$): δ7.66 (d, J=7.5 Hz, 1H), 7.38-7.10 (m, 7H), 6.99 (t, J=7.4 Hz, 1H), 6.49 (d, J=6.5 Hz, 1H), 5.19 (s, 2H), 4.67 (d, J=8.5 Hz, 1H), 4.33-4.17 (br, 1H), 4.00 (t, J=7.1 Hz, 1H), 3.13 (s, 3H), 2.65-2.43 (m, 2H), 1.35-1.23 (br, 3H);

$^{13}$C NMR (75 MHz, $CDCl_3$): δ 171.1, 153.6, 152.9, 142.2, 135.9, 130.8, 128.2, 128.0, 127.9, 127.7, 127.5, 127.5, 123.5, 122.9, 116.2, 77.1, 66.7, 61.3, 58.9, 51.4, 44.5, 33.2, 13.9;

FTIR (KBr, neat): v 1728, 1712, 1697, 1604, 1483 $cm^{-1}$;

HRMS (EI) calcd. for $C_{23}H_{24}O_6N_2$ 424.1629. found $[M]^+$ 424.1619.

(2S,3aR,8aS)-8-ethyl-2-methyl-1,2,3,3a-tetrahydropyrrolo[2,3-b]indole-2,8(8aH)-dicarboxylate (6a)

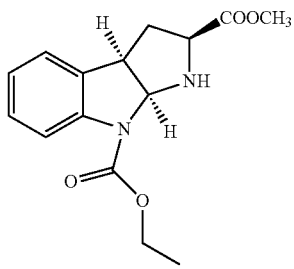

(2S,3aR,8aS)-1-benzyl-8-ethyl-2-methyl-3,3a-dihydropyrrolo[2,3-b]indole-1,2,8(2H,8aH)-tricarboxylate 4a (0.77 g, 1.82 mmol) was dissolved in 5 ml $CH_3OH$ and 10% Pd/C (0.19 g, 0.18 mmol) was added to the solution and stirred overnight under $H_2$ balloon at RT. When TLC showed the full depletion of the starting material, the suspension was filtered on celite and the solvent was evaporated, the residue was purified with flash column chromatography (EA/hexane, 1:4-1:2) to give the product as colorless oil (0.48 g, 90%).

Major Isomer:

$R_f$=0.62 (EA:Hexane=1:2);

$^1$H NMR (300 MHz, $CDCl_3$): δ 7.86 (d, J=7.5 Hz, 0.5H), 7.47-7.27 (m, 0.5H), 7.24 (d, J=7.4 Hz, 2H), 7.05 (t, J=7.5 Hz, 1H), 5.80 (d, J=6.8 Hz, 1H), 4.45 (q, J=6.6 Hz, 2H), 3.99 (d, J=7.6 Hz, 2H), 3.41 (s, 3H), 2.73-2.64 (m, 1H), 2.49 (d, J=11.2 Hz, 1H), 1.50 (t, J=6.0 Hz, 3H);

$^{13}$C NMR (75 MHz, $CDCl_3$): δ 174.1, 152.5, 128.7, 127.8, 126.1, 124.5, 122.8, 114.3, 78.4, 60.9, 57.8, 50.7, 43.7, 34.8, 15.1;

FTIR (KBr, neat): v 1732, 1712, 1602, 1487 $cm^{-1}$;

HRMS (EI) calcd. for $C_{15}H_{18}O_4N_2$ 290.1261. found $[M]^+$ 290.1249.

(2S,3aR,8aS)-ethyl 2-(hydroxydiphenylmethyl)-1,2,3,3a-tetrahydropyrrolo[2,3-b]-indole-8(8aH)-carboxylate (7a)

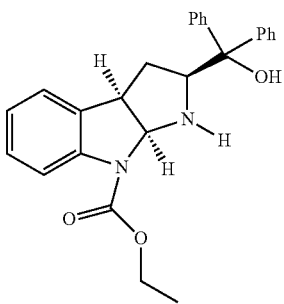

7a

At 0° C., to a solution of (2S,3aR,8aS)-8-ethyl-2-methyl-1,2,3,3a-tetrahydropyrrolo[2,3-b]indole-2,8(8aH)-dicarboxylate 6 (0.48 g, 1.65 mmol) in 5 ml THF was added dropwise 2M phenyl magnesium chloride (2.1 ml, 4.2 mmol) in THF solution and stirred for half an hour, then quenched by 5 ml water. The two phase was separated and the aqueous solution was extracted with EA (5 ml×3). The combined organic phases were washed with brine and dried with anhydrous MgSO4 and purified with flash column chromatography (EA/hexane, 1:10) to give the product as colorless solid (205 mg, 30%).

$R_f$=0.85 (EA:Hexane=1:6);

$^1$H-NMR (400 MHz, CDCl$_3$): δ 7.56 (d, J=7.6 Hz, 2H), 7.44 (d, J=7.4 Hz, 2H), 7.32-7.14 (m, 7H), 7.03 (d, J=7.2 Hz, 1H), 6.94 (t, J=9.3 Hz, 1H), 5.65 (br, 1H), 4.47 (t, J=6.6 Hz, 1H), 4.26 (br, 2H), 4.04 (br, 1H), 3.74 (q, J=7.2 Hz, 1H), 2.04 (br, 1H), 1.84-1.76 (m, 1H), 1.43-1.32 (m, 1H), 1.27-1.11 (m, 3H);

$^{13}$C-NMR (100 MHz, CDCl$_3$): δ 154.0, 147.2, 144.6, 128.4, 128.0, 127.9, 126.9, 126.6, 125.7, 125.3, 124.6, 124.2, 122.9, 114.9, 75.7, 63.8, 44.1, 32.8, 22.7, 14.1;

FTIR (KBr, neat): v 1699, 1487, 1381, 1307 cm$^{-1}$,

HRMS (EI) calcd. for C$_{26}$H$_{26}$O$_3$N$_2$ 414.1938. found [M]$^+$ 414.1915.

Synthesis of (S)-benzyl 2-(benzyloxycarbonylamino)-3-(1H-indol-3-yl)propanoate (2)

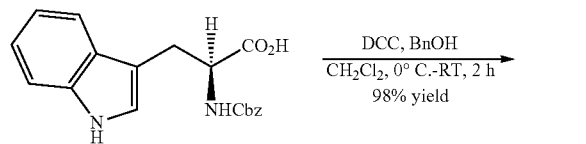

To a stirred suspension of (S)-(1) (2.45 g, 7.2 mmol) in 10 ml anhydrous CH$_2$Cl$_2$, was added DMAP (88 mg, 0.72 mmol) and benzyl alcohol (1.28 g, 11.8 mmol). DCC (1.48 g, 7.2 mmol) in 5 mL CH$_2$Cl$_2$ was slowly added to the mixture at 0° C. and the mixture was stirred overnight with slow warm to RT. The white precipitate was filtered, then remove the solvent to afford the product as colourless oil (3 g, 98%).

$[α]_D^{20}$=50 (c=1.0, CHCl$_3$, 365 nm).

$R_f$=0.29 (EA:Hexane=1:2);

$^1$H NMR (400 MHz, CDCl$_3$): δ 8.26 (br, 1H), 7.56 (d, J=8.0 Hz, 1H), 7.41-7.33 (m, 9H), 7.26-7.20 (m, 3H), 7.12 (t, J=8.0 Hz, 1H), 6.76 (d, J=2.0 Hz, 1H), 5.47 (d, J=8.0 Hz, 1H), 5.18-5.10 (m, 4H), 4.82 (q, J=8.0 Hz, 1H), 3.34 (d, J=5.1 Hz, 2H);

$^{13}$C NMR (100 MHz, CDCl$_3$): δ 171.8, 155.8, 136.1, 136.0, 135.1, 128.5, 128.4, 128.3, 128.0, 127.5, 127.4, 126.9, 122.9, 122.0, 119.5, 118.5, 111.2, 109.4, 67.1, 66.8, 54.6, 27.8;

FTIR (neat): v 3395, 3343, 1742, 1458, 1377, 721 cm$^{-1}$,

HRMS (ESI) calcd. for C$_{20}$H$_{20}$O$_4$N$_2$ 429.1814 [M+H]$^+$. found 429.1821 [M+H]$^+$.

Synthesis of (2S,3aR,8aR)-dibenzyl 3,3a,8,8a-tetrahydropyrrolo[2,3-b]indol-1,2(2H)-dicarboxylate (3)

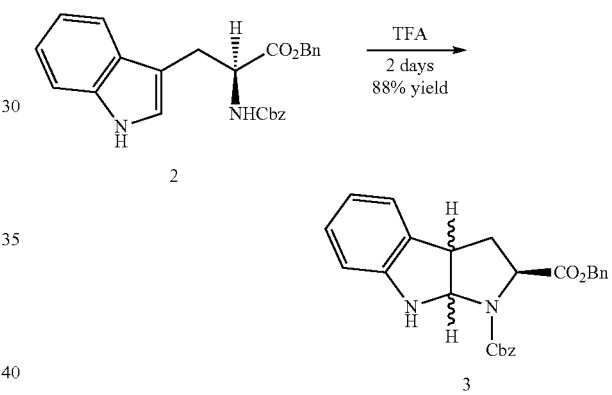

N-benzyloxycarbonyl-L-trptophan benzyl ester (2) (1.18 g, 2.75 mmol) was dissolved in 5 ml TFA and stirred for two days, then the solution was added dropwise to a vigorously stirred two-phase system consisting of 100 mL saturated Na$_2$CO$_3$ and 100 mL CH$_2$Cl$_2$, The two phase was separated and the aqueous solution was extracted with CH$_2$Cl$_2$ (30 mL×3). The combined organic phases were washed with brine and dried with anhydrous MgSO$_4$ and purified with column chromatography (ethyl acetate/hexane=1:7-1:4) to give the product as colorless oil (1.04 g, 88%) which rapidly darkened on standing in air.

Major Isomer:

$R_f$=0.34 (EA:Hexane=1:2);

$^1$H NMR (400 MHz, CDCl$_3$): δ 7.40-7.19 (m, 8H), 7.13-1.12 (m, 1H), 7.07-7.04 (m, 1H), 7.02-6.97 (m, 2H), 6.67 (t, J=8.0 Hz, 1H), 6.49 (d, J=8.0 Hz, 1H), 5.60 (d, J=8.0 Hz, 1H), 5.24 (s, 1H), 5.04 (d, J=43, 12 Hz, 1H), 4.73 (d, J=12 Hz, 1H), 4.56 (dd, J=7.6, 2.3 Hz, 1H), 4.32 (d, J=12.3 Hz, 1H), 3.90 (q, J=6.5 Hz, 1H), 2.66-2.53 (m, 2H);

$^{13}$C NMR (100 MHz, CDCl$_3$): δ 171.3, 154.7, 149.9, 135.5, 128.6, 128.4, 128.3, 128.0, 128.0, 128.0, 127.9, 127.9, 127.8, 124.0, 118.7, 109.1, 77.4, 67.1, 66.7, 59.1, 45.0, 34.4;

$[α]_D^{20}$=52.9 (c=1.8, CHCl$_3$, 365 nm);

FTIR (neat): v 3032, 2953, 1751, 1701, 1610, 1416, 731 cm$^{-1}$

HRMS (ESI) calcd. for $C_{20}H_{20}O_4N_2$ 429.1814 $[M+H]^+$. found 429.1818 $[M+H]^+$.

Synthesis of (2S,3aR,8aS)-1,2-dibenzyl 8-ethyl 3,3a-dihydropyrrolo[2,3-b]indole-1,2,8(2H,8aH)-tricarboxylate (4)

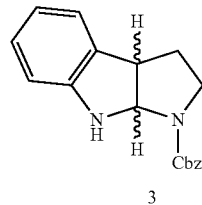

3

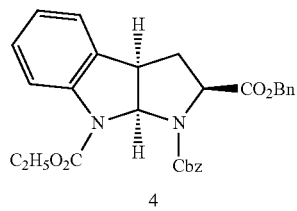

4

(S)-(3) (0.11 g, 0.26 mmol) was dissolved in 6 mL THF, then $Na_2CO_3$ (1.06 g, 10 mmol) in 6 ml $H_2O$ was added. Ethyl chloroformate (0.25 mL, 2.6 mmol) was slowly added to the solution at 0° C. After stirring overnight, 10 ml water was added and the obtained two phases were separated. The aqueous solution was extracted with EA (5 mL×3). The combined organic phases were washed with brine and dried with anhydrous $MgSO_4$ and purified with column chromatography (ethyl acetate/hexane=1:5-1:2) to give the product as colorless oil (0.11 g, 86%).

$R_f$=0.24 (EA:Hexane=1:2);

$^1$H NMR (300 MHz, $CDCl_3$): δ 7.53 (br, 1H), 7.27-7.23 (m, 8H), 7.14 (t, J=8.3 Hz, 1H), 7.09-7.04 (m, 4H), 6.94 (t, J=7.5 Hz, 1H), 6.47 (d, J=6.2 Hz, 1H), 5.14 (q, J=15 Hz, 2H), 4.72-4.68 (m, 2H), 4.36 (d, J=12.6 Hz, 1H), 3.96 (t, J=6.8 Hz, 1H), 2.64-2.49 (m, 2H), 1.26-1.20 (m, 3H);

$^{13}$C NMR (75 MHz, $CDCl_3$): δ 170.9, 154.1, 153.5, 142.7, 136.4, 135.3, 131.2, 128.8, 128.6, 128.5, 128.4, 128.1, 127.9, 127.6, 124.0, 123.5, 116.9, 67.4, 66.8, 61.9, 59.6, 45.0, 33.9, 14.5; $[α]_D^{20}$=-10.8 (c=1.04, $CHCl_3$, 365 nm);

FTIR (neat): ν 3018, 2957, 1717, 1605, 1483, 740 cm$^{-1}$;

HRMS (ESI) calcd. for $C_{29}H_{29}O_6N_2$ 501.2026 $[M+H]^+$. found 501.2018 $[M+H]^+$.

Synthesis of (2S,3aR,8aS-dibenzyl 8-ethoxycarbonyl 1,2,3,3a,8,8a-hexahydropyrrolo[2,3-b]indole-2-carboxylic acid (10)

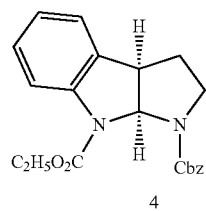

4

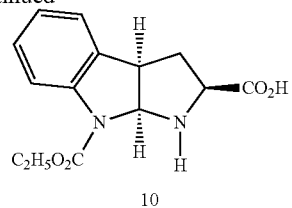

10

4 (5 g, 10 mmol) was dissolved in 20 mL methanol, and Pd/C (106 mg, 1 mmol) was added to the solution. After stirring overnight with the $H_2$ balloon, the obtained mixture was filtered with celite and the solvent evaporated to give the product as colorless oil. Then $CH_2Cl_2$ was added, the white solid precipitated and a further filtration gave the product as white solid (2.76 g, 100%).

$R_f$=0.59 ($CH_2Cl_2$:$CH_3OH$=1:4);

$^1$H NMR (400 MHz, $CD_3OD$): δ 7.77, 7.52 (br, 1H), 7.26-7.20 (m, 2H), 7.04 (t, J=7.6 Hz), 5.86 (d, J=8.6 Hz, 1H), 4.38 (br, 2H), 4.14-4.09 (m, 1H), 4.02 (t, J=7.6 Hz, 1H), 2.88-2.80 (m, 1H), 2.31-2.27 (m, 1H), 1.41 (t, J=6.7 HZ, 3H);

$^{13}$C NMR (100 MHz, $CD_3OD$): δ 172.5, 152.1, 140.9, 131.5, 128.1, 124.2, 123.0, 113.6, 77.9, 62.0, 60.0, 44.0, 35.1, 13.4; $[α]_D^{20}$=-15.9 (c=0.4, $CH_3OH$, 365 nm);

FTIR (neat): ν 3177, 2725, 1721, 1629, 1570, 1462, 1377, 760, 721 cm$^{-1}$;

HRMS (ESI) calcd. for $C_{14}H_{17}O_4N_2$ 277.1188 $[M+H]^+$. found $[M]^+$ 277.1188 $[M+H]^+$.

(2S,3R)-2-Methyl-4-nitro-3-phenylbutanal

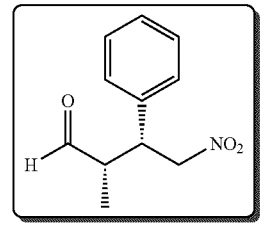

The title compound was prepared from propionaldehyde and (E)-(2-nitrovinyl)benzene according to the general procedure. Both enantiomeric excess and diastereomeric ratio were determined by HPLC withan OD-H column at 210 nm (2-propanol:hexane=10:90), 1.0 mL/min; major enantiomer $t_{major}$=22.06 min, minor enantiomer $t_{minor}$=30.05 min. $[α]_D^{20}$=-28.8 (c=2.2, $CHCl_3$).

$R_f$=0.18 (EA:Hexane=1:4);

$^1$H NMR (300 MHz, $CDCl_3$): δ 9.72 (d, J=1.5 Hz, 0.85H) (syn isomer), 9.72 (d, J=1.5 Hz, 0.15H) (anti isomer), 7.37-7.29 (m, 3H), 7.22-7.16 (m, 2H), 4.83-4.65 (m, 2H), 3.87-3.77 (m, 1H), 2.87-2.72 (m, 1H), 1.21 (d, J=7.3 Hz, 0.5H) (anti isomer), 1.01 (d, J=7.3 Hz, 2.5H) (syn isomer);

$^{13}$C NMR (75 MHz, $CDCl_3$): δ 202.3, 136.6, 129.1, 128.1, 78.1, 48.4, 44.0, 12.1;

IR (thin film) ν/cm$^{-1}$: 3030, 2970, 2931, 1724, 1603, 1552, 1454, 1379, 758, 702;

(2S,3R)-3-(4-Bromophenyl)-2-methyl-4-nitrobutanal

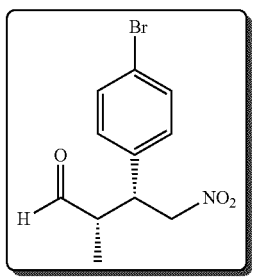

The title compound was prepared from propionaldehyde and (E)-1-bromo-4-(2-nitrovinyl)benzene according to the general procedure. Both enantiomeric excess and diastereomeric ratio were determined by HPLC with an AD-H column at 230 nm (2-propanol:hexane=5:95), 1.0 mL/min; major enantiomer $t_{major}$=18.59 min, $t_{minor}$=13.77 min. $[\alpha]_D^{20}$=−24.6 (c=2.1, CHCl$_3$).

$R_f$=0.18 (EA:Hexane=1:4);
$^1$H NMR (300 MHz, CDCl$_3$) δ 9.69 (d, J=1.5 Hz, 0.8H) (syn isomer), 9.52 (d, J=1.5 Hz, 0.2H) (anti isomer), 7.50-7.46 (m, 2H), 7.12-7.05 (m, 2H), 4.82-4.56 (m, 2H), 3.84-3.74 (m, 1H), 2.83-2.70 (m, 1H), 1.21 (d, J=7.3 Hz, 0.6H) (anti isomer), 1.00 (d, J=7.3 Hz, 2.4H) (syn isomer);
$^{13}$C NMR (75 MHz, CDCl$_3$) δ 201.8, 135.7, 132.3, 129.8, 122.1, 77.8, 48.2, 43.5, 12.2;
IR (thin film) v/cm$^{-1}$: 2976, 2935, 2879, 1726, 1553, 1489, 1377, 1010, 779, 717;
HRMS (ESI-TOF) Calcd. for C$_{11}$H$_{13}$NO$_3$Br: 286.0079 [M+H]$^+$. Found: 286.0081 [M+H]$^+$.

(2S,3R)-3-(4-Methoxyphenyl)-2-methyl-4-nitrobutanal

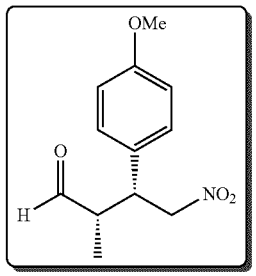

The title compound was prepared from propionaldehyde and (E)-1-methoxy-4-(2-nitrovinyl)benzene according to the general procedure. Both enantiomeric excess and diastereomeric ratio were determined by HPLC with an AS-H column at 230 nm (2-propanol:hexane=5:95), 1.0 mL/min; major enantiomer $t_{major}$=42.10 min, minor enantiomer $t_{minor}$=60.77 min. $[\alpha]_D^{20}$=−4.6 (c=1.3, CHCl$_3$).

$R_f$=0.13 (EA:Hexane=1:4);
$^1$H NMR (300 MHz, CDCl$_3$) δ 9.70 (d, J=1.4 Hz, 0.6H) (syn isomer), 9.53 (d, J=1.4 Hz, 0.4H) (anti isomer), (7.27-7.07 (m, 2H), 6.87-6.67 (m, 2H), 4.78-4.60 (m, 2H), 3.78 (s, 3H), 3.78-3.73 (m, 1H), 2.81-2.69 (m, 1H), 1.21 (d, J=7.2 Hz, 1.11H) (anti isomer), 0.99 (d, J=7.2 Hz, 1.89H) (syn isomer);
$^{13}$C NMR (75 MHz, CDCl$_3$) δ 202.5, 129.2, 129.1, 128.3, 114.4, 78.3, 55.2, 48.6, 43.3, 12.0;
IR (thin film) v/cm$^{-1}$: 2978, 2937, 2839, 1726, 1612, 1557, 1514, 1379, 1253, 1182, 1033, 833, 725;
HRMS (ESI-TOF) Calcd. for C$_{12}$H$_{16}$NO$_4$: 238.1079 [M+H]$^+$. Found: 238.1081 [M+H]$^+$.

(2S,3S)-3-(Furan-2-yl)-2-methyl-4-nitrobutanal

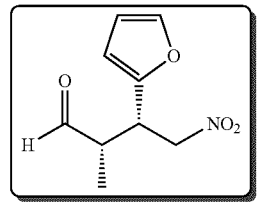

The title compound was prepared from propionaldehyde and (E)-2-(2-nitro-vinyl)furan according to the general procedure. Both enantiomeric excess and diastereomeric ratio were determined by HPLC with an AD-H column at 220 nm (2-propanol:hexane=0.8:99.2), 1.0 mL/min; major enantiomer $t_{major}$=30.44 min, minor enantiomer $t_{minor}$=26.29 min. $[\alpha]_D^{20}$=−20 (c=2.0, CHCl$_3$).

$R_f$=0.17 (EA:Hexane=1:4);
$^1$H NMR (400 MHz, CDCl$_3$) δ 9.70 (s, 0.87H) (syn isomer), 9.62 (s, 0.13H) (anti isomer), 7.35 (s, 1H), 6.30-6.29 (m, 1H), 6.17 (d, J=3.22 Hz, 1H), 4.77-4.67 (m, 2H), 4.13-4.05 (m, 1H), 2.87-2.76 (m, 1H), 1.22 (d, J=7.31 Hz, 0.48H) (anti isomer), 1.06 (d, J=7.31 Hz, 2.52H) (syn isomer);
$^{13}$C NMR (100 MHz, CDCl$_3$) δ 201.6, 149.9, 142.7, 110.4, 108.7, 75.8, 47.1, 37.6, 11.0;
IR (thin film) v/cm$^{-1}$: 3152, 3123, 2974, 2938, 2880, 1724, 1557, 1458, 1377, 1150, 1013, 814, 741, 702;
HRMS (ESI-TOF) Calcd. for C$_9$H$_{12}$NO$_4$: 198.0766 [M+H]$^+$. Found: 198.0761 [M+H]$^+$.

(2S,3R)-2-Ethyl-4-nitro-3-phenylbutanal

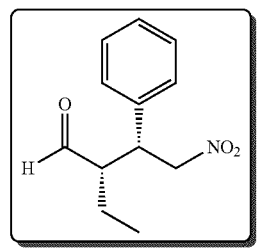

The title compound was prepared from butyraldehyde and (E)-(2-nitrovinyl)-benzene according to the general procedure. The enantiomeric ratio was determined by HPLC with an OD-H column at 220 nm (2-propanol:hexane=5:95), 1.0 mL/min; major enantiomer $t_{major}$=40.61 min, minor enantiomer $t_{minor}$=51.74 min. The diastereomeric excess was determined by $^1$H NMR. $[\alpha]_D^{20}$=−99.5 (c=1.1, CHCl$_3$).

$R_f$=0.27 (EA:Hexane=1:4);
$^1$H NMR (300 MHz, CDCl$_3$) δ 9.71 (d, J=2.5 Hz, 0.91H) (syn isomer), 9.47 (d, J=2.5 Hz, 0.09H) (anti isomer), 7.36-

HRMS (ESI-TOF): Calcd. for C$_{11}$H$_{14}$NO$_3$: 208.0974 [M+H]$^+$. Found: 208.0971 [M+H]$^+$.

7.27 (m, 3H), 7.20-7.17 (m, 2H), 4.80-4.59 (m, 2H), 3.84-3.75 (m, 1H), 2.72-2.64 (m, 1H), 1.55-1.43 (m, 2H), 1.21 (t, J=7.5 Hz, 0.33H) (syn isomer), 0.82 (t, J=7.5 Hz, 2.67H) (anti isomer);

$^{13}$C NMR (75 MHz, CDCl$_3$) δ 203.2, 136.8, 129.1, 128.0, 78.5, 42.6, 20.3, 10.6;

IR (thin film) v/cm$^{-1}$: 2967, 2936, 2878, 1720, 1553, 1456, 1379, 1244, 758, 702;

HRMS (ESI-TOF) Calcd. for C$_{12}$H$_{16}$NO$_3$: 222.1130 [M+H]$^+$. Found: 222.1129 [M+H]$^+$.

(2S,3R)-2-methyl-3-(naphthalen-1-yl)-4-nitrobutanal

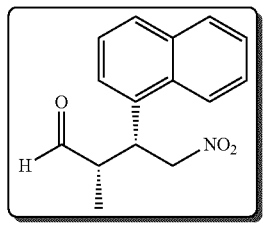

The title compound was prepared from butyraldehyde and (E)-1-(2-nitrovinyl)naphthalene according to the general procedure. Both enantiomeric excess and diastereomeric ratio were determined by HPLC with an AD-H column at 220 nm (2-propanol:hexane=0.8:99.2), 1.0 mL/min; major enantiomer $t_{major}$=43.3 min, minor enantiomer $t_{minor}$=37.6 min. $[α]_D^{20}$=−21.1 (c=2.4, CHCl$_3$).

R$_f$=0.33 (EA:Hexane=1:4);

$^1$H NMR (100 MHz, CDCl$_3$) δ 9.75 (d, J=1.6 Hz, 0.85H) (syn isomer), 9.62 (d, J=1.6 Hz, 0.15H) (anti isomer), 8.14-8.10 (m, 1H), 7.88 (d, J=8.0 Hz, 1H), 7.80 (d, J=8.2 Hz, 1H), 7.61-7.41 (m, 3H), 7.35 (d, J=7.1 Hz, 1H), 4.94-4.76 (m, 3H), 3.01-2.96 (m, 1H), 1.21 (d, J=7.3 Hz, 0.45H) (anti isomer), 0.97 (d, J=7.3 Hz, 2.55H) (syn isomer);

$^{13}$C NMR (100 MHz, CDCl$_3$) δ 202.5, 134.1, 133.3, 131.9, 129.2, 128.6, 126.9, 126.0, 125.3, 123.9, 122.4, 77.9, 49.2, 37.4, 12.5;

IR (thin film) v/cm$^{-1}$: 3049, 2978, 2936, 1730, 1715, 1552, 1377, 1246, 799, 779;

HRMS (ESI-TOF) Calcd. for C$_{15}$H$_{16}$NO$_3$: 258.1130. [M+H]$^+$. Found: 258.1138 [M+H]$^+$.

(2S,3R)-2-isopropyl-4-nitro-3-phenylbutanal

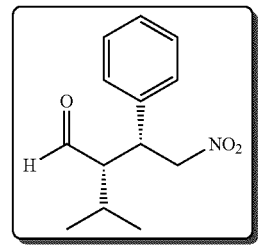

The title compound was prepared from isovaleraldehyde and (E)-(2-nitrovinyl)benzene according to the general procedure. The enantiomeric excess was determined by HPLC with an AD-H column at 210 nm (2-propanol:hexane=1:99), 1.0 mL/min; major enantiomer $t_{major}$=21.8 min, minor enantiomer $t_{minor}$=17.9 min, the diastereomeric ratio was determined by $^1$H NMR. $[α]_D^{20}$=−6.5 (c=2.3, CHCl$_3$).

R$_f$=0.38 (EA:Hexane=1:4);

$^1$H NMR (300 MHz, CDCl$_3$) δ=9.90 (d, J=2.4 Hz, 0.95H) (syn isomer), 9.48 (d, J=2.4 Hz, 0.05H) (anti isomer), 7.36-7.28 (m, 3H), 7.27-7.18 (m, 2H), 4.70-4.53 (m, 2H), 3.94-3.86 (m, 1H), 2.80-2.74 (m, 1H), 1.73-1.66 (m, 1H), 1.08 (d, J=6.9 Hz, 2.1H) (syn isomer), 1.01 (d, J=6.9 Hz, 0.9H) (anti isomer), 0.92 (d, J=6.9 Hz, 0.9H) (anti isomer), 0.87 (d, J=6.9 Hz, 2.1H) (syn isomer);

$^{13}$C NMR (75 MHz, CDCl$_3$) δ 204.3, 137.0, 129.0, 128.3, 127.9, 78.9, 58.6, 41.8, 27.8, 21.5, 16.8;

IR (neat) v/cm$^{-1}$ 12970, 2833, 2722, 1724, 1557, 1379, 1093, 816, 750, 706, 648;

HRMS (ESI-TOF) Calcd. for C$_{13}$H$_{18}$NO$_3$: 236.1287 [M+H]$^+$. Found: 236.1286 [M+H]$^+$.

(S)-2,2-dimethyl-4-nitro-3-phenylbutanal

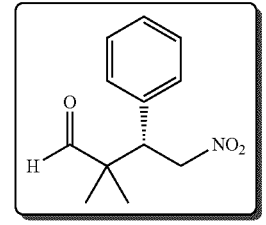

The title compound was prepared from (E)-(2-nitrovinyl)benzene and isobutyraldehyde according to the general procedure. The enantiomeric ratio were determined by HPLC with Chiralpak OD-H column at 210 nm (2-propanol:hexane=15:85), 1 mL/min, $t_{major}$=19.7 min, $t_{minor}$=13.9 min, $[α]_D^{20}$=−4.3 (c=1.6, CHCl$_3$).

R$_f$=0.14 (EA:Hexane=1:10);

$^1$H NMR (300 MHz, CDCl$_3$) δ: 9.53 (s, 1H), 7.36-7.26 (m, 3H), 7.21-7.18 (m, 2H), 4.85 (dd, J=12.9 Hz, 11.2 Hz, 1H), 4.68 (dd, J=12.9 Hz, 4.2 Hz, 1H), 3.78 (dd, J=11.2 Hz, 4.2 Hz, 1H), 1.14 (s, 3H), 1.01 (s, 3H);

$^{13}$C NMR (75 MHz, CDCl$_3$) δ: 204.2, 135.4, 129.1, 128.7, 128.2, 76.6, 48.5, 48.2, 21.7, 18.9;

IR (thin film) v/cm$^{-1}$: 2922, 1728, 1556, 1454, 1379, 704;

HRMS (ESI-TOF) Calcd. for C$_{12}$H$_{16}$NO$_3$: 222.1130 [M+H]$^+$. Found: 222.1123 [M+H]$^+$.

(S)-3-(4-bromophenyl)-2,2-dimethyl-4-nitrobutanal

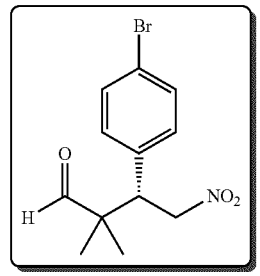

The title compound was prepared from trans-1-bromo-4-(2-nitrovinyl)benzene and isobutyraldehyde according to general procedure. The enantiomeric excess was determined by HPLC with Chiralpak AD-H column at 210 nm (2-propanol:hexane=10:90), 1 mL/min; $t_{major}$=11.5 min, $t_{minor}$=9.3 min, $[\alpha]_D^{20}$=−2.4 (c=2.9, CHCl$_3$);

$R_f$=0.24 (EA:Hexane=1:4);

$^1$H NMR (400 MHz, CDCl$_3$) δ 9.49 (s, 1H), 7.46 (d, J=8.2 Hz, 2H), 7.08 (d, J=8.2 Hz, 2H), 4.80 (t, J=12.9, 1H), 4.67 (dd, J=13.2, 4.2 Hz, 1H), 3.75 (dd, J=11.4, 4.0 Hz, 1H), 1.12 (s, 3H), 1.00 (s, 3H);

$^{13}$C NMR (100 MHz, CDCl$_3$) δ 203.8, 134.5, 131.9, 130.7, 122.2, 76.0, 48.1, 47.9, 21.7, 18.9;

IR (thin film) v/cm$^{-1}$: 2922, 2725, 1722, 1560, 1543, 1009, 880, 849, 721;

HRMS (ESI-TOF) Calcd. for C$_{12}$H$_{15}$NO$_3$Br: 300.0235 [M+H]$^+$. Found: 300.0212 [M+H]$^+$.

(S)-3-(furan-3-yl)-2,2-dimethyl-4-nitrobutanal

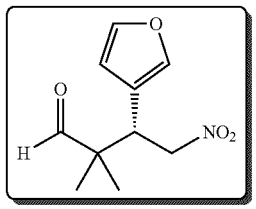

The title compound was prepared from trans-2-(2-nitrovinyl) furan, and isobutyraldehyde according to general procedure. The enantiomeric excess was determined by HPLC with Chiralpak OD-H column at 210 nm (2-propanol:hexane=20:80), 1 mL/min, $t_{major}$=12.5 min, $t_{minor}$=8.3 min, $[\alpha]_D^{20}$=+1.5 (c=2.8, CHCl$_3$);

$R_f$=0.33 (EA:Hexane=1:4);

$^1$H NMR (400 MHz, CDCl$_3$) δ 9.52 (s, 1H), 7.37 (s, 1H), 6.31 (dd, J=1.9, 1.2 Hz, 1H), 6.21 (d, J=3.2 Hz, 1H), 4.75 (dd, J=12.9, 11.0 Hz, 1H), 4.58 (dd, J=12.9, 3.9 Hz, 1H), 3.92 (dd, J=11.0 Hz, 3.9 Hz, 1H), 1.17 (s, 3H), 1.04 (s, 3H);

$^{13}$C NMR (100 MHz, CDCl$_3$) δ 203.5, 149.8, 142.8, 110.4, 109.7, 74.9, 48.2, 42.3, 21.2, 19.1,

IR (thin film) v/cm$^{-1}$: 2972, 1726, 1557, 1470, 1433, 1377, 1148, 885, 818, 741;

HRMS (ESI-TOF) Calcd. for C$_{10}$H$_{14}$NO$_4$: 212.0923 [M+H]$^+$. Found: 212.0926 [M+H]$^+$.

(S)-3-(4-Methoxyphenyl)-2,2-dimethyl-4-nitrobutanal

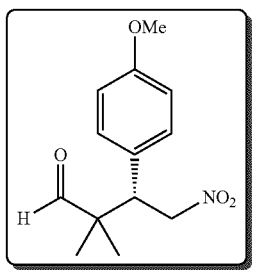

The title compound was prepared from trans-1-methoxy-4-(2-nitrovinyl) benzene and isobutyraldehyde according to general method. The enantiomeric excess was determined by HPLC with Chiralpak AS-H column at 210 nm (2-propanol:hexane=20:80), 1 ml/min; $t_{major}$=12.7 min, $t_{minor}$=15.8 min, $[\alpha]_D^{20}$=+9.1 (c=1.2, CHCl$_3$);

$R_f$=0.24 (EA:Hexane=1:4);

$^1$H NMR (400 MHz, CDCl$_3$) δ 9.52 (s, 1H), 7.11 (d, J=8.6 Hz, 2H), 6.85 (d, J=8.7 Hz, 2H), 4.80 (dd, J=12.8, 11.6 Hz, 1H), 4.66 (dd, J=12.8, 4.2 Hz, 1H), 3.78 (s, 3H), 3.72 (dd, J=11.4, 4.2 Hz, 1H), 1.12 (s, 3H), 1.00 (s, 3H), $^{13}$C NMR (100 MHz, CDCl$_3$) δ 204.5, 159.3, 130.1, 127.1, 114.1, 76.5, 55.2, 48.4, 47.9, 21.6, 18.9;

IR (thin film) v/cm$^{-1}$: 2922, 1719, 1609, 1549, 1514, 1462, 1377, 1250, 1028, 839, 723;

HRMS (ESI-TOF) Calcd. for C$_{13}$H$_{18}$NO$_4$: 252.1236 [M+H]$^+$. Found: 252.1239.

(S)-2,2-Dimethyl-3-(naphthalen-2-yl)-4-nitrobutanal

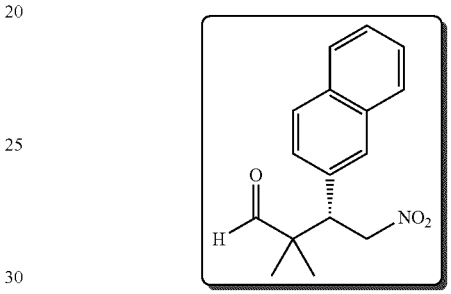

The title compound was prepared from (E)-2-(2-nitrovinyl)naphthalene and isobutyraldehyde according to General Procedure. The enantiomeric excess was determined by HPLC with Chiralpak AS-H column at 210 nm (2-propanol:hexane=10:90), 1 mL/min, $t_{major}$=16.2 min, $t_{minor}$=18.0 min, $[\alpha]_D^{20}$=+1.7 (c=1.8, CHCl$_3$)

$R_f$=0.27 (EA:Hexane=1:4);

$^1$H NMR (400 MHz, CDCl$_3$) δ 9.57 (s, 1H), 7.83-7.80 (m, 3H), 7.67 (brs, 1H), 7.50 (t, J=4.0 Hz, 2H), 7.32 (dd, J=8.5, 1.5 Hz, 1H), 4.99 (dd, J=13.0 Hz, 11.7 Hz, 1H), 4.78 (dd, J=13.2, 4.1 Hz, 1H), 3.96 (dd, J=11.3, 4.1 Hz, 1H), 1.19 (s, 3H), 1.05 (s, 3H);

$^{13}$C NMR (100 MHz, CDCl$_3$) δ 204.3, 133.1, 132.9, 128.5, 128.4, 127.9, 127.8, 127.6, 126.6, 126.5, 126.4, 76.4, 48.6, 48.4, 21.8, 19.1;

IR (neat): 2725, 2670, 1722, 1555, 1306, 1159, 754, 721 cm$^{-1}$;

HRMS (ESI-TOF) Calcd. for C$_{16}$H$_{18}$NO$_3$: 272.1287 [M+H]$^+$. Found: 272.1273.

(2S,3S)-2-methyl-3-(nitromethyl)-5-phenylpentanal

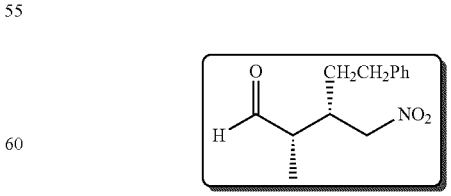

The title compound was prepared from (E)-(4-nitrobut-3-enyl)benzene and propionaldehyde according to general procedure. The enantiomeric excess was determined by HPLC with Chiralpak AD-H column at 210 nm (2-propanol:hexane=2:98), 1 mL/min, $t_{major}$=15.4 min, $t_{minor}$=14.4 min, the diastereomeric ratio was determined by ¹H NMR. $[\alpha]_D^{20}$=−2.2 (c=2.7, CHCl₃);
$R_f$=0.31 (EA:Hexane=1:4);
¹H NMR (400 MHz, CDCl₃): δ9.64 (d, J=13.9 Hz, 0.43H) (anti isomer), 9.61 (d, J=13.9 Hz, 0.57H) (syn isomer), 7.32-7.14 (m, 5H), 4.56-4.51 (m, 1H), 4.79-4.42 (m, 1H), 2.81-2.57 (m, 4H), 1.87 (m, 2H), 1.17 (d, J=17.2 Hz, 1.71H) (syn isomer), 0.95 (d, J=17.2 Hz, 1.29H) (anti isomer);
¹³C NMR (100 MHz, CDCl₃): δ 202.7, 140.5, 128.7, 128.2, 126.4, 47.0, 36.8, 33.2, 30.3, 9.1;
IR (thin film) v/cm⁻¹: 3026, 2968, 2880, 1724, 1553, 1454, 700;
HRMS (ESI-TOF) Calcd. for $C_{13}H_{18}NO_3$: 236.1287 [M+H]⁺. Found: 236.1287 [M+H]⁺.

(2S,3S)-3-cyclohexyl-2-methyl-4-nitrobutanal

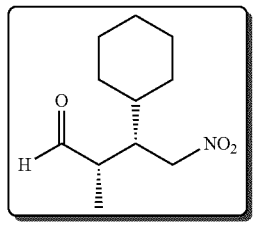

The title compound was prepared from (E)-(2-nitrovinyl)cyclohexane and propionaldehyde according to general procedure. The enantiomeric excess was determined by HPLC with Chiralpak AD-H column at 210 nm (2-propanol:hexane=1:99), 1 mL/min, $t_{major}$=17.0 min, $t_{minor}$=19.1 min, the diastereomeric ratio was determined by ¹H NMR. $[\alpha]_D^{20}$=−17.2 (c=1.1, CHCl₃),
$R_f$ 0.40 (EA:Hexane=1:4);
¹H NMR (500 MHz, CDCl₃): δ 9.68 (s, 1H) (anti isomer+ syn isomer), 4.59 (dd, J=5.3, 13.4 Hz, 1H), 4.38 (dd, J=6.8, 13.4 Hz, 1H), 2.61-2.54 (m, 2H), 1.81-1.56 (m, 5H), 1.50-1.41 (m, 1H), 1.27-0.90 (m, 5H), 1.11 (d, J=7.0 Hz, 1.2H) (anti isomer), 1.20 (d, J=7.0 Hz, 1.8H) (syn isomer);
¹³C NMR (125 MHz, CDCl₃): δ203.0, 75.2, 46.2, 43.5, 38.0, 31.6, 29.9, 26.3, 26.3, 26.1, 9.9;
IR (neat): v/cm⁻¹: 2971, 2930, 2855, 1717, 1557, 1380, 1161, 1128, 950, 816, 735.
HRMS (ESI-TOF): Calcd. for $C_{11}H_{20}NO_3$: 214.1443 [M+H]⁺. Found: 214.1446 [M+H]⁺.

(2S,3R)-2-isopropyl-3-(naphthalen-1-yl)-4-nitrobutanal

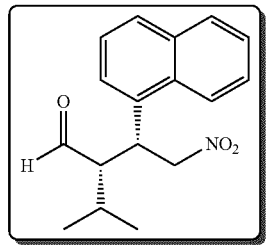

The title compound was prepared from (E)-1-(2-nitrovinyl)naphthalene and isovaleraldehyde according to general procedure. The enantiomeric excess was determined by HPLC with Chiralpak AD-H column at 254 nm (2-propanol:hexane=10:90), 1 mL/min, $t_{major}$=13.7 min, $t_{minor}$ 16.8 min, the diastereomeric ratio was determined by ¹H NMR. $[\alpha]_D^{20}$=−178 (c=0.23, CHCl₃);
$R_f$=0.27 (EA:Hexane=1:4);
¹H NMR (300 MHz, CDCl₃): δ10.0 (d, J=2.4 Hz, 0.96H) (syn isomer), 9.76 (d, J=2.4 Hz, 0.04H) (anti isomer), 8.18 (brs, 1H), 7.85 (dd, J=24.0 Hz, 7.5 Hz, 2H), 7.64-7.40 (m, 3H), 7.34 (d, J=7.5 Hz, 1H), 4.89-4.79 (m, 2H), 3.09 (brs, 1H), 1.79 (s, 1H), 1.14 (d, J=6.9 Hz, 3H), 0.84 (d, J=6.9 Hz, 3H);
¹³C NMR (75 MHz, CDCl₃): δ 204.8, 134.3, 133.4, 131.7, 129.4, 128.6, 126.9, 126.1, 125.4, 124.1, 122.3;
IR (neat) v/cm⁻¹ 3048, 2963, 2739, 1715, 1557, 1512, 1464, 799, 779, 758;
HRMS (ESI-TOF) Calcd. for $C_{17}H_{20}NO_3$: 286.1443 [M+H]⁺. Found: 286.1441 [M+H]⁺.

(2S,3R)-3-(4-bromophenyl)-2-isopropyl-4-nitrobutanal

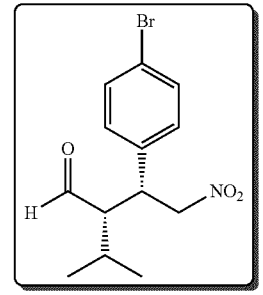

The title compound was prepared from (E)-1-bromo-4-(2-nitrovinyl)benzene and isovaleraldehyde according to general procedure. The enantiomeric excess was determined by HPLC with Chiralpak AD-H column at 254 nm (2-propanol:hexane=10:90), 1 mL/min, $t_{major}$=7.6 min, $t_{minor}$=7.2 min, the diastereomeric ratio was determined by ¹H NMR. $[\alpha]_D^{20}$=−30.2 (c=0.27, CHCl₃);

$R_f$=0.50 (EA:Hexane=1:4);
¹H NMR (400 MHz, CDCl₃) δ9.91 (d, J=2.0 Hz, 0.98H) (syn isomer), 9.50 (d, J=2.0 Hz, 0.02H) (anti isomer), 7.48 (d, J=8.4 Hz, 2H), 7.07 (d, J=8.4 Hz, 2H) 4.67 (dd, J=12.7 Hz, 4.3 Hz, 1H), 4.54 (dd, J=12.7 Hz, 4.3 Hz, 1H), 3.88 (dt, J=10.5 Hz, 4.3 Hz, 1H), 2.75 (ddd, J=6.0 Hz, 3.8 Hz, 2.1 Hz, 1H), 1.73-1.68 (m, 1H), 1.12 (d, J=7.2 Hz, 3H), 0.86 (d, J=7.2 Hz, 3H);
¹³C NMR (100 MHz, CHCl₃) δ 203.9, 136.2, 132.4, 129.6, 122.1, 78.7, 58.5, 41.4, 28.0, 21.6, 17.0;
IR (neat): v=2725, 1712, 1566, 1338, 1261, 821, 719 cm⁻¹;
HRMS (ESI-TOF) Calcd. for $C_{13}H_{17}NO_3Br$: 314.0392 [M+H]⁺. Found: 314.0384 [M+H]⁺.

Characterization of Chiral Alcohol Obtained Using a Reduction Process According to the Invention

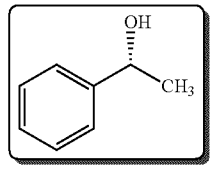

(R)-1-Phenylethanol (Coroley, E J, & Link, J O, *Tetrahedron Lett.* (1992) 33, 4141)

(FIG. 11, entry 1): colorless oil, 98% yield, 81% ee, $[\alpha]_D^{25}=-14.9$ (c=1.0, $CH_2Cl_2$);

$R_f$=0.41 (EA/Hexane=1/5);

$^1$H NMR (400 MHz, $CDCl_3$): δ 7.28-7.17 (m, 5H), 4.72 (q, J=6.5 Hz, 1H), 3.23 (br, 1H), 1.37 (d, J=6.5 Hz, 3H);

$^{13}$C NMR (100 MHz, $CDCl_3$): δ 145.7, 128.2, 127.1, 125.3, 70.0, 24.9;

The enantiomeric excess was determined by chiral HPLC analysis, employing a Dacicel Chiralcel OD column (Hexane:i-propanol 95:1 mL/min): $t_1$=8.66 min (major), $t_2$=10.33 min (minor).

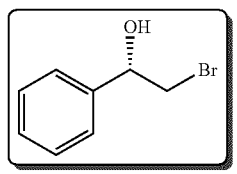

(S)-2-Bromo-1-phenylethanol (Basavaiah, D, et al., *Tetrahedron: Asymmetry* (2002) 13, 1125-1128)

(FIG. 11, entry 2): colorless oil, 98% yield, 92% ee, $[\alpha]_D^{25}=+55.3$ (c=0.5, $CH_2Cl_2$);

$R_f$=0.50 (EA/Hexane=1/4);

$^1$H NMR (300 MHz, $CDCl_3$): δ 7.38-7.32 (m, 5H), 4.92 (d, J=8.6 Hz, 1H), 3.65-3.51 (m, 2H), 2.70 (br, 1H);

$^{13}$C NMR (100 MHz, $CDCl_3$): δ 140.3, 128.7, 128.4, 125.9, 73.8, 40.2;

The enantiomeric excess was determined by chiral HPLC analysis, employing a Dacicel Chiralcel OD column (Hexane:i-propanol 95:5, 0.5 mL/min): $t_1$=23.30 min (major), $t_2$=27.13 min (minor). FIG. 21 (A, B & C) depicts the data of HPLC analysis.

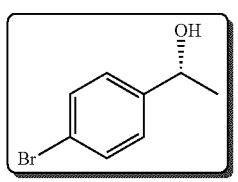

(R)-1-(4-Bromophenyl)-ethanol (Du, D-M., et al.; *Org. Lett.* (2006) 8, 1327-1330)

(not depicted in FIG. 11): colorless oil, 98% yield, 76% ee, $[\alpha]_D^{25}=+18.0$ (c=3.0, $CH_2Cl_2$);

$R_f$=0.33 (EA/Hexane=1/4);

$^1$H NMR (400 MHz, $CDCl_3$): δ7.47 (d, J=8.3 Hz, 2H), 7.25 (d, J=7.6 Hz, 2H), 4.87 (q, J=3.7 Hz, 1H), 1.47 (d, J=6.4 Hz, 3H);

$^{13}$C NMR (100 MHz, $CDCl_3$): δ 144.8, 131.6, 127.1, 121.2, 69.8, 25.2;

The enantiomeric excess determined by chiral HPLC analysis, employing chiral HPLC analysis, employing a Dacicel Chiralcel OB-H column (Hexane:i-propanol 95:5, 0.5 mL/min): $t_1$=7.57 min (minor), $t_2$=8.38 min (major). FIG. 22 (A-D) depicts the data of HPLC analysis.

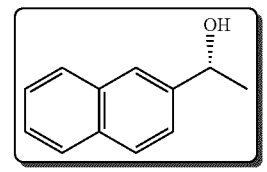

(R)-1-(2-Naphthyl)-ethanol (Josyula V, et al., *Tetrahedron* (2002) 58, 1069-1074)

(FIG. 11, entry 3): colorless oil, 99% yield, 89% ee, $[\alpha]_D^{25}=+21.9$ (c=2.2, $CH_2Cl_2$);

$R_f$=0.38 (EA/Hexane=1/4);

$^1$H NMR (400 MHz, $CDCl_3$): δ7.77-7.71 (m, 4H), 7.44-7.41 (m, 3H), 4.95 (q, J=6.4 Hz, 1H), 2.42 (brs, 1H), 1.50 (d, J=6.5 Hz, 3H);

$^{13}$C NMR (100 MHz, $CDCl_3$): δ 143.1, 133.1, 132.7, 128.0, 127.8, 127.5, 125.9, 125.5, 123.7, 123.6, 70.1, 24.9;

The enantiomeric excess was determined by chiral HPLC analysis, employing a Dacicel Chiralcel AS-H column (Hexane:i-propanol 97:3, 1 mL/min), retention times (min): $t_1$=14.04 min (major), $t_2$=16.47 min (minor). FIG. 23 (A-D) depicts the data of HPLC analysis.

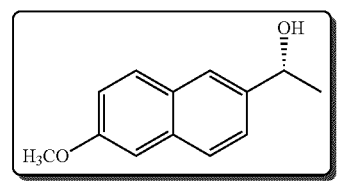

(R)-1-(2-(6-methoxy)-Naphthyl)-ethanol (Bouzemi, N, et al., *Tetrahedron: Asymmetry* (2006) 17, 797-800)

(not depicted in FIG. 11): colorless solid, 98% yield, 70% ee, $[\alpha]_D^{25}=+26.7$ (c=1.6, $CH_2Cl_2$);

$R_f$=0.32 (EA/hexane=1/4);

$^1$H NMR (300 MHz, $CDCl_3$): δ7.68-7.65 (m, 3H), 7.42 (d, J=6.3 Hz, 1H), 7.13-7.08 (m, 2H), 4.93 (q, J=4.4 Hz, 1H), 3.87 (s, 3H), 2.34 (br, 1H), 1.51 (d, J=4.8 Hz, 3H);

$^{13}$C NMR (75 MHz, $CDCl_3$): δ 157.5, 140.9, 133.9, 129.3, 128.6, 127.0, 124.3, 123.7, 118.8, 105.6, 70.3, 55.2, 25.0;

The enantiomeric excess determined by chiral HPLC analysis, employing a Dacicel Chiralcel OD column (Hexane:i-propanol 95:5, 1 mL/min): $t_1$=15.76 min (minor), $t_2$=22.53 min (major). FIG. 24 (A-D) depicts the data of HPLC analysis.

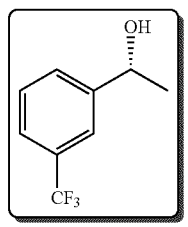

(R)-1-(3-Trifluoromethylphenyl)-ethanol (Xu, Y, et al., *J. Org. Chem.* (2005) 70, 8079-8087)

(FIG. 11, entry 4): colorless oil, 98% yield. 86% ee, $[\alpha]_D^{25}$=+22.7 (c=3.1, CH$_2$Cl$_2$);

$R_f$=0.28 (EA:hexane=1:4);

$^1$H NMR (400 MHz, CDCl$_3$): δ7.61 (s, 1H), 7.50 (s, 2H), 7.43 (q, J=7.4 Hz, 1H), 4.88 (br, 1H), 2.84 (br, 1H), 1.44 (d, J=6.3 Hz, 3H);

$^{13}$C NMR (100 MHz, CDCl$_3$): δ 146.7, 130.7 (q, J=31.9 Hz), 128.9, 128.7, 125.5, 124.1 (q, J=3.7 Hz), 122.1 (q, J=3.7 Hz), 69.7, 25.2.

The enantiomeric excess determined by HPLC analysis (Daicel Chiralcel OBH column, hexane: 2-propanol=99:1 1.0 mL/min). Retention time: $t_{minor}$=5.47 and $t_{major}$=7.79 min. FIG. 29 (A, B) and FIG. 30 (A, B) depict the data of HPLC analysis.

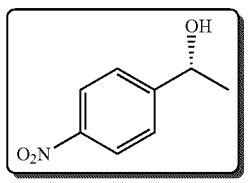

(R)-1-(4-Nitrophenyl)-ethanol (Du, D-M., et al., *Org. Lett.* (2006) 8, 1327-1330)

(FIG. 11, entry 6): colorless oil, 96% yield. 92% ee, $[\alpha]_D^{25}$=+26.7 (c=1.6, CH$_2$Cl$_2$);

$R_f$=0.33 (EA/hexane=1/4);

$^1$H NMR (300 MHz, CDCl$_3$): δ8.17 (d, J=8.7 Hz, 2H), 7.53 (d, J=8.7 Hz, 2H), 5.01 (q, J=6.5 Hz, 1H), 1.51 (d, J=6.5 Hz, 3H);

$^{13}$C NMR (75 MHz, CDCl$_3$): δ 153.2, 147.2, 126.1, 23.6, 69.4, 25.4;

The enantiomeric excess determined by HPLC analysis (Daicel Chiralcel OB-H column, hexane: 2-propanol=95:5, 1 mL/min). Retention time: $t_{minor}$=20.71 and $t_{major}$=21.48 min. FIG. 25 (A, B) and FIG. 26 (A, B) depict the data of HPLC analysis.

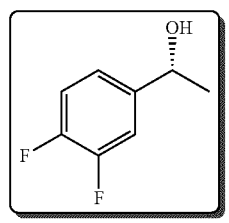

(R)-1-(3,4-difluorophenyl)ethanol (Burk, M. J, et al., *Org. Lett.* (2000) 2, 4173-4176; Dale, J A., et al. *J. Org. Chem.* (1969) 34, 2543-2549)

(FIG. 11, entry 7): colorless solid, 99% yield. 95% ee, $[\alpha]_D^{25}$=+27.4 (c=2.0, CH$_2$Cl$_2$);

$R_f$=0.26 (EA:hexane=1:4);

$^1$H NMR (300 MHz, CDCl$_3$): δ7.20-7.01 (m, 3H), 4.83-4.80 (m, J=6.5 Hz, 1H), 2.53 (s, 1H), 1.43 (d, J=6.5 Hz, 3H);

$^{13}$C NMR (75 MHz, CDCl$_3$): δ 151.5 (dd, J=12.4, 62.6 Hz), 148.2 (dd, J=12.4, 62.6 Hz), 142.8 (dd, J=4.9, 1.0 Hz), 121.2 (q, J=3.9 Hz), 117.0 (d, J=17.0 Hz), 114.3 (d, J=17.0 Hz), 69.2, 25.2;

The enantiomeric excess determined by HPLC analysis (Daicel Chiralcel OB-H column, hexane: 2-propanol=97:3 1.0 mL/min). Retention time: $t_{minor}$=7.73 and $t_{major}$=8.50 min. FIG. 34 (A-D) depicts the data of HPLC analysis.

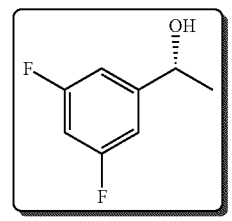

(R)-1-(3,5-difluorophenyl)ethanol (Josyula V., et al., *Tetrahedron* (2002) 58, 1069-1074)

(FIG. 11, entry 8): colorless oil, 99% yield. 93% ee, $[\alpha]_D^{25}$=+34.8 (c=1.3, CH$_2$Cl$_2$);

$R_f$=0.39 (EA:hexane=1:4);

$^1$H NMR (400 MHz, CDCl$_3$): δ 6.93-6.86 (m, 2H), 6.67-6.66 (m, 1H), 4.92-4.84 (m, 1H), 1.90 (d, J=3.6 Hz, 1H), 1.48 (d, J=6.5 Hz, 3H); $^{13}$C NMR (100 MHz, CDCl$_3$): δ 164.8 (d, J=12.7 Hz), 161.5 (d, J=12.7 Hz), 150.0 (t, J=8.3 Hz), 108.1 (d, J=25.5 Hz), 108.2 (d, J=8.9 Hz), 102.6 (d, J=25.5 Hz), 69.5, 25.2;

The enantiomeric excess determined by HPLC analysis (Daicel Chiralcel OB-H column, hexane: 2-propanol=97:3, 1.0 mL/min). Retention time: $t_{minor}$=6.50 and $t_{major}$=9.37 min. FIG. 32 (A-D) depicts the data of HPLC analysis.

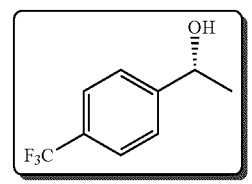

(R)-1-(4-Trifluoromethylphenyl)-ethanol (Mathre D J., et al., *J. Org. Chem.* (1993) 58, 2880-2888)

(FIG. 11, entry 9): colorless oil, 99% yield. 97% ee, $[\alpha]_D^{25}$=+38.6 (c=1.0, CH$_2$Cl$_2$);

$R_f$=0.39 (EA/hexane=1/4);

$^1$H NMR (300 MHz, CDCl$_3$): δ7.53 (d, J=8.1 Hz, 2H), 7.36 (d, J=8.2 Hz, 2H), 4.84-4.76 (m, 1H), 4.00 (d, J=3.6 Hz, 1H), 1.39 (d, J=6.5 Hz, 3H);

$^{13}$C NMR (75 MHz, CDCl$_3$): δ 149.1, 129.4 (q, J=32.0 Hz), 125.6, 125.2 (q, J=3.8 Hz), 122.4, 69.5, 25.0;

The enantiomeric excess determined by HPLC analysis (Daicel Chiralcel OJ column, hexane: 2-propanol=99.8:0.2, 1.0 mL/min). Retention time: $t_{major}$=36.92 and $t_{minor}$=47.81 min. FIG. 28 (A-D) depicts the data of HPLC analysis.

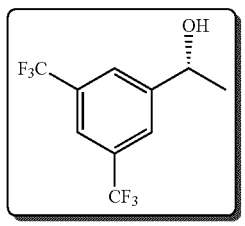

(R)-3,5-bistrifluoromethylphenyl ethanol (Pollard, D, et al., *Tetrahedron: Asymmetry* (2006) 17, 554-559)

(FIG. 11, entry 10): colorless solid, 99% yield. 93% ee, $[\alpha]_D^{25}$=+15.0 (c=1.4, $CH_2Cl_2$);

$R_f$=0.48 (EA:hexane=1:4);

$^1$H NMR (400 MHz, $CDCl_3$): δ 7.84-7.77 (m, 3H), 5.02-5.00 (m, 1H), 4.92-4.84 (m, 1H), 2.70 (d, J=3.6 Hz, 1H), 1.52 (d, J=6.5 Hz, 3H);

$^{13}$C NMR (100 MHz, $CDCl_3$): δ 148.2, 131.7 (q, J=33.0 Hz), 150.0 (t, J=8.3 Hz), 125.6 (d, J=2.5 Hz), 124.7, 122.0, 69.3, 25.4;

The enantiomeric excess determined by HPLC analysis (Daicel Chiralcel OB-H column, hexane: 2-propanol=99.5:0.5, 1.0 mL/min). Retention time: $t_{minor}$=9.57 and $t_{major}$=10.34 min. FIG. 33 (A-D) depicts the data of HPLC analysis.

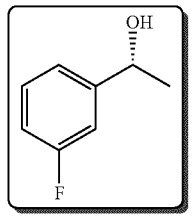

(R)-1-(3-fluorophenyl)-ethanol (Liu, P N., et al., *Chem. Commun.* (2004) 2070-2071)

(FIG. 11, entry 11): colorless oil, 99% yield. 90% ee, $[\alpha]_D^{25}$=+17.8 (c=0.9, $CH_2Cl_2$);

$R_f$=0.45 (EA/hexane=1/4);

$^1$H NMR (300 MHz, $CDCl_3$): δ 7.27-7.20 (m, 1H), 7.05-7.00 (m, 2H), 6.93-6.87 (m, 1H), 4.76 (q, J=6.5 Hz, 3H), 3.4 (br, 1H), 1.38 (d, J=6.5 Hz, 3H)

$^{13}$C NMR (75 MHz, $CDCl_3$): δ 164.4, 161.2, 148.5 (d, J=6.6 Hz), 129.8 (d, J=8.3 Hz), 120.9 (d, J=2.8 Hz), 113.9 (d, J=22.1 Hz), 112.2 (d, J=22.1 Hz), 69.4, 25.0.

The enantiomeric excess determined by HPLC analysis (Daicel Chiralcel OB-H column, hexane: 2-propanol=99:1, 1 mL/min). Retention time: $t_{minor}$=17.58 and $t_{major}$=27.14 min.

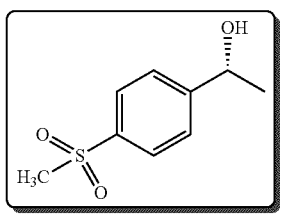

(R)-1-(4-methylsulfonylphenyl)ethanol (Tagat, J R, et al., *J. Med. Chem.* (2001) 44, 3343-3346)

(not depicted in FIG. 11): colorless solid, 99% yield. 97% ee, $[\alpha]_D^{25}$=+17.6 (c=0.6, $CH_2Cl_2$);

$R_f$=0.04 (EA:hexane=1:4);

$^1$H NMR (400 MHz, $CDCl_3$): δ7.84 (d, J=8.3 Hz, 2H), 7.55 (d, J=8.3 Hz, 2H), 4.98 (q, J=6.5 Hz, 1H), 3.03 (s, 3H), 1.49 (d, J=6.5 Hz, 3H);

$^{13}$C NMR (100 MHz, $CDCl_3$): δ 152.4, 138.8, 127.3, 126.2, 69.2, 44.4, 25.3;

The enantiomeric excess determined by HPLC analysis (Daicel Chiralcel OBH column, hexane: 2-propanol=99:1 1.0 mL/min). Retention time: $t_{minor}$=60.93 and $t_{major}$=63.01 min. FIG. 31 (A-D) depicts the data of HPLC analysis.

X-ray crystal data of 6a and 7a

Crystal Structure of 6a

Figure 17:
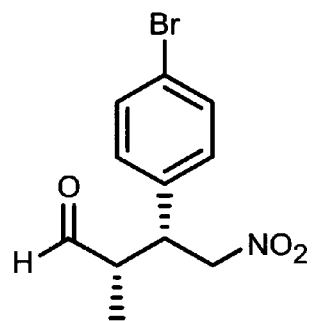
FIG. 17 shows graphically the results of X-Ray crystal data analysis of a compound of the invention of general Formula (VI) (cf. also FIG. 4A and the Examples below).
Figure 17:
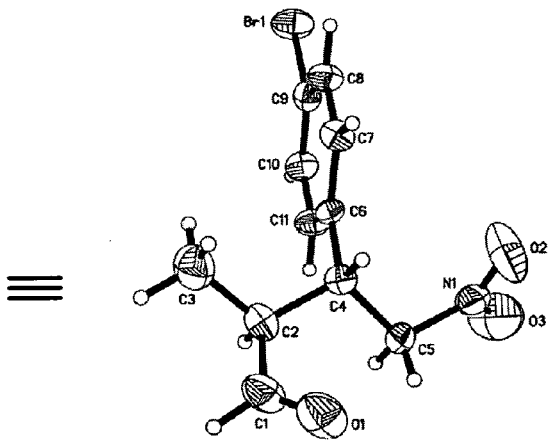
Figure 17:
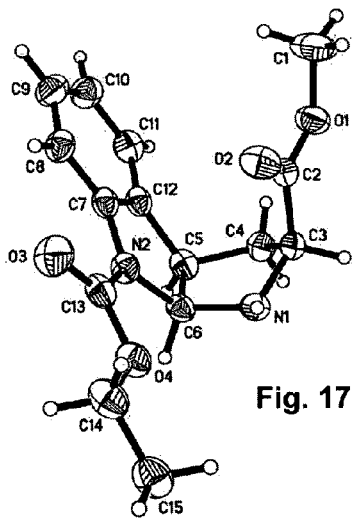

The structure is graphically represented in FIG. 17.

| | |
|---|---|
| chemical_formula_moiety | C15 H18 N2 O4 |
| chemical_formula_sum | C15 H18 N2 O4 |
| chemical_formula_weight | 290.31 |
| symmetry_cell_setting | Orthorhombic |
| symmetry_space_group_name_H-M | P2(1)2(1)2(1) |
| cell_length_a | 7.9402(2) |
| cell_length_b | 11.7992(3) |
| cell_length_c | 15.7954(4) |
| cell_angle_alpha | 90.00 |
| cell_angle_beta | 90.00 |
| cell_angle_gamma | 90.00 |
| cell_volume | 1479.84(6) |
| cell_formula_units_Z | 4 |
| cell_measurement_temperature | 296(2) |
| cell_measurement_reflns_used | 8324 |
| cell_measurement_theta_min | 2.58 |
| cell_measurement_theta_max | 23.72 |
| exptl_crystal_description | fragment |
| exptl_crystal_colour | colourless |
| exptl_crystal_size_max | 0.20 |
| exptl_crystal_size_mid | 0.18 |
| exptl_crystal_size_min | 0.15 |
| exptl_crystal_density_meas | 0 |
| exptl_crystal_density_diffrn | 1.303 |
| exptl_crystal_density_method | 'not measured' |
| exptl_crystal_F_000 | 616 |
| exptl_absorpt_coefficient_mu | 0.095 |
| exptl_absorpt_correction_type | multi-scan |
| exptl_absorpt_correction_T_min | 0.9812 |
| exptl_absorpt_correction_T_max | 0.9858 |
| exptl_absorpt_process_details | sadabs |

Crystal Structure of 7a

Figure 18:
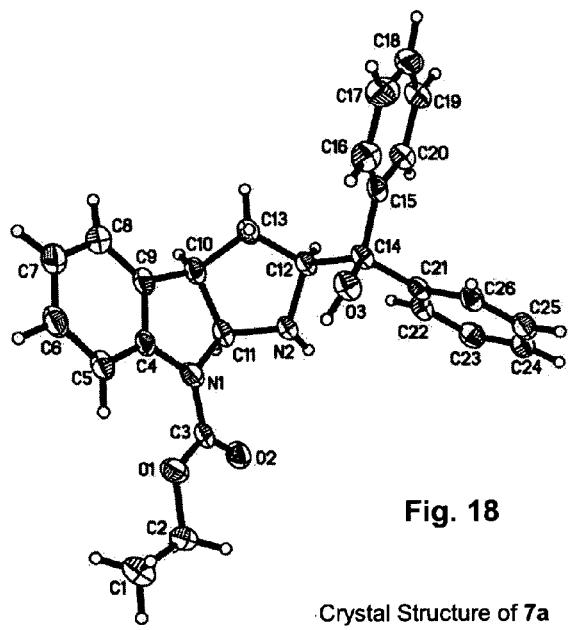
FIG. 18 shows graphically the results of X-Ray crystal data analysis of a compound of the invention of general Formula (VII) (cf. also FIG. 4A and the Examples below).
Figure 19:
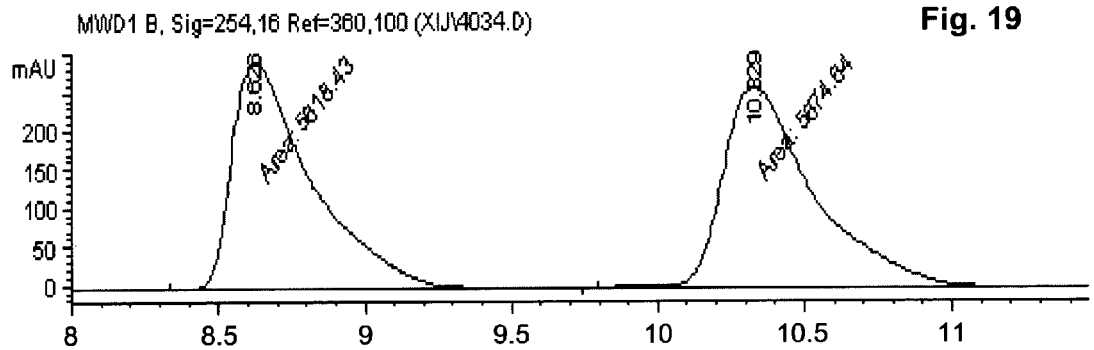
FIG. 19 depicts chiral HPLC analysis of racemic 1-phenylethanol on a Dacicel Chiralcel OD column as a reference (cf.
Figure 20:
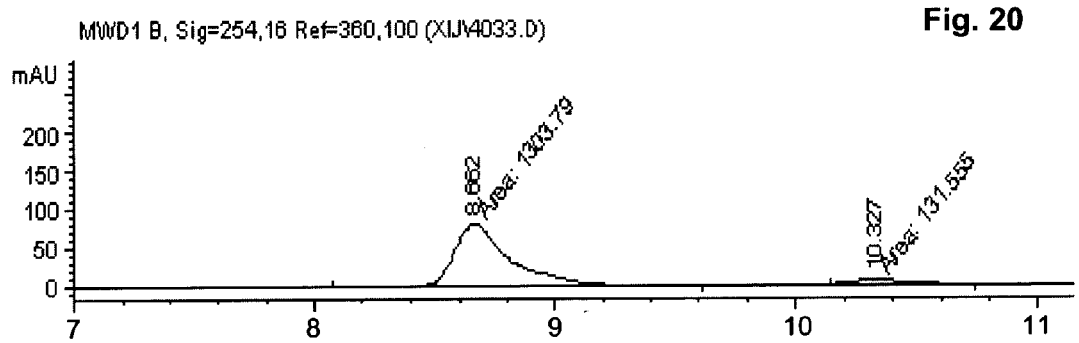
FIG. 20).

The structure is graphically represented in FIG. 18

Crystal data and structure refinement for 7a.

| | |
|---|---|
| Identification code | 7a |
| Empirical formula | C26 H26 N2 O3 |
| Formula weight | 414.49 |
| Temperature | 173(2) K |
| Wavelength | 0.71073 Å |
| Crystal system | Monoclinic |
| Space group | P2(1) |
| Unit cell dimensions | a = 11.7241 (6) Å  □ = 90°. |
| | b = 5.6398(3) Å  □ = 100.171(3)°. |
| | c = 16.4582(9) Å  □ = 90°. |
| Volume | 1071.14(10) Å$^3$ |
| Z | 2 |
| Density (calculated) | 1.285 Mg/m$^3$ |
| Absorption coefficient | 0.084 mm$^{-1}$ |
| F(000) | 440 |
| Crystal size | 0.25 × 0.08 × 0.04 mm$^3$ |
| Theta range for data collection | 1.76 to 27.99°. |
| Index ranges | −15 <= h <= 15, −7 <= k <= 6, −21 <= l <= 21 |
| Reflections collected | 9241 |
| Independent reflections | 4937 [R(int) = 0.0399] |
| Completeness to theta = 27.99° | 100.0% |

-continued

| | |
|---|---|
| Absorption correction | Semi-empirical from equivalents |
| Max. and min. transmission | 0.9966 and 0.9792 |
| Refinement method | Full-matrix least-squares on $F^2$ |
| Data/restraints/parameters | 4937/1/381 |
| Goodness-of-fit on $F^2$ | 1.022 |
| Final R indices [I > 2sigma(I)] | R1 = 0.0486, wR2 = 0.1034 |
| R indices (all data) | R1 = 0.0829, wR2 = 0.1271 |
| Absolute structure parameter | −1.4(14) |
| Largest diff. peak and hole | 0.199 and −0.302 e · Å$^{-3}$ |

Figure 16:
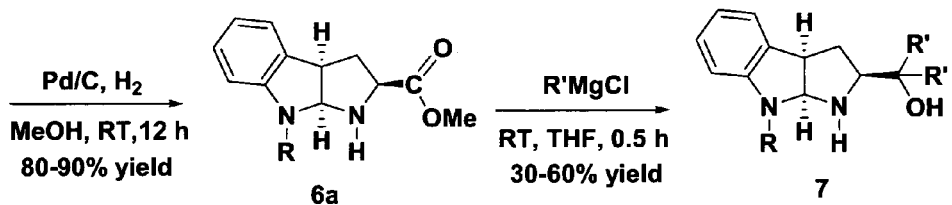
FIG. 16 shows graphically the results of X-Ray crystal data analysis of a nitroalkane product obtained in a Michael addition using a compound of the invention (see Examples for the X-Ray crystal data).

X-Ray crystal data of (2S,3R)-3-(4-bromophenyl)-2-isopropyl-4-nitrobutanal
The structure is graphically represented in FIG. 16:

| | |
|---|---|
| chemical_formula_moiety | 'C11 H12 Br N O3' |
| chemical_formula_sum | 'C11 H12 Br N O3' |
| chemical_formula_weight | 286.13 |
| symmetry_cell_setting | Monoclinic |
| symmetry_space_group_name_H-M | P2(1) |
| cell_length_a | 10.6835(6) |
| cell_length_b | 8.7762(5) |
| cell_length_c | 12.7768(7) |
| cell_angle_alpha | 90.00 |
| cell_angle_beta | 97.709(4) |
| cell_angle_gamma | 90.00 |
| cell_volume | 1187.13(12) |
| cell_formula_units_Z | 4 |
| cell_measurement_temperature | 173(2) |
| cell_measurement_reflns_used | 5754 |
| cell_measurement_theta_min | 3.01 |
| cell_measurement_theta_max | 25.95 |
| exptl_crystal_description | plate |
| exptl_crystal_colour | colourless |
| exptl_crystal_size_max | 0.40 |
| exptl_crystal_size_mid | 0.38 |
| exptl_crystal_size_min | 0.04 |
| exptl_crystal_density_diffrn | 1.601 |
| exptl_crystal_F_000 | 576 |
| exptl_absorpt_coefficient_mu | 3.454 |
| exptl_absorpt_correction_type | multi-scan |
| exptl_absorpt_correction_T_min | 0.3387 |
| exptl_absorpt_correction_T_max | 0.8742 |
| diffrn_ambient_temperature | 173(2) |
| diffrn_radiation_wavelength | 0.71073 |
| diffrn_radiation_type | MoK\a |
| diffrn_radiation_source | 'fine-focus sealed tube' |
| diffrn_radiation_monochromator | graphite |
| diffrn_measurement_device_type | 'CCD area detector' |
| diffrn_reflns_number | 23631 |
| diffrn_reflns_av_R_equivalents | 0.0520 |
| diffrn_reflns_av_sigmaI/netI | 0.0645 |
| diffrn_reflns_limit_h_min | −14 |
| diffrn_reflns_limit_h_max | 15 |
| diffrn_reflns_limit_k_min | −11 |
| diffrn_reflns_limit_k_max | 12 |
| diffrn_reflns_limit_l_min | −18 |
| diffrn_reflns_limit_l_max | 18 |
| diffrn_reflns_theta_min | 1.61 |
| diffrn_reflns_theta_max | 30.70 |
| reflns_number_total | 6685 |
| reflns_number_gt | 4423 |
| reflns_threshold_expression | >2sigma(I) |

Computational Details

DFT calculations were carried out with the Gaussian 03 package (Frisch, M J, et al., Gaussian 03, Revision D.01, Gaussian, Inc.: Wallingford, Conn., 2004). The structures are fully optimized by the B3LYP (Becke, A D J, *Chem. Phys.* (1993) 98, 1372; Becke, A D J, *Chem. Phys.* (1993) 98, 5648; Lee, C, et al, *Phys. Rev. B* (1988) 37, 785) method using 6-31G(d) basis set (Ditchfield, R, et al., J. Chem. Phys. (1971) 54, 724) and have been confirmed to be a local minima by the harmonic frequencies calculations at the same level of theory.
Computational Results and Discussions Different conformers of the enamine intermediate have been calculated to determine the lowest energy conformation in the gas phase. The lowest energy conformation syn enamine 2 is displayed in FIG. 9A. In this conformation, there is hydrogen bond between OH group and the nitrogen atom and the bond distance for N—H is 2.057 Å. The hydrogen bonding interaction can enhance the stability of this conformer, as its energy is 2.63 kJ/mol lower than that of the second lowest conformation syn enamine 1. From this conformer, we can see that, at the Si surface of enamine, there are several highly electronegative atoms such as O and N which could function as hydrogen bond acceptors. Therefore when the enamine is immersed into protic solvents such as methanol and water, the Si face is expected to develop strong hydrogen-bond networks which eventually block the attack of nitrostyrene from this side. On this basis, nitrostyrene will attack the enamine from the less hindered Re face via transition state TS1, where a water molecule is probably involved by forming hydrogen bonds with the $CO_2H$ group and $NO_2$ which will lead to the desired (S,R) product (FIG. 9B). The activation energy of this TS model is 64.61 kJ/mol lower than that of TS2 without the water molecule as hydrogen-bond bridge. The whole system is stabilized by hydrogen bonds. This proposal is supported by the following experimental results: (1) methyl ester derivative or phenyl ester derivative could not catalyze the reaction with or without acid additive in MeOH or $H_2O$, which indicate the possible activation of nitrostyrene by the carboxylic acid. (2) the reaction was much slower in aprotic solvent such DMSO and DMF which implies that $H_2O$ may be involved in the reaction through hydrogen-bonding interaction. The transition state TS3, proposed for similar reaction (Seebach model), (12. (a) Seebach, D.; Golinski, J. Helv. Chim. Acta 1981, 64, 1413. (Seebach, D, et al., Helv. Chim. Acta (1985), 68, 162) is found 7.91 kJ/mol higher than the energy of TS1 by DFT calculation.

Figure 35:
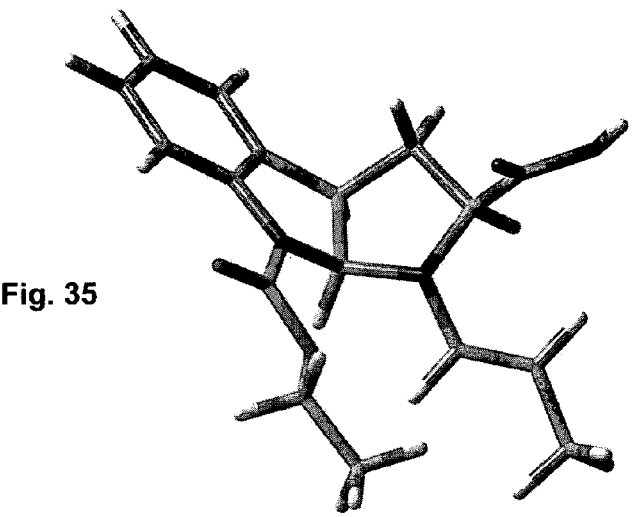
FIG. 35 depicts a further theoretically possible conformation of the enamine intermediate, a syn conformation that was compared in DFT calculation (cf. the Examples below).

Syn Enamine 1 (Depicted in FIG. 35A)

| | | | |
|---|---|---|---|
| C | 2.317253 | 0.425596 | −0.079496 |
| C | 2.482760 | −0.782657 | −0.774622 |
| C | 0.177617 | −0.103916 | −1.002930 |
| C | 1.130027 | −1.315288 | −1.159221 |
| H | −0.005180 | 0.436744 | −1.937684 |
| H | 1.077889 | −1.720655 | −2.174576 |
| N | 0.952011 | 0.802790 | −0.089580 |
| C | 0.568993 | −2.333302 | −0.131202 |
| H | 0.764459 | −3.371314 | −0.411303 |
| H | 1.028580 | −2.149221 | 0.844347 |
| C | −0.943794 | −2.028180 | −0.068650 |
| H | −1.510268 | −2.681807 | −0.747207 |
| N | −1.061177 | −0.643278 | −0.497498 |
| C | 0.492883 | 2.001811 | 0.406920 |
| O | 1.126763 | 2.751728 | 1.127752 |
| O | −0.768850 | 2.252880 | −0.017319 |
| C | −1.371410 | 3.442707 | 0.542389 |
| H | −0.759845 | 4.309026 | 0.271967 |
| H | −1.363987 | 3.357552 | 1.633156 |
| C | −1.473021 | −2.241356 | 1.350543 |
| O | −1.329398 | −1.486065 | 2.280887 |
| O | −2.099755 | −3.441925 | 1.458277 |
| H | −2.364509 | −3.525762 | 2.394146 |
| C | 3.744500 | −1.337503 | −0.938972 |
| H | 3.867611 | −2.272731 | −1.480055 |
| C | 3.412057 | 1.086604 | 0.479991 |
| H | 3.276556 | 2.010448 | 1.024591 |
| C | 4.677937 | 0.515894 | 0.304791 |
| H | 5.541540 | 1.022499 | 0.727633 |
| C | 4.854477 | −0.676578 | −0.399507 |
| H | 5.849422 | −1.093776 | −0.525535 |
| C | −2.781415 | 3.546591 | −0.007206 |
| H | −3.371593 | 2.665501 | 0.262492 |
| H | −3.272529 | 4.433767 | 0.407373 |
| H | −2.773236 | 3.640422 | −1.098532 |
| C | −2.293367 | −0.175218 | −0.956346 |
| H | −2.225026 | 0.783705 | −1.459146 |

-continued

| | | | |
|---|---|---|---|
| C | −3.485367 | −0.778505 | −0.816625 |
| H | −3.570382 | −1.722802 | −0.282755 |
| C | −4.764046 | −0.198970 | −1.355784 |
| H | −4.586872 | 0.752558 | −1.870444 |
| H | −5.248447 | −0.877181 | −2.072387 |
| H | −5.496611 | −0.012878 | −0.557742 |

SCF Energy = −1070.27086981
Zero-point correction (ZPE) = 0.354393

Figure 9A:
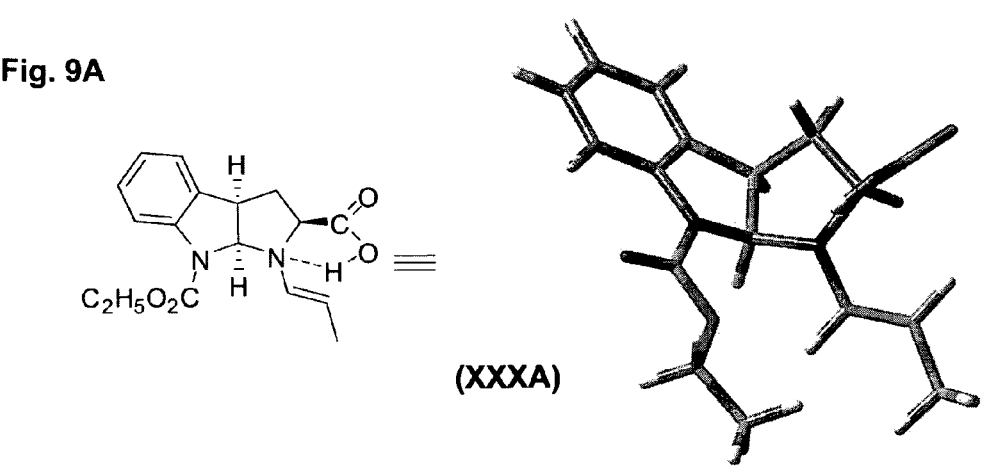
FIG. 9A depicts the most stable conformation of the enamine intermediate, a syn conformation, by DFT calculation.
Figure 9B:
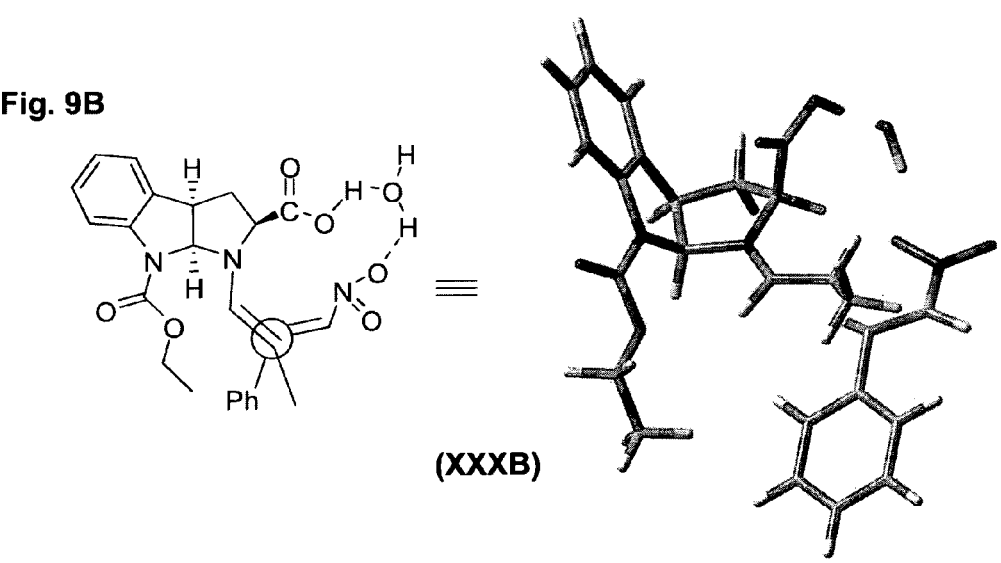
FIG. 9B depicts the lowest energy transition state (XXXA) for this reaction by DFT calculation.

Syn Enamine 2 (Depicted in FIG. 9A)

| | | | |
|---|---|---|---|
| C | 2.314188 | 0.417552 | −0.076147 |
| C | 2.461103 | −0.798361 | −0.759337 |
| C | 0.153576 | −0.119009 | −0.938252 |
| C | 1.101578 | −1.332159 | −1.117841 |
| H | −0.068211 | 0.405778 | −1.872800 |
| H | 1.030547 | −1.729786 | −2.135253 |
| N | 0.943816 | 0.796928 | −0.059363 |
| C | 0.558558 | −2.359161 | −0.093222 |
| H | 0.770182 | −3.394906 | −0.366770 |
| H | 1.012133 | −2.171863 | 0.885775 |
| C | −0.954832 | −2.080867 | −0.046814 |
| H | −1.488241 | −2.688373 | −0.789359 |
| N | −1.080124 | −0.649709 | −0.362338 |
| C | 0.509739 | 2.031141 | 0.374963 |
| O | 1.176165 | 2.826071 | 1.011664 |
| O | −0.779136 | 2.248363 | 0.012659 |
| C | −1.337184 | 3.502765 | 0.476468 |
| H | −0.728275 | 4.323493 | 0.086031 |
| H | −1.271455 | 3.530887 | 1.568266 |
| C | −1.536977 | −2.428331 | 1.330912 |
| O | −1.598476 | −1.391404 | 2.187609 |
| O | −1.861314 | −3.550191 | 1.636378 |
| C | 3.717684 | −1.361845 | −0.936138 |
| H | 3.828119 | −2.304081 | −1.467230 |
| C | 3.418881 | 1.081371 | 0.458293 |
| H | 3.297971 | 2.014470 | 0.990036 |
| C | 4.679292 | 0.502411 | 0.270335 |
| H | 5.551783 | 1.010060 | 0.672683 |
| C | 4.838195 | −0.699692 | −0.421452 |
| H | 5.828863 | −1.123634 | −0.557245 |
| C | −2.772487 | 3.576740 | −0.007864 |
| H | −3.362318 | 2.739511 | 0.378002 |
| H | −3.228270 | 4.509480 | 0.341388 |
| H | −2.821538 | 3.562785 | −1.101860 |
| C | −2.313514 | −0.209307 | −0.894727 |
| H | −2.254930 | 0.776286 | −1.343283 |
| C | −3.482968 | −0.862080 | −0.841158 |
| H | −3.556274 | −1.834437 | −0.358753 |
| C | −4.758869 | −0.303071 | −1.406641 |
| H | −5.184869 | −0.967501 | −2.170529 |
| H | −5.526364 | −0.186513 | −0.629469 |
| H | −4.599300 | 0.677541 | −1.869123 |
| H | −1.349079 | −0.591069 | 1.676648 |

SCF Energy = −1070.27180798
Zero-point correction (ZPE) = 0.354653

Figure 36:
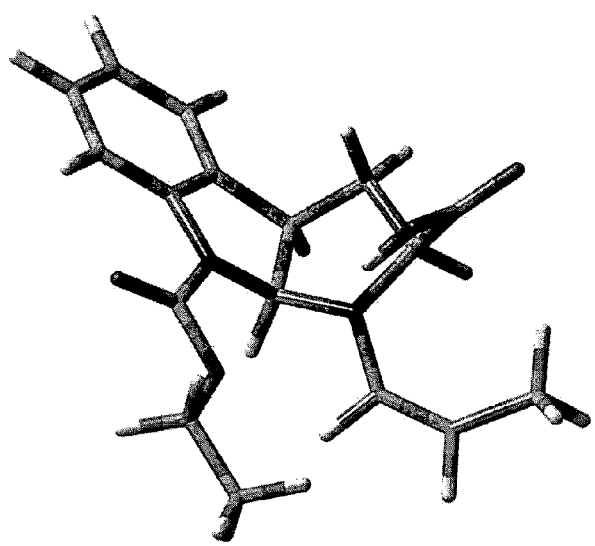
FIG. 36 depicts a further theoretically possible conformation of the enamine intermediate, a syn conformation that was compared in DFT calculation (cf. the Examples below).

Syn Enamine 3 (Depicted in FIG. 36)

| | | | |
|---|---|---|---|
| C | 2.300297 | 0.288398 | −0.031250 |
| C | 2.397101 | −0.931742 | −0.716751 |
| C | 0.162490 | −0.086417 | −1.020038 |
| C | 1.022151 | −1.366444 | −1.147072 |
| H | 0.052144 | 0.459574 | −1.961749 |
| H | 0.975885 | −1.760770 | −2.167013 |
| N | 0.959859 | 0.759896 | −0.078041 |
| C | 0.353663 | −2.343823 | −0.148450 |
| H | 0.454455 | −3.390831 | −0.441624 |
| H | 0.819397 | −2.233664 | 0.835879 |
| C | −1.131260 | −1.914370 | −0.097375 |
| H | −1.740537 | −2.536746 | −0.760876 |
| N | −1.150164 | −0.512483 | −0.547027 |
| C | 0.585706 | 2.018675 | 0.344100 |
| O | 1.269563 | 2.767495 | 1.016607 |
| O | −0.669927 | 2.312187 | −0.075577 |
| C | −1.183163 | 3.592616 | 0.367894 |
| H | −0.478483 | 4.375683 | 0.074063 |
| H | −1.236492 | 3.585907 | 1.461123 |

-continued

| | | | |
|---|---|---|---|
| C | −1.668578 | −2.079856 | 1.332984 |
| O | −1.731399 | −0.940046 | 2.043809 |
| O | −1.966201 | −3.157081 | 1.791685 |
| C | 3.619346 | −1.579355 | −0.835379 |
| H | 3.691854 | −2.524443 | −1.367927 |
| C | 3.419342 | 0.872284 | 0.562637 |
| H | 3.335497 | 1.808772 | 1.095755 |
| C | 4.645033 | 0.208865 | 0.432632 |
| H | 5.529103 | 0.653123 | 0.881931 |
| C | 4.755394 | −0.997957 | −0.260330 |
| H | 5.720262 | −1.488391 | −0.350355 |
| C | −2.548020 | 3.781913 | −0.266272 |
| H | −3.224658 | 2.966060 | 0.005973 |
| H | −2.984415 | 4.725542 | 0.078413 |
| H | −2.472583 | 3.819138 | −1.358140 |
| C | −2.279621 | 0.012286 | −1.217888 |
| H | −2.016719 | 0.890112 | −1.797670 |
| C | −3.572006 | −0.356068 | −1.222482 |
| H | −1.485272 | −0.214161 | 1.429112 |
| C | −4.353595 | −1.431432 | −0.515466 |
| H | −3.770589 | −2.096036 | 0.121348 |
| H | −5.127895 | −0.976542 | 0.117361 |
| H | −4.882749 | −2.060146 | −1.244411 |
| H | −4.188039 | 0.280060 | −1.856861 |

SCF Energy = −1070.26482028
Zero-point correction (ZPE) = 0.354984

Figure 37:
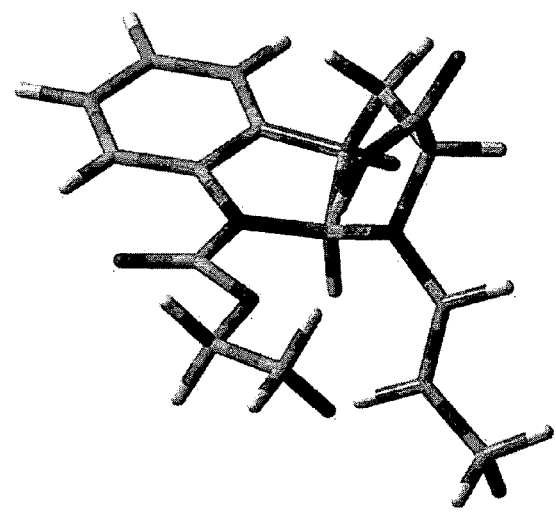
FIG. 37 depicts a further theoretically possible conformation of the enamine intermediate, an anti conformation that was compared in DFT calculation (cf. the Examples below).

Anti Enamine 4 (Depicted in FIG. 37)

| | | | |
|---|---|---|---|
| C | −2.192429 | 0.634856 | 0.193907 |
| C | −2.555215 | −0.650648 | 0.628111 |
| C | −0.200796 | −0.385911 | 0.998100 |
| C | −1.307128 | −1.455076 | 0.869396 |
| H | −0.047688 | −0.032639 | 2.022214 |
| H | −1.343349 | −2.074668 | 1.770913 |
| N | −0.775431 | 0.755817 | 0.192507 |
| C | −0.826000 | −2.285030 | −0.351221 |
| H | −1.162823 | −3.323097 | −0.321463 |
| H | −1.212541 | −1.840252 | −1.273244 |
| C | 0.721476 | −2.188344 | −0.306259 |
| H | 1.155860 | −3.089029 | 0.144592 |
| N | 1.003117 | −1.007748 | 0.519215 |
| C | −0.107826 | 1.829889 | −0.346729 |
| O | −0.634388 | 2.826654 | −0.804940 |
| O | 1.239361 | 1.626537 | −0.346674 |
| C | 2.028756 | 2.721119 | −0.884944 |
| H | 1.944242 | 3.573232 | −0.202802 |
| H | 1.603754 | 3.017231 | −1.846990 |
| C | 1.314693 | −2.070038 | −1.721235 |
| O | 1.697837 | −0.831436 | −2.082401 |
| O | 1.396508 | −3.020224 | −2.461975 |
| C | −3.891801 | −1.010680 | 0.728280 |
| H | −4.169284 | −2.006060 | 1.066268 |
| C | −3.160663 | 1.575608 | −0.156605 |
| H | −2.875230 | 2.562026 | −0.493561 |
| C | −4.504464 | 1.196741 | −0.052622 |
| H | −5.272123 | 1.919257 | −0.316301 |
| C | −4.875628 | −0.074769 | 0.387364 |
| H | −5.926169 | −0.339171 | 0.465586 |
| C | 3.458615 | 2.231752 | −1.014868 |
| H | 3.524106 | 1.391117 | −1.713312 |
| H | 4.087870 | 3.043234 | −1.396258 |
| H | 3.854399 | 1.908902 | −0.047250 |
| C | 2.199818 | −0.966385 | 1.255071 |
| H | 2.839494 | −1.825742 | 1.059436 |
| C | 2.602395 | −0.022303 | 2.117328 |
| H | 1.991195 | 0.862317 | 2.281091 |
| C | 3.888307 | −0.111123 | 2.890971 |
| H | 4.536735 | 0.754584 | 2.698619 |
| H | 3.709503 | −0.133010 | 3.974931 |
| H | 4.452518 | −1.013832 | 2.630948 |
| H | 1.568531 | −0.221477 | −1.321825 |

SCF Energy = −1070.26865670
Zero-point correction (ZPE) = 0.354347

Figure 38:
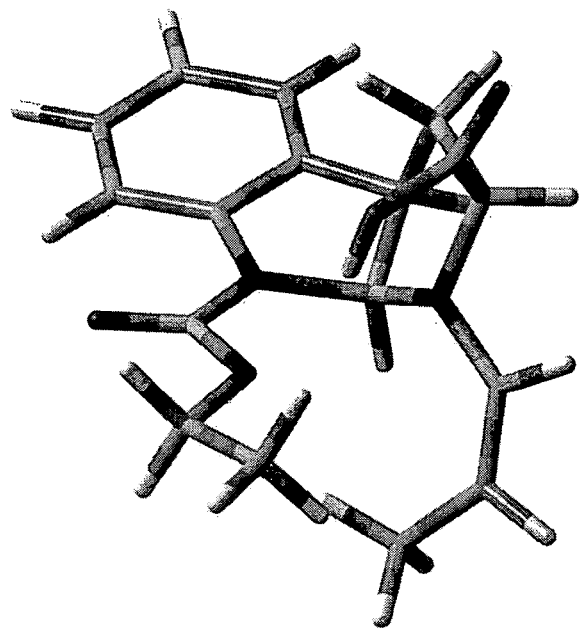
FIG. 38 depicts a further theoretically possible conformation of the enamine intermediate, an anti conformation that was compared in DFT calculation (cf. the Examples below).

Anti Enamine 5 (Depicted in FIG. 38)

| | | | |
|---|---|---|---|
| C | 2.099727 | −0.654681 | −0.012732 |
| C | 2.536948 | 0.573297 | 0.510388 |
| C | 0.217604 | 0.327665 | 1.059606 |
| C | 1.337820 | 1.379948 | 0.927510 |
| H | 0.163737 | −0.124317 | 2.051434 |
| H | 1.467452 | 1.918284 | 1.871637 |
| N | 0.682665 | −0.739427 | 0.088894 |
| C | 0.773414 | 2.319047 | −0.170947 |
| H | 1.149920 | 3.341109 | −0.097433 |
| H | 1.049140 | 1.935623 | −1.158154 |
| C | −0.763025 | 2.264341 | 0.024634 |
| H | −1.110842 | 3.126713 | 0.606019 |
| N | −1.008378 | 1.013932 | 0.760883 |
| C | −0.060293 | −1.692560 | −0.566730 |
| O | 0.397929 | −2.628929 | −1.194055 |
| O | −1.398290 | −1.447472 | −0.462813 |
| C | −2.257529 | −2.433267 | −1.099351 |
| H | −2.137742 | −3.383797 | −0.570422 |
| H | −1.920470 | −2.575327 | −2.129009 |
| C | −1.498268 | 2.316899 | −1.324989 |
| O | −1.940489 | 1.134032 | −1.788148 |
| O | −1.632557 | 3.348606 | −1.938285 |
| C | 3.888302 | 0.888320 | 0.535840 |
| H | 4.223936 | 1.839423 | 0.941679 |
| C | 3.006241 | −1.582133 | −0.525553 |
| H | 2.663019 | −2.523019 | −0.931697 |
| C | 4.365783 | −1.249017 | −0.495522 |
| H | 5.086665 | −1.961677 | −0.887021 |
| C | 4.811094 | −0.035060 | 0.030004 |
| H | 5.872592 | 0.194359 | 0.046962 |
| C | −3.680108 | −1.911440 | −1.027012 |
| H | −3.782342 | −0.971336 | −1.578379 |
| H | −4.359108 | −2.645699 | −1.473933 |
| H | −3.986265 | −1.740310 | 0.009558 |
| C | −2.150239 | 0.949516 | 1.578062 |
| H | −2.769410 | 1.834945 | 1.451437 |
| C | −2.585663 | 0.013850 | 2.439405 |
| H | −1.754232 | 0.432382 | −1.123987 |
| C | −2.015105 | −1.323252 | 2.832901 |
| H | −1.335532 | −1.738616 | 2.086280 |
| H | −1.478520 | −1.275759 | 3.791725 |
| H | −2.826292 | −2.048788 | 2.970584 |
| H | −3.508681 | 0.285531 | 2.947598 |

SCF Energy = −1070.26332004
Zero-point correction (ZPE) = 0.354781

Model TS1 (with Water) (Depicted in FIG. 9B)

| | | | |
|---|---|---|---|
| C | −3.530557 | −0.930491 | −0.024005 |
| C | −3.641584 | 0.156346 | −0.895862 |
| C | −1.389808 | −0.662939 | −0.992193 |
| C | −2.360622 | 0.335682 | −1.683965 |
| H | −0.801807 | −1.280570 | −1.669984 |
| H | −2.508445 | 0.065921 | −2.736258 |
| N | −2.238684 | −1.513092 | −0.156987 |
| C | −1.687472 | 1.717208 | −1.565429 |
| H | −1.041525 | 1.902895 | −2.430032 |
| H | −2.416888 | 2.528429 | −1.509077 |
| C | −0.822607 | 1.634052 | −0.294196 |
| H | 0.090224 | 2.228630 | −0.413776 |
| N | −0.463419 | 0.213481 | −0.220329 |
| C | −1.930398 | −2.798911 | 0.231840 |
| O | −2.668076 | −3.533808 | 0.856475 |
| O | −0.680215 | −3.148961 | −0.181575 |
| C | −0.285801 | −4.503943 | 0.159050 |
| H | −1.085203 | −5.184832 | −0.143601 |
| H | −0.182872 | −4.572170 | 1.246617 |
| C | −1.549641 | 2.093889 | 0.994999 |
| O | −1.780605 | 3.402070 | 1.058134 |
| O | −1.886718 | 1.320536 | 1.862375 |
| C | −4.821568 | 0.886771 | −0.956035 |
| H | −4.915180 | 1.733397 | −1.631871 |
| C | −4.580800 | −1.313851 | 0.805441 |
| H | −4.480326 | −2.157782 | 1.473349 |
| C | −5.762710 | −0.569401 | 0.735063 |
| H | −6.595342 | −0.846162 | 1.375604 |
| C | −5.889651 | 0.518552 | −0.131410 |
| H | −6.816800 | 1.083022 | −0.163068 |
| C | 1.017213 | −4.797742 | −0.558316 |
| H | 1.807903 | −4.102733 | −0.258502 |
| H | 1.345257 | −5.814149 | −0.315142 |
| H | 0.889102 | −4.730644 | −1.643850 |
| C | 0.537454 | −0.253984 | 0.512965 |
| H | 0.646166 | −1.335506 | 0.497175 |
| C | 1.518182 | 0.539617 | 1.166082 |
| H | 1.220533 | 1.574015 | 1.311516 |
| C | 2.163903 | −0.055524 | 2.404304 |
| H | 3.051597 | 0.522448 | 2.682642 |
| H | 1.468067 | −0.022111 | 3.250258 |
| H | 2.469149 | −1.095772 | 2.251856 |
| C | 2.885227 | 0.848207 | −0.160240 |
| H | 2.238174 | 0.935718 | −1.029391 |
| C | 3.489245 | 2.101645 | 0.164858 |
| H | 4.374794 | 2.235015 | 0.767251 |
| C | 3.753975 | −0.368785 | −0.219716 |
| C | 3.433794 | −1.388637 | −1.130061 |
| C | 4.894515 | −0.534987 | 0.582380 |
| C | 4.224143 | −2.532429 | −1.242426 |
| H | 2.563272 | −1.272013 | −1.772384 |
| C | 5.683078 | −1.680698 | 0.477741 |
| H | 5.177239 | 0.236734 | 1.291285 |
| C | 5.352420 | −2.684423 | −0.434033 |
| H | 3.964948 | −3.298448 | −1.968482 |
| H | 6.562548 | −1.785124 | 1.107320 |
| H | 5.972056 | −3.572760 | −0.519625 |
| N | 2.873390 | 3.269415 | −0.174775 |
| O | 3.354701 | 4.371800 | 0.152653 |
| O | 1.772499 | 3.208719 | −0.859789 |
| O | −0.268968 | 4.891668 | −0.537413 |
| H | 0.633234 | 4.479429 | −0.626073 |
| H | −0.503244 | 5.189833 | −1.427690 |
| H | −1.266161 | 3.939127 | 0.380667 |

SCF Energy = −1660.83606625
Zero-point correction (ZPE) = 0.519253

Figure 9C:
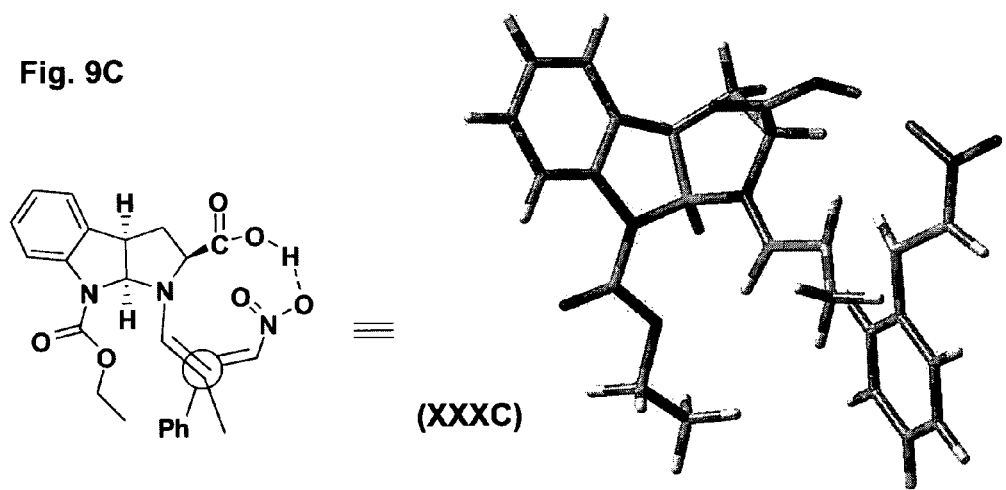
FIG. 9C depicts a theoretical alternative transition state (XXXB) that does not involve a water molecule.

Model TS2 (without Water) (Depicted in FIG. 9C)

| | | | |
|---|---|---|---|
| C | 3.570125 | 0.580467 | 0.115314 |
| C | 3.681044 | −0.424125 | −0.849212 |
| C | 1.496426 | 0.533271 | −1.008117 |
| C | 2.459555 | −0.429894 | −1.744904 |
| H | 0.970982 | 1.240604 | −1.648872 |
| H | 2.713502 | −0.031351 | −2.734641 |
| N | 2.321355 | 1.252589 | −0.042544 |
| C | 1.695279 | −1.760828 | −1.893377 |
| H | 1.187042 | −1.795276 | −2.862123 |
| H | 2.367678 | −2.620326 | −1.842561 |
| C | 0.640990 | −1.791756 | −0.765430 |
| H | −0.322884 | −2.148365 | −1.130262 |
| N | 0.492416 | −0.373527 | −0.372957 |
| C | 2.070611 | 2.531676 | 0.409623 |
| O | 2.809032 | 3.173597 | 1.128150 |
| O | 0.871184 | 2.983699 | −0.051143 |
| C | 0.529791 | 4.335791 | 0.353309 |
| H | 1.384054 | 4.985939 | 0.148803 |
| H | 0.356645 | 4.340770 | 1.434108 |
| C | 1.085914 | −2.673895 | 0.432958 |
| O | 0.356366 | −3.767348 | 0.644511 |
| O | 2.058222 | −2.392229 | 1.095526 |
| C | 4.821270 | −1.213809 | −0.905171 |
| H | 4.917043 | −1.997150 | −1.652940 |
| C | 4.576225 | 0.820048 | 1.046419 |
| H | 4.476846 | 1.605135 | 1.783274 |
| C | 5.717509 | 0.014184 | 0.981613 |
| H | 6.517158 | 0.177828 | 1.698502 |
| C | 5.844966 | −0.991869 | 0.021323 |
| H | 6.739692 | −1.606753 | −0.004974 |
| C | −0.704072 | 4.748302 | −0.425404 |
| H | −1.545789 | 4.076466 | −0.229677 |

-continued

| | | | |
|---|---|---|---|
| H | −0.998575 | 5.761534 | −0.131430 |
| H | −0.504024 | 4.749673 | −1.502035 |
| C | −0.438579 | 0.068928 | 0.462330 |
| H | −0.435481 | 1.145512 | 0.613078 |
| C | −1.456003 | −0.727920 | 1.057093 |
| H | −1.199419 | −1.781877 | 1.100733 |
| C | −2.028676 | −0.212623 | 2.366564 |
| H | −2.930009 | −0.777926 | 2.626593 |
| H | −1.310616 | −0.345501 | 3.183598 |
| H | −2.293939 | 0.848442 | 2.312795 |
| C | −2.866891 | −0.911554 | −0.201495 |
| H | −2.262131 | −1.062334 | −1.092560 |
| C | −3.577766 | −2.097652 | 0.170540 |
| H | −4.486472 | −2.119511 | 0.752556 |
| C | −3.629035 | 0.377046 | −0.260872 |
| C | −3.266986 | 1.337197 | −1.219040 |
| C | −4.702101 | 0.671022 | 0.595404 |
| C | −3.953019 | 2.546778 | −1.325682 |
| H | −2.447346 | 1.122727 | −1.901840 |
| C | −5.387315 | 1.882072 | 0.495047 |
| H | −5.011214 | −0.050303 | 1.345021 |
| C | −5.016516 | 2.825292 | −0.464525 |
| H | −3.664984 | 3.265392 | −2.088440 |
| H | −6.217089 | 2.085400 | 1.166502 |
| H | −5.555876 | 3.764898 | −0.546089 |
| N | −3.036080 | −3.329301 | −0.052002 |
| O | −3.600601 | −4.361274 | 0.353277 |
| O | −1.914866 | −3.401182 | −0.708667 |
| H | −0.499792 | −3.780981 | 0.116326 |

SCF Energy = −1584.39884194
Zero-point correction (ZPE) = 0.494339

Figure 39:
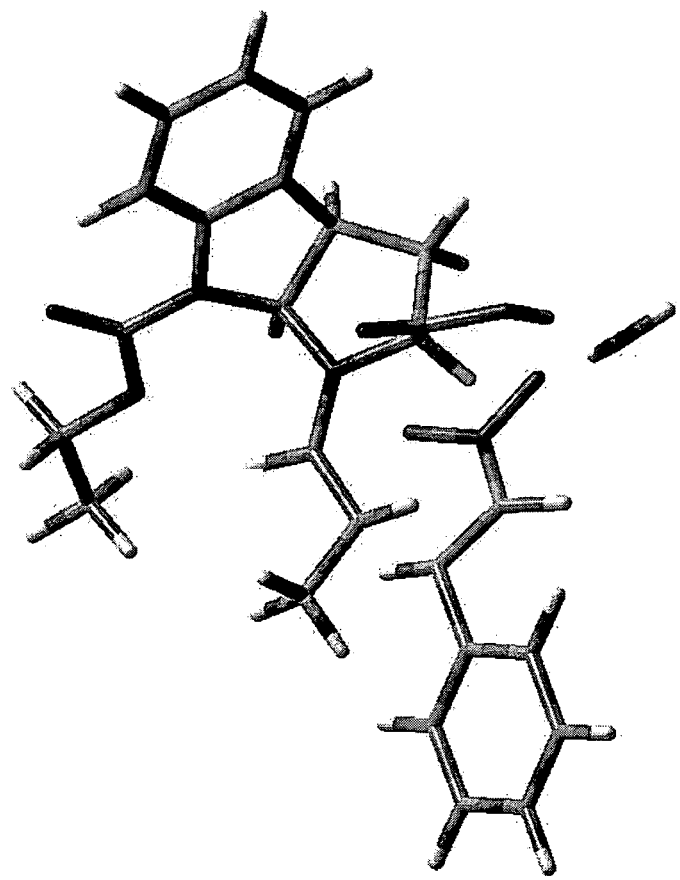
FIG. 39 depicts a theoretically possible conformation of the transition state that was compared in DFT calculation (cf. the Examples below).

Model TS3 (with Water) (Depicted in FIG. 39)

| | | | |
|---|---|---|---|
| C | −3.728275 | 0.185967 | −0.411241 |
| C | −3.604276 | −1.030849 | 0.269226 |
| C | −1.752290 | 0.350125 | 0.859136 |
| C | −2.477901 | −0.947405 | 1.279668 |
| H | −1.387288 | 0.961473 | 1.683537 |
| H | −2.880350 | −0.848539 | 2.294921 |
| N | −2.716098 | 1.081181 | 0.038131 |
| C | −1.398138 | −2.036392 | 1.240288 |
| H | −0.852501 | −2.056952 | 2.187197 |
| H | −1.807269 | −3.031428 | 1.049810 |
| C | −0.417977 | −1.593893 | 0.127997 |
| H | 0.598813 | −1.823659 | 0.424702 |
| N | −0.574749 | −0.134342 | 0.083194 |
| C | −2.774575 | 2.450515 | −0.096539 |
| O | −3.640699 | 3.057493 | −0.694833 |
| O | −1.722587 | 3.046290 | 0.529212 |
| C | −1.734205 | 4.495008 | 0.499644 |
| H | −2.658419 | 4.845136 | 0.968901 |
| H | −1.744210 | 4.825528 | −0.543191 |
| C | −0.654695 | −2.296632 | −1.217698 |
| O | −0.237745 | −3.574331 | −1.198530 |
| O | −1.153707 | −1.781509 | −2.187566 |
| C | −4.482490 | −2.072360 | 0.000167 |
| H | −4.394923 | −3.019763 | 0.526417 |
| C | −4.719584 | 0.394853 | −1.365868 |
| H | −4.807692 | 1.344211 | −1.876093 |
| C | −5.594868 | −0.664371 | −1.628275 |
| H | −6.374922 | −0.528602 | −2.372272 |
| C | −5.482575 | −1.885719 | −0.960378 |
| H | −6.172177 | −2.693616 | −1.186853 |
| H | −0.502600 | 4.974669 | 1.243405 |
| H | 0.415074 | 4.632318 | 0.753541 |
| H | −0.489849 | 6.069708 | 1.263738 |
| H | −0.499258 | 4.609880 | 2.275212 |
| C | 0.350245 | 0.715349 | −0.343141 |
| H | 0.089127 | 1.757492 | −0.176622 |
| C | 1.589642 | 0.435761 | −0.963567 |
| H | 1.711008 | −0.575654 | −1.346411 |
| C | 2.071713 | 1.520822 | −1.916412 |
| H | 3.098342 | 1.338561 | −2.239853 |
| H | 1.442017 | 1.558874 | −2.814053 |
| H | 2.038044 | 2.510931 | −1.444557 |
| C | 2.976097 | 0.323514 | 0.553391 |
| H | 2.722679 | 1.273683 | 1.014120 |
| C | 2.710309 | −0.805756 | 1.367179 |
| H | 3.135568 | −1.783407 | 1.193793 |
| C | 4.261610 | 0.328371 | −0.197335 |
| C | 5.056924 | 1.484994 | −0.196827 |
| C | 4.724492 | −0.801437 | −0.893618 |
| C | 6.286928 | 1.508865 | −0.854320 |
| H | 4.711734 | 2.367731 | 0.335718 |
| C | 5.949410 | −0.776010 | −1.556408 |
| H | 4.119539 | −1.703782 | −0.924068 |
| C | 6.737077 | 0.378362 | −1.537157 |
| H | 6.891516 | 2.411516 | −0.833542 |
| H | 6.290022 | −1.658751 | −2.090603 |
| H | 7.692519 | 0.395973 | −2.054089 |
| N | 1.728532 | −0.770772 | 2.310672 |
| O | 1.387846 | −1.873496 | 2.880794 |
| O | 1.146103 | 0.309098 | 2.600668 |
| O | 1.315154 | −3.976145 | 1.085126 |
| H | 1.387040 | −3.285225 | 1.796565 |
| H | 1.303581 | −4.826567 | 1.547569 |
| H | 0.263541 | −3.776861 | −0.364382 |

SCF Energy = −1660.83004325
Zero-point correction (ZPE) = 0.518898

Water

| | | | |
|---|---|---|---|
| O | −0.024248 | 0.000000 | −0.017137 |
| H | 0.025062 | 0.000000 | 0.950263 |
| H | 0.904123 | 0.000000 | −0.293580 |

SCF Energy = −76.4089533236
Zero-point correction (ZPE) = 0.021168

In summary, a new class of structurally rigid tricyclic amphibian chiral catalysts based on the hexahydropyrrolo[2,3-b]indole skeleton has been developed. The special features of this catalyst include: (1) easily prepared in large scale; (2) 10/DMAP catalyst has been shown to afford the desired products in high yields and excellent enantioselectivities in the Michael addition of aldehydes to nitroalkenes both in organic solvents and in water; (3) only slight excess of aldehyde is used in this system; (4) low catalyst loading and broad substrate scope. Efficient enamine control has been shown and without being bound by theory evidence points to the involvement of a chiral pocket. Further, Ligand 7a has been used for the asymmetric reduction of ketones to afford the desired product in excellent yield and high enantioselectivities. These advantages render these chiral catalyste particularly suitable for practical use and will certainly find application in asymmetric synthesis. The success of this novel catalyst design will open up new perspectives in chiral catalyst or ligand design. Further applications to other asymmetric reactions using this new catalyst or using this skeleton as chiral ligand as well as mechanistic insight are ongoing in our group. These advantages further render the chiral 10/DMAP catalyst more competitive than proline and more suitable for practical use, thus it will certainly find wide application in organocatalysis. Finally, the success of this novel catalyst design clarifies that it is inefficient enamine control due to proline's skeleton and not the hydrogen bonding interaction which is responsible for the failure of poor hydrogen bond acceptors to serve as electrophiles.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

What is claimed is:

1. A hexahydropyrrolo[2,3-b]indole compound of Formula (XX)

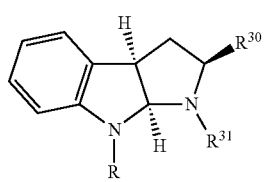

(XX)

wherein R is —COOR$^3$,
wherein R$^3$ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si,
R$^{31}$ is hydrogen;
R$^{30}$ is one of —C(OH)R$^1$R$^2$ and —COOH,
wherein R$^1$ and R$^2$ are independent from one another, and wherein
R$^1$ and R$^2$ are selected from one of hydrogen, an aliphatic group with a main chain having 1 to about 20 carbon atoms, and an aromatic group.

2. A hexahydropyrrolo[2,3-b]indole compound of Formula (VII)

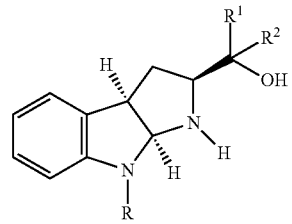

(VII)

wherein R is —COOR$^3$,
wherein R$^3$ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si, and
R$^1$ and R$^2$ are independent from one another, each selected from one of hydrogen, an aliphatic group with a main chain having 1 to about 20 carbon atoms, and an aromatic group.

3. The compound of claim 2 wherein R$^1$ and R$^2$ are identical.

4. A compound of Formula (VIA)

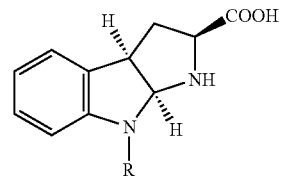

(VIA)

wherein R is —COOR$^3$,
wherein R$^3$ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si.

5. A method of forming a compound of Formula (VIA)

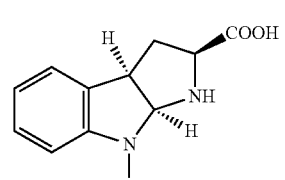

(VIA)

wherein R is —COOR$^3$,
wherein R$^3$ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si, and the method comprising providing a compound of Formula (IVA)

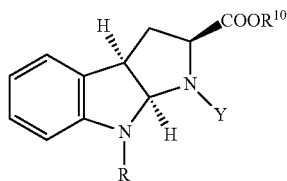

(IVA)

wherein in Formula (IVA) R is —COOR³,
wherein R³ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si, and Y is a nitrogen protecting group that is removable by hydrogenolysis, and R¹⁰ is a protecting group that is removable in the presence of R by hydrogenolysis; and exposing the compound of Formula (IVA) to H₂ in the presence of a suitable catalyst, thereby (i) allowing the deprotection of the Nα group of compound (IVA) and (ii) allowing the cleavage of the ester bond to moiety R¹⁰ of compound (IVA).

6. The method of claim 5, wherein R¹⁰ is aryl-methylenyl.

7. The method of claim 5, wherein providing the compound of Formula (IVA) comprises contacting a compound of Formula (IIIA)

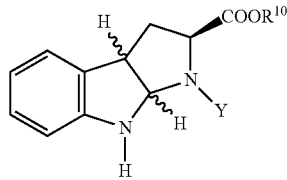

(IIIA)

with an acyl halide RCOX in the presence of an alkali base,
wherein in Formula (IIIA) Y is a nitrogen protecting group that is removable by hydrogenolysis,
R¹⁰ is a protecting group that is removable in the presence of R in a compound of Formula (IVA) by hydrogenolysis, and
X is halogen.

8. A method of preparing a compound of Formula (VII)

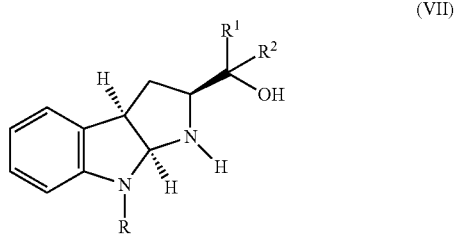

(VII)

wherein R is —COOR³,
wherein R³ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si, and R¹ and R² are independent from one another, each selected from one of hydrogen, an aliphatic group with a main chain having 1 to about 20 carbon atoms, and an aromatic group;

the method comprising reacting a compound of Formula (VI)

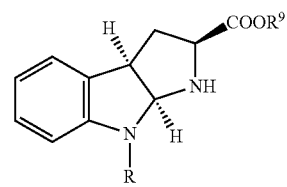

(VI)

with a compound R¹MgX, R²MgX or a mixture of R¹MgX and R²MgX,
wherein R¹ and R² are independent from one another, each selected from one of hydrogen, an aliphatic group with a main chain having 1 to about 20 carbon atoms, and an aromatic group;
wherein in Formula VI, R is —COOR³,
wherein R³ is selected from one of hydrogen, an aliphatic group with a main chain having 1 to about 20 carbon atoms, an alicyclic group, an aromatic group, an arylaliphatic group and an arylalicyclic group, comprising 0 to about 3 heteroatoms independently selected from the group consisting of N, O, S, Se and Si, and R⁹ is alkyl.

9. The method of claim 8, wherein R¹ and R² are identical.

10. The method of claim 7, wherein the compound of Formula (IIIA) is prepared by a process that comprises an acid catalyzed cyclization of an Nα-protected-tryptophan alkyl ester.

* * * * *